US010039755B2

(12) United States Patent
Atkinson et al.

(10) Patent No.: US 10,039,755 B2
(45) Date of Patent: Aug. 7, 2018

(54) 2-(AZAINDOL-2-YL) BENZIMIDAZOLES AS PAD4 INHIBITORS

(71) Applicant: Glaxo Group Limited, Brentford (GB)

(72) Inventors: Stephen John Atkinson, Stevenage (GB); Michael David Barker, Stevenage (GB); Matthew Campbell, Stevenage (GB); Hawa Diallo, Stevenage (GB); Clement Douault, Stevenage (GB); Neil Stuart Garton, Stevenage (GB); John Liddle, Stevenage (GB); Robert John Sheppard, Stevenage (GB); Ann Louise Walker, Stevenage (GB); Christopher Wellaway, Stevenage (GB); David Matthew Wilson, Stevenage (GB)

(73) Assignee: Glaxo Group Limited, Brentford (GB)

( * ) Notice: Subject to any disclaimer, the term of this patent is extended or adjusted under 35 U.S.C. 154(b) by 0 days.

(21) Appl. No.: 15/817,562

(22) Filed: Nov. 20, 2017

(65) Prior Publication Data

US 2018/0161316 A1    Jun. 14, 2018

Related U.S. Application Data

(60) Continuation of application No. 15/352,340, filed on Nov. 15, 2016, now Pat. No. 9,833,449, which is a division of application No. 14/816,246, filed on Aug. 3, 2015, now Pat. No. 9,518,054, which is a continuation of application No. 14/416,937, filed as application No. PCT/EP2012/064649 on Jul. 26, 2012, now Pat. No. 9,127,003.

(51) Int. Cl.
*A61K 31/4545*       (2006.01)

(52) U.S. Cl.
CPC .............................. *A61K 31/4545* (2013.01)

(58) Field of Classification Search
None
See application file for complete search history.

(56) References Cited

U.S. PATENT DOCUMENTS

| 2006/0063822 A1 | 3/2006 | Weinstein et al. |
| 2009/0311217 A1 | 12/2009 | Buravich et al. |

FOREIGN PATENT DOCUMENTS

| FR | 2862971 A1 | 6/2005 |
| RU | 2011106786 A | 8/2012 |
| WO | 2001028993 A2 | 4/2001 |
| WO | 2001047922 A1 | 7/2001 |
| WO | 2003000690 A1 | 1/2003 |
| WO | 2003000695 A1 | 1/2003 |
| WO | 2005047289 A1 | 5/2005 |
| WO | 2009042092 A1 | 4/2009 |
| WO | 2010115736 A2 | 10/2010 |

OTHER PUBLICATIONS

Fuhrmann et al., "Protein Arginine Methylation and Citrullination in Epigenetic Regulation," American Chemical Society Chemical Biology, vol. 11, No Month Listed 2016 (pp. 654-668).
International Search Report and Written Opinion issued by the European Patent Office as International Searching Authority for International Application No. PCT/EP2012/064649 dated Sep. 19, 2012 (4 pages).
Jones et al., "Protein Arginine Deiminase 4 (PAD4): Current Understanding and Future Therapeutic Potential," Current Opinion Drug Discovery Development, vol. 12, No. 5, Sep. 2009 (pp. 616-627).
Khandpur et al., "NETs are a source of citrullinated autoantigens and stimulate inflammatory responses in rheumatoid arthritis," Science Translational Medicine, vol. 5, No. 178, Mar. 27, 2013 (23 pages).
Luo et al., "Inhibitors and Inactivators of Protein Arginine Deiminase 4: Functional and Structural Characterization," Biochemistry, vol. 45, No. 39, Oct. 3, 2006 (pp. 11727-11736).
No Author Listed, "Etiology (medicine)," Wikipedia, retrieved from internet <https://en.wikipedia.org/w/index.php?title=Etiology_(medicine)&oldid=724535723> accessed Aug. 3, 2016 (2 pages).
No Author Listed, "GSK-484 hydrochloride," BioVision, Product Information Sheet, Apr. 2016 (1 pages).
No Author Listed, "Symptomatic Treatment," Wikipedia, retrieved from internet <https://en.wikipedia.org/w/index.php?title=Symptomatic_treatment&oldid=544289442> accessed Aug. 3, 2016 (1 page).
Teo et al., "Discovery of a New Class of Inhibitors for the Protein Arginine Deiminase Type 4 (PAD4) by Structure-Based Virtual Screening," BMC Bioinformatics, vol. 13(Suppl 17), S4, No Month Listed 2012 (13 pages).
Willis, "The Role of Citrullination in the Development of Mouse and Human Inflammatory Arthritis," A thesis submitted to the Faculty of the Graduate School of the University of Colorado, Doctor of Philosophy, Molecular Biology Program, Nov. 20, 2012 (146 pages).

*Primary Examiner* — Heidi Reese
(74) *Attorney, Agent, or Firm* — Andrea L. C. Reid; Dechert LLP

(57) ABSTRACT

Compounds of formula (I) wherein; $R_1$ is hydrogen or $C_{1-6}$alkyl; $R_2$ is hydrogen, $C_{1-6}$alkyl, perhalomethyl$C_{0-5}$alkyl-O—, or $C_{1-6}$alkoxy; $R_3$ is hydrogen, $C_{1-6}$alkyl, or $C_{1-6}$alkoxy$C_{1-6}$alkyl; $R_4$ is hydrogen, $C_{1-6}$alkyl, perhalomethyl$C_{1-6}$alkyl; or unsubstituted $C_{3-6}$cycloalkyl$C_{1-6}$alkyl; A is C—$R_5$ or N; B is C—$R_6$ or N; D is C—$R_7$ or N; with the proviso that at least one of A, B, and D, is N; $R_5$ is hydrogen or $C_{1-6}$alkyl; $R_6$ is hydrogen or $C_{1-6}$alkyl; $R_7$ is hydrogen, $C_{1-6}$alkyl, $C_{1-6}$alkoxy, or hydroxy; $R_8$ is hydrogen or $C_{1-6}$alkyl, with the proviso that one of $R_4$ and $R_8$ is hydrogen; $R_9$ is hydrogen or hydroxy; $R_{10}$ is hydrogen or $C_{1-6}$alkyl; and salts thereof are PAD4 inhibitors and may be useful in the treatment of various disorders, for example rheumatoid arthritis, vasculitis, systemic lupus erythematosus, ulcerative colitis, cancer, cystic fibrosis, asthma, cutaneous lupus erythematosis, and psoriasis.

9 Claims, No Drawings

2-(AZAINDOL-2-YL) BENZIMIDAZOLES AS PAD4 INHIBITORS

FIELD OF THE INVENTION

The present invention is directed to certain novel compounds which are inhibitors of PAD4, processes for their preparation, pharmaceutical compositions comprising the compounds, and the use of the compounds or the compositions in the treatment of various disorders. Compounds which inhibit PAD4 may be useful in the treatment of various disorders, for example rheumatoid arthritis, vasculitis, systemic lupus erythematosus, ulcerative colitis, cancer, cystic fibrosis, asthma, cutaneous lupus erythematosis, and psoriasis.

BACKGROUND OF THE INVENTION

PAD4 is a member of the peptidylarginine deiminase (PAD) family of enzymes capable of catalysing the citrullination of arginine into citrulline within peptide sequences. PAD4 is responsible for the deimination or citrullination of a variety of proteins in vitro and in vivo, with consequences of diverse functional responses in a variety of diseases (Jones J. E. et al, Curr. Opin. Drug Discov. Devel., 12(5), (2009), 616-627). Examples of exemplar diseases include rheumatoid arthritis, diseases with neutrophilic contributions to pathogenesis (for example vasculitis, systemic lupus erythematosus, ulcerative colitis) in addition to oncology indications. PAD4 inhibitors may also have wider applicability as tools and therapeutics for human disease through epigenetic mechanisms.

Inhibitors of PAD4 may have utility against Rheumatoid Arthritis (RA). RA is an auto-immune disease affecting approximately 1% of the population (Wegner N. et al, Immunol. Rev., 233(1) (2010), 34-54). It is characterised by inflammation of articular joints leading to debilitating destruction of bone and cartilage. A weak genetic association between PAD4 polymorphisms and susceptibility to RA has been suggested, albeit inconsistently, in a number of population studies (Kochi Y. et al, Ann. Rheum. Dis., 70, (2011), 512-515). PAD4 (along with family member PAD2) has been detected in synovial tissue where it is responsible for the deimination of a variety of joint proteins. This process is presumed to lead to a break of tolerance to, and initiation of immune responses to, citrullinated substrates such as fibrinogen, vimentin and collagen in RA joints. These anti-citrullinated protein antibodies (ACPA) contribute to disease pathogenesis and may also be used as a diagnostic test for RA (e.g. the commercially available CCP2 or cyclic citrullinated protein 2 test). In addition, increased citrullination may also offer additional direct contributions to disease pathogenesis through its ability to affect directly the function of several joint and inflammatory mediators (e.g. fibrinogen, anti-thrombin, multiple chemokines). In a smaller subset of RA patients, anti-PAD4 antibodies can be measured and may correlate with a more erosive form of the disease.

PAD4 inhibitors may also be useful for the reduction of pathological neutrophil activity in a variety of diseases. Studies suggest that the process of Neutrophil Extracellular Trap (NET) formation, an innate defence mechanism by which neutrophils are able to immobilise and kill pathogens, is associated with histone citrullination and is deficient in PAD4 knockout mice (Neeli I. et al, J. Immunol., 180, (2008), 1895-1902 and Li P. et al, J. Exp. Med., 207(9), (2010), 1853-1862). PAD4 inhibitors may therefore have applicability for diseases where NET formation in tissues contributes to local injury and disease pathology. Such diseases include, but are not limited to, small vessel vasculitis (Kessenbrock K. et al, Nat. Med., 15(6), (2009), 623-625), systemic lupus erythematosus (Hakkim A. et al, Proc. Natl. Acad. Sci. USA, 107(21), (2010), 9813-9818 and Villanueva E. et al, J. Immunol., 187(1), (2011), 538-52), ulcerative colitis (Savchenko A. et al, Pathol. Int., 61(5), (2011), 290-7), cystic fibrosis, asthma (Dworski R. et al, J. Allergy Clin. Immunol., 127(5), (2011), 1260-6), deep vein thrombosis (Fuchs T. et al, Proc. Natl. Acad. Sci. USA, 107(36), (2010), 15880-5), periodontitis (Vitkov L. et al, Ultrastructural Pathol., 34(1), (2010), 25-30), sepsis (Clark S. R. et al, Nat. Med., 13(4), (2007), 463-9), appendicitis (Brinkmann V. et al, Science, 303, (2004), 1532-5), and stroke. In addition, there is evidence that NETs may contribute to pathology in diseases affecting the skin, eg in cutaneous lupus erythematosus (Villanueva E. et al, J. Immunol., 187(1), (2011), 538-52) and psoriasis (Lin A. M. et al., J. Immunol., 187(1), (2011), 490-500), so a PAD4 inhibitor may show benefit to tackle NET skin diseases, when administered by a systemic or cutaneous route. PAD4 inhibitors may affect additional functions within neutrophils and have wider applicability to neutrophilic diseases.

Studies have demonstrated efficacy of tool PAD inhibitors (for example chloro-amidine) in a number of animal models of disease, including collagen-induced arthritis (Willis V. C. et al, J. Immunol., 186(7), (2011), 4396-4404), dextran sulfate sodium (DSS)-induced experimental colitis (Chumanevich A. A. et al, Am. J. Physiol. Gastrointest. Liver Physiol., 300(6), (2011), G929-G938), spinal cord repair (Lange S. et al, Dev. Biol., 355(2), (2011), 205-14), and experimental autoimmune encephalomyelitis (EAE). The DSS colitis report also demonstrates that chloro-amidine drives apoptosis of inflammatory cells both in vitro and in vivo, suggesting that PAD4 inhibitors may be effective more generally in widespread inflammatory diseases.

PAD4 inhibitors may also be useful in the treatment of cancers (Slack. J. L. et al, Cell. Mol. Life Sci., 68(4), (2011), 709-720). Over-expression of PAD4 has been demonstrated in numerous cancers (Chang X. et al, BMC Cancer, 9, (2009), 40). An anti-proliferative role has been suggested for PAD4 inhibitors from the observation that PAD4 citrullinates arginine residues in histones at the promoters of p53-target genes such as p21, which are involved in cell cycle arrest and induction of apoptosis (Li P. et al, Mol. Cell Biol., 28(15), (2008), 4745-4758).

The aforementioned role of PAD4 in deiminating arginine residues in histones may be indicative of a role for PAD4 in epigenetic regulation of gene expression. PAD4 is the primary PAD family member observed to be resident in the nucleus as well as the cytoplasm. Early evidence that PAD4 may act as a histone demethyliminase as well as a deiminase is inconsistent and unproven. However, it may reduce histone arginine methylation (and hence epigenetic regulation associated with this mark) indirectly via depletion of available arginine residues by conversion to citrulline. PAD4 inhibitors may therefore be useful as epigenetic tools or therapeutics for affecting expression of varied target genes in additional disease settings. Through such mechanisms, PAD4 inhibitors may also be effective in controlling citrullination levels in stem cells and may therefore therapeutically affect the pluripotency status and differentiation potential of diverse stem cells including, but not limited to, embryonic stem cells, neural stem cells, haematopoietic stem cells and cancer stem cells.

SUMMARY OF THE INVENTION

The invention is directed to compounds of formula (I):

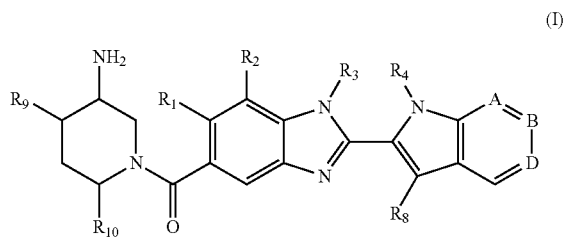

wherein $R_1$, $R_2$, $R_3$, $R_4$, A, B, D, $R_8$, $R_9$, and $R_{10}$ are as defined below;
and salts thereof.

Certain compounds of the invention have been shown to be PAD4 inhibitors and may also show enhanced selectivity for PAD4 with respect to PAD2. For example, certain compounds of the invention indicate 1000-fold selectivity for PAD4 inhibition over PAD2 inhibition. Compounds which inhibit PAD4 may be useful in the treatment of various disorders, for example rheumatoid arthritis, vasculitis, systemic lupus erythematosus, ulcerative colitis, cancer, cystic fibrosis, asthma, cutaneous lupus erythematosis, and psoriasis. Accordingly, the invention is further directed to pharmaceutical compositions comprising a compound of formula (I), or a pharmaceutically acceptable salt thereof. The invention is still further directed to methods of treatment of disorders associated therewith using a compound of formula (I) or a pharmaceutically acceptable salt thereof, or a pharmaceutical composition comprising a compound of formula (I) or a pharmaceutically acceptable salt thereof. The invention is yet further directed towards processes for the preparation of the compounds of the invention.

DETAILED DESCRIPTION OF THE INVENTION

In a first aspect, there are provided compounds of formula (I):

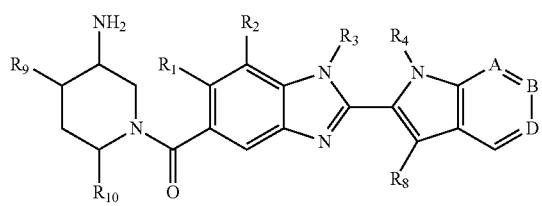

wherein;
$R_1$ is hydrogen or $C_{1-6}$alkyl;
$R_2$ is hydrogen, $C_{1-6}$alkyl, perhalomethyl$C_{0-5}$alkyl-O—, or $C_{1-6}$alkoxy;
$R_3$ is hydrogen, $C_{1-6}$alkyl, or $C_{1-6}$alkoxy$C_{1-6}$alkyl;
$R_4$ is hydrogen, $C_{1-6}$alkyl, perhalomethyl$C_{1-6}$alkyl; or unsubstituted $C_{3-6}$cycloalkyl$C_{1-6}$alkyl;
A is C—$R_5$ or N;

B is C—$R_6$ or N;
D is C—$R_7$ or N;
with the proviso that at least one of A, B, and D, is N;
$R_5$ is hydrogen or $C_{1-6}$alkyl;
$R_6$ is hydrogen or $C_{1-6}$alkyl;
$R_7$ is hydrogen, $C_{1-6}$alkyl, $C_{1-6}$alkoxy, or hydroxy;
$R_8$ is hydrogen or $C_{1-6}$alkyl, with the proviso that one of $R_4$ and $R_8$ is hydrogen;
$R_9$ is hydrogen or hydroxy;
$R_{10}$ is hydrogen or $C_{1-6}$alkyl;
and salts thereof.

In one embodiment, $R_1$ is hydrogen.
In one embodiment, $R_1$ is $C_{1-6}$alkyl.
In one embodiment, $R_2$ is hydrogen or $C_{1-6}$alkoxy.
In one embodiment, $R_2$ is $C_{1-6}$alkoxy.
In one embodiment, $R_2$ is perhalomethyl$C_{0-5}$alkyl-O—.
In one embodiment, $R_2$ is trifluoromethoxy.
In one embodiment, $R_3$ is hydrogen.
In one embodiment, $R_3$ is $C_{1-6}$alkoxy$C_{1-6}$alkyl.
In one embodiment, $R_3$ is $C_{1-6}$alkyl.
In one embodiment, $R_4$ is $C_{1-6}$alkyl, unsubstituted $C_{3-6}$cycloalkyl$C_{1-6}$alkyl, or perhalomethyl$C_{1-6}$alkyl.
In one embodiment, $R_4$ is $C_{1-6}$alkyl, unsubstituted $C_{3-6}$cycloalkyl$C_{1-6}$alkyl, or perfluoromethyl$C_{1-6}$alkyl.
In one embodiment, $R_5$ is hydrogen.
In one embodiment, $R_6$ is hydrogen.
In one embodiment, $R_7$ is hydrogen, $C_{1-6}$alkoxy, or hydroxy.
In one embodiment, $R_7$ is hydrogen.
In one embodiment, $R_8$ is hydrogen.
In one embodiment, $R_9$ is hydrogen.
In one embodiment, $R_9$ is hydroxy.
In one embodiment, $R_{10}$ is hydrogen.
In one embodiment, $R_{10}$ is hydroxy.

In one embodiment, the compound of the invention is selected from the list consisting of:
1-{[2-(1-ethyl-1H-pyrrolo[3,2-c]pyridin-2-yl)-1-methyl-1H-benzimidazol-5-yl]carbonyl}-3-piperidinamine;
(R)-(3-aminopiperidin-1-yl)(2-(1-ethyl-1H-pyrrolo[2,3-b]pyridin-2-yl)-1-methyl-1H-benzo[d]imidazol-5-yl)methanone;
(R)-(3-aminopiperidin-1-yl)(2-(1-ethyl-1H-pyrrolo[2,3-c]pyridin-2-yl)-1-methyl-1H-benzo[d]imidazol-5-yl)methanone;
(R)-(3-aminopiperidin-1-yl)(1-methyl-2-(1-(2,2,2-trifluoroethyl)-1H-pyrrolo[2,3-b]pyridin-2-yl)-1H-benzo[d]imidazol-5-yl)methanone;
(R)-(3-aminopiperidin-1-yl)(2-(1-(cyclopropylmethyl)-1H-pyrrolo[2,3-b]pyridin-2-yl)-1-methyl-1H-benzo[d]imidazol-5-yl)methanone;
(R)-(3-aminopiperidin-1-yl)(2-(1-ethyl-5-methoxy-1H-pyrrolo[2,3-b]pyridin-2-yl)-1-methyl-1H-benzo[d]imidazol-5-yl)methanone;
(R)-(3-aminopiperidin-1-yl)(2-(1-ethyl-5-methoxy-1H-pyrrolo[2,3-c]pyridin-2-yl)-1-methyl-1H-benzo[d]imidazol-5-yl)methanone;
2-(5-{[(3R)-3-amino-1-piperidinyl]carbonyl}-1-methyl-1H-benzimidazol-2-yl)-1-ethyl-1H-pyrrolo[2,3-b]pyridin-5-ol;
(R)-(3-aminopiperidin-1-yl)(2-(1-ethyl-1H-pyrrolo[2,3-b]pyridin-2-yl)-7-methoxy-1-methyl-1H-benzo[d]imidazol-5-yl)methanone;
(R)-(3-aminopiperidin-1-yl)(2-(1-(cyclopropylmethyl)-1H-pyrrolo[2,3-b]pyridin-2-yl)-7-methoxy-1-methyl-1H-benzo[d]imidazol-5-yl)methanone;

(R)-(3-aminopiperidin-1-yl)(7-methoxy-1-methyl-2-(1-(2,2,2-trifluoroethyl)-1H-pyrrolo[2,3-b]pyridin-2-yl)-1H-benzo[d]imidazol-5-yl)methanone;
(3-aminopiperidin-1-yl)(2-(1-ethyl-1H-pyrrolo[2,3-b]pyridin-2-yl)-1-methyl-1H-benzo[d]imidazol-5-yl)methanone;
(R)-(3-aminopiperidin-1-yl)(2-(1-ethyl-1H-pyrrolo[2,3-b]pyridin-2-yl)-1-methyl-7-(trifluoromethoxy)-1H-benzo[d]imidazol-5-yl)methanone;
(R)-(3-aminopiperidin-1-yl)(7-methoxy-1-methyl-2-(1-neopentyl-1H-pyrrolo[2,3-b]pyridin-2-yl)-1H-benzo[d]imidazol-5-yl)methanone;
((R)-3-aminopiperidin-1-yl)(7-methoxy-1-methyl-2-(1-(2-methylbutyl)-1H-pyrrolo[2,3-b]pyridin-2-yl)-1H-benzo[d]imidazol-5-yl)methanone, and;
(R)-(3-aminopiperidin-1-yl)(7-methoxy-2-(1-(2-methoxy-2-methylpropyl)-1H-pyrrolo[2,3-b]pyridin-2-yl)-1-methyl-1H-benzo[d]imidazol-5-yl)methanone;
and salts thereof.

In one embodiment, the compound of the invention is selected from the list consisting of:
(R)-(3-aminopiperidin-1-yl)(2-(1-ethyl-1H-pyrrolo[2,3-b]pyridin-2-yl)-1-methyl-1H-benzo[d]imidazol-5-yl)methanone hydrochloride;
(R)-(3-aminopiperidin-1-yl)(1-methyl-2-(1-(2,2,2-trifluoroethyl)-1H-pyrrolo[2,3-b]pyridin-2-yl)-1H-benzo[d]imidazol-5-yl)methanone hydrochloride;
(R)-(3-aminopiperidin-1-yl)(2-(1-(cyclopropylmethyl)-1H-pyrrolo[2,3-b]pyridin-2-yl)-1-methyl-1H-benzo[d]imidazol-5-yl)methanone, hydrochloride;
(R)-(3-aminopiperidin-1-yl)(2-(1-ethyl-1H-pyrrolo[2,3-b]pyridin-2-yl)-7-methoxy-1-methyl-1H-benzo[d]imidazol-5-yl)methanone, hydrochloride;
(R)-(3-aminopiperidin-1-yl)(2-(1-(cyclopropylmethyl)-1H-pyrrolo[2,3-b]pyridin-2-yl)-7-methoxy-1-methyl-1H-benzo[d]imidazol-5-yl)methanone, hydrochloride;
(R)-(3-aminopiperidin-1-yl)(7-methoxy-1-methyl-2-(1-(2,2,2-trifluoroethyl)-1H-pyrrolo[2,3-b]pyridin-2-yl)-1H-benzo[d]imidazol-5-yl)methanone, hydrochloride;
((3S,4R)-3-amino-4-hydroxypiperidin-1-yl)(2-(1-(cyclopropylmethyl)-1H-pyrrolo[2,3-b]pyridin-2-yl)-1-methyl-1H-benzo[d]imidazol-5-yl)methanone, hydrochloride;
((3S,4R)-3-amino-4-hydroxypiperidin-1-yl)(2-(1-(cyclopropylmethyl)-1H-pyrrolo[2,3-b]pyridin-2-yl)-7-methoxy-1-methyl-1H-benzo[d]imidazol-5-yl)methanone, hydrochloride;
(R)-(3-aminopiperidin-1-yl)(2-(1-ethyl-1H-pyrrolo[2,3-b]pyridin-2-yl)-7-methoxy-1-(2-methoxyethyl)-1H-benzo[d]imidazol-5-yl)methanone, hydrochloride;
(S)-(3-aminopiperidin-1-yl)(2-(1-ethyl-1H-pyrrolo[2,3-b]pyridin-2-yl)-7-methoxy-1-methyl-1H-benzo[d]imidazol-5-yl)methanone, hydrochloride;
(R)-(3-aminopiperidin-1-yl)(2-(1-ethyl-1H-pyrrolo[2,3-b]pyridin-2-yl)-1-isobutyl-7-methoxy-1H-benzo[d]imidazol-5-yl)methanone, hydrochloride;
(R)-(3-aminopiperidin-1-yl)(2-(1-isobutyl-1H-pyrrolo[2,3-b]pyridin-2-yl)-7-methoxy-1-methyl-1H-benzo[d]imidazol-5-yl)methanone, hydrochloride;
((2R,5S)-5-amino-2-methylpiperidin-1-yl)(2-(1-(cyclopropylmethyl)-1H-pyrrolo[2,3-b]pyridin-2-yl)-7-methoxy-1-methyl-1H-benzo[d]imidazol-5-yl)methanone, hydrochloride, and;
((2R,5S)-5-amino-2-methylpiperidin-1-yl)(2-(1-(cyclopropylmethyl)-1H-pyrrolo[2,3-b]pyridin-2-yl)-7-methoxy-1-methyl-1H-benzo[d]imidazol-5-yl)methanone, hydrochloride.

In one embodiment, the compound of the invention is selected from the list consisting of:
((3S,4R)-3-amino-4-hydroxypiperidin-1-yl)(2-(1-(cyclopropylmethyl)-1H-pyrrolo[2,3-b]pyridin-2-yl)-1-methyl-1H-benzo[d]imidazol-5-yl)methanone;
((3S,4R)-3-amino-4-hydroxypiperidin-1-yl)(2-(1-(cyclopropylmethyl)-1H-pyrrolo[2,3-b]pyridin-2-yl)-7-methoxy-1-methyl-1H-benzo[d]imidazol-5-yl)methanone;
(R)-(3-aminopiperidin-1-yl)(2-(1-ethyl-1H-pyrrolo[2,3-b]pyridin-2-yl)-7-methoxy-1-(2-methoxyethyl)-1H-benzo[d]imidazol-5-yl)methanone;
(S)-(3-aminopiperidin-1-yl)(2-(1-ethyl-1H-pyrrolo[2,3-b]pyridin-2-yl)-7-methoxy-1-methyl-1H-benzo[d]imidazol-5-yl)methanone;
(R)-(3-aminopiperidin-1-yl)(2-(1-ethyl-1H-pyrrolo[2,3-b]pyridin-2-yl)-1-isobutyl-7-methoxy-1H-benzo[d]imidazol-5-yl)methanone;
(R)-(3-aminopiperidin-1-yl)(2-(1-isobutyl-1H-pyrrolo[2,3-b]pyridin-2-yl)-7-methoxy-1-methyl-1H-benzo[d]imidazol-5-yl)methanone;
((2R,5S)-5-amino-2-methylpiperidin-1-yl)(2-(1-(cyclopropylmethyl)-1H-pyrrolo[2,3-b]pyridin-2-yl)-7-methoxy-1-methyl-1H-benzo[d]imidazol-5-yl)methanone, and;
((2R,5S)-5-amino-2-methylpiperidin-1-yl)(2-(1-(cyclopropylmethyl)-1H-pyrrolo[2,3-b]pyridin-2-yl)-7-methoxy-1-methyl-1H-benzo[d]imidazol-5-yl)methanone;
and salts thereof.

In one embodiment, the compound of the invention is selected from the list consisting of:
(R)-(3-aminopiperidin-1-yl)(2-(1-(cyclopropylmethyl)-1H-pyrrolo[2,3-b]pyridin-2-yl)-1-methyl-1H-benzo[d]imidazol-5-yl)methanone;
(R)-(3-aminopiperidin-1-yl)(2-(1-ethyl-1H-pyrrolo[2,3-b]pyridin-2-yl)-7-methoxy-1-methyl-1H-benzo[d]imidazol-5-yl)methanone;
(R)-(3-aminopiperidin-1-yl)(2-(1-(cyclopropylmethyl)-1H-pyrrolo[2,3-b]pyridin-2-yl)-7-methoxy-1-methyl-1H-benzo[d]imidazol-5-yl)methanone;
(R)-(3-aminopiperidin-1-yl)(7-methoxy-1-methyl-2-(1-(2,2,2-trifluoroethyl)-1H-pyrrolo[2,3-b]pyridin-2-yl)-1H-benzo[d]imidazol-5-yl)methanone, and;
((3S,4R)-3-amino-4-hydroxypiperidin-1-yl)(2-(1-(cyclopropylmethyl)-1H-pyrrolo[2,3-b]pyridin-2-yl)-7-methoxy-1-methyl-1H-benzo[d]imidazol-5-yl)methanone;
and salts thereof.

In one embodiment, the compound of the invention is selected from the list consisting of:
(R)-(3-aminopiperidin-1-yl)(2-(1-(cyclopropylmethyl)-1H-pyrrolo[2,3-b]pyridin-2-yl)-1-methyl-1H-benzo[d]imidazol-5-yl)methanone, hydrochloride;
(R)-(3-aminopiperidin-1-yl)(2-(1-ethyl-1H-pyrrolo[2,3-b]pyridin-2-yl)-7-methoxy-1-methyl-1H-benzo[d]imidazol-5-yl)methanone, hydrochloride;
(R)-(3-aminopiperidin-1-yl)(2-(1-(cyclopropylmethyl)-1H-pyrrolo[2,3-b]pyridin-2-yl)-7-methoxy-1-methyl-1H-benzo[d]imidazol-5-yl)methanone, hydrochloride;
(R)-(3-aminopiperidin-1-yl)(7-methoxy-1-methyl-2-(1-(2,2,2-trifluoroethyl)-1H-pyrrolo[2,3-b]pyridin-2-yl)-1H-benzo[d]imidazol-5-yl)methanone, hydrochloride, and;
((3S,4R)-3-amino-4-hydroxypiperidin-1-yl)(2-(1-(cyclopropylmethyl)-1H-pyrrolo[2,3-b]pyridin-2-yl)-7-methoxy-1-methyl-1H-benzo[d]imidazol-5-yl)methanone, hydrochloride.

There is further provided a subset of compounds of formula (I), being of formula (I')

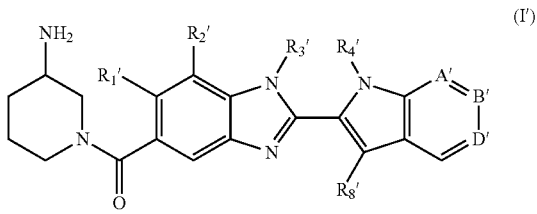

(I')

wherein;
$R_{1'}$ is hydrogen or $C_{1-6}$alkyl;
$R_{2'}$ is hydrogen, $C_{1-6}$alkyl, or $C_{1-6}$alkoxy;
$R_{3'}$ is hydrogen or $C_{1-6}$alkyl;
$R_{4'}$ is hydrogen, $C_{1-6}$alkyl, perhalomethyl$C_{1-6}$alkyl; or unsubstituted $C_{3-6}$cycloalkyl$C_{1-6}$alkyl;
A' is C—$R_5$ or N;
B' is C—$R_6$, or N;
D' is C—$R_7$, or N;
with the proviso that at least one of A', B', and D', is N;
$R_{5'}$ is hydrogen or $C_{1-6}$alkyl;
$R_{6'}$ is hydrogen or $C_{1-6}$alkyl;
$R_{7'}$ is hydrogen, $C_{1-6}$alkyl, $C_{1-6}$alkoxy, or hydroxy;
$R_{8'}$ is hydrogen or $C_{1-6}$alkyl, with the proviso that one of $R_{4'}$ and $R_{8'}$ is hydrogen;
and salts thereof.

It will be understood that references herein to compounds of formula (I) are equally-applicable to compounds of formula (I'), for example methods of preparation, compositions, and methods of use.

Terms and Definitions

Compounds of Formula (I) and salts thereof are referred to hereinafter as 'Compounds of the invention'.

'Alkyl' refers to a saturated hydrocarbon chain having the specified number of carbon atoms. For example, $C_{1-6}$alkyl refers to an alkyl group having from 1 to 6 carbon atoms, for example 1 to 2 carbon atoms. Alkyl groups may be straight or branched. Representative branched alkyl groups have one, two, or three branches. 'Alkyl' includes methyl and ethyl.

'Alkoxy' refers to a saturated hydrocarbon chain having the specified number of carbon atoms linked by a single bond to an oxygen atom. For example, $C_{1-6}$alkoxy refers to an alkoxy group having from 1 to 6 carbon atoms, for example 1 to 2 carbon atoms, for example 1 carbon atom. Alkoxy groups may be straight or branched. Representative branched alkoxy groups have one, two, or three branches. 'Alkoxy' includes methoxy.

'Cycloalkyl' refers to a saturated hydrocarbon ring having the specified number of member atoms. For example, $C_{3-6}$cycloalkyl refers to a cycloalkyl group having from 3 to 6 member atoms, for example 3 member atoms. 'Cycloalkyl' includes cyclopropyl.

'Enantiomeric excess' (ee) is the excess of one enantiomer over the other expressed as a percentage. In a racemic modification, since both enantiomers are present in equal amounts, the enantiomeric excess is zero (0% ee). However, if one enantiomer were enriched such that it constitutes 95% of the product, then the enantiomeric excess would be 90% ee (the amount of the enriched enantiomer, 95%, minus the amount of the other enantiomer, 5%).

'Enantiomerically enriched' refers to products whose enantiomeric excess (ee) is greater than zero. For example, 'enantiomerically enriched' refers to products whose enantiomeric excess is greater than 50% ee, greater than 75% ee, and greater than 90% ee.

'Enantiomerically pure' refers to products whose enantiomeric excess is 99% or greater.

'Half-life' (or 'half-lives') refers to the time required for half of a quantity of a substance to be converted to another chemically distinct species in vitro or in vivo.

'Halo' refers to a halogen radical, for example, fluoro, chloro, bromo, or iodo, for example bromo, chloro, or fluoro.

'Perhalomethyl' refers to a methyl group in which all of the hydrogen atoms have been replaced with a halogen radical. An example of perhalomethyl is perfluoromethyl i.e. $CF_3$—.

'Heterocyclic' and 'heterocyclyl' refer to saturated or unsaturated monocyclic aliphatic rings containing 5, 6, or 7 ring members including 1 or 2 heteroatoms or to saturated or unsaturated bicyclic aliphatic rings containing 6, 7, or 8 ring members including 1 or 2 heteroatoms. In certain embodiments, 'heterocyclyl groups' are saturated. In other embodiments, 'heterocyclyl' groups are unsaturated. 'Heterocyclyl' groups containing more than one heteroatom may contain different heteroatoms. 'Heterocyclyl' groups may be substituted with one or more substituents as defined herein. 'Heterocyclyl' includes piperidinyl.

'Heteroaryl' refers to aromatic rings containing from 1 to 3 heteroatoms as member atoms in the ring. 'Heteroaryl' groups containing more than one heteroatom may contain different heteroatoms. 'Heteroaryl' groups may be substituted with one or more substituents if so defined herein. The 'heteroaryl' rings have 5 or 6 member atoms. 'Heteroaryl' includes pyrrolopyridinyl and benzimidazolyl.

'Heteroatom' refers to a nitrogen, sulfur, or oxygen atom, for example a nitrogen atom.

'Member atoms' refers to the atom or atoms that form a chain or ring. Where more than one member atom is present in a chain and within a ring, each member atom is covalently bound to an adjacent member atom in the chain or ring. Atoms that make up a substituent group on a chain or ring are not member atoms in the chain or ring.

'Substituted' in reference to a group indicates that a hydrogen atom attached to a member atom within a group is replaced. It should be understood that the term 'substituted' includes the implicit provision that such substitution be in accordance with the permitted valence of the substituted atom and the substituent and that the substitution results in a stable compound (i.e. one that does not spontaneously undergo transformation such as rearrangement, cyclisation, or elimination). In certain embodiments, a single atom may be substituted with more than one substituent as long as such substitution is in accordance with the permitted valence of the atom. Suitable substituents are defined herein for each substituted or optionally substituted group.

'Pharmaceutically acceptable' refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

Throughout the description and the claims which follow, unless the context requires otherwise, the word 'comprise', and variations such as 'comprises' and 'comprising', will be understood to imply the inclusion of a stated integer or step or group of integers but not to the exclusion of any other integer or step or group of integers or steps.

As used herein the symbols and conventions used in these processes, schemes and examples are consistent with those used in the contemporary scientific literature, for example, the *Journal of the American Chemical Society*. Unless otherwise noted, all starting materials were obtained from commercial suppliers and used without further purification. Specifically, the following abbreviations may be used in the examples and throughout the specification:

ABBREVIATIONS

| | |
|---|---|
| AcOH | Acetic acid |
| $BH_3$-THF | Borane tetrahydrofuran complex |
| BOC/Boc | tert-Butoxycarbonyl |
| $BOC_2O$ | Di-tert-butyl dicarbonate |
| nBuLi | n-Butyllithium |
| BuOH | Butanol |
| cHex | Cyclohexane |
| $Cs_2CO_3$ | Caesium carbonate |
| CV | Column volumes |
| $DCM/CH_2Cl_2$ | Dichloromethane |
| Dioxane | 1,4-dioxane |
| DIPEA | N,N-diisopropylethylamine |
| DMSO | Dimethylsulfoxide |
| DMF | N,N-dimethylformamide |
| $Et_3N$ | Triethylamine |
| Ether | Diethyl ether |
| EtOAc | Ethyl acetate |
| GC | Gas chromatography |
| h. | Hours |
| HATU | o-(7-Azabenzotriazol-1-yl)-N,N,N',N'-tetramethyl-uronium hexafluorophosphate |
| HPLC | High performance liquid chromatography |
| $K_2CO_3$ | Potassium carbonate |
| KOH | Potassium hydroxide |
| LiCl | Lithium chloride |
| LiOH | Lithium hydroxide |
| LCMS or LC/MS | Liquid chromatography-mass spectroscopy |
| MDAP | Mass directed automated preparative chromatography |
| MeOH | Methanol |
| MeNH2 | Methylamine |
| min. | Minutes |
| $Na_2SO_4$ | Sodium sulfate |
| $NaHCO_3$ | Sodium bicarbonate |
| $NH_4Cl$ | Ammonium chloride |
| NMP | 1-Methyl-2-pyrrolidinone |
| Pd/C | Palladium on carbon |
| PE | Petroleum ether |
| rb | round-bottomed (flask) |
| r.t/rt. | Room temperature |
| Rt | Retention time |
| SNAP | Biotage ™ flash chromatography cartridge |
| SP4 | Biotage ™ flash purification system |
| TFA | Trifluoroacetic acid |
| THF/thf | Tetrahydrofuran |
| TLC/tlc | Thin layer chromatography |
| TMEDA | Tetramethylethylenediamine |

Included within the scope of the 'compounds of the invention' are all solvates (including hydrates), complexes, polymorphs, prodrugs, radiolabelled derivatives, and stereoisomers of the compounds of formula (I) and salts thereof.

The compounds of the invention may exist in solid or liquid form. In the solid state, the compounds of the invention may exist in crystalline or non-crystalline form, or as a mixture thereof. For compounds of the invention that are in crystalline form, the skilled artisan will appreciate that pharmaceutically acceptable solvates may be formed wherein solvent molecules are incorporated into the crystalline lattice during crystallization. Solvates may involve non-aqueous solvents such as ethanol, iso-propyl alcohol, N,N-dimethylsulfoxide (DMSO), acetic acid, ethanolamine, and ethyl acetate, or they may involve water as the solvent that is incorporated into the crystalline lattice. Solvates wherein water is the solvent that is incorporated into the crystalline lattice are typically referred to as 'hydrates'. Hydrates include stoichiometric hydrates as well as compositions containing variable amounts of water. The invention includes all such solvates.

It will be further appreciated that certain compounds of the invention that exist in crystalline form, including the various solvates thereof, may exhibit polymorphism (i.e. the capacity to occur in different crystalline structures). These different crystalline forms are typically known as 'polymorphs'. The invention includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. It will be appreciated that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

The invention also includes isotopically-labelled compounds, which are identical to the compounds of formula (I) and salts thereof, but for the fact that one or more atoms are replaced by an atom having an atomic mass or mass number different from the atomic mass or mass number most commonly found in nature. Examples of isotopes that can be incorporated into the compounds of the invention include isotopes of hydrogen, carbon, nitrogen, oxygen and fluorine, such as $^3H$, $^{11}C$, $^{14}C$ and $^{18}F$.

The compounds according to formula (I) contain one or more asymmetric centres (also referred to as a chiral centres) and may, therefore, exist as individual enantiomers, diastereoisomers, or other stereoisomeric forms, or as mixtures thereof. Chiral centres, such as chiral carbon atoms, may also be present in a substituent such as an alkyl group. Where the stereochemistry of a chiral centre present in formula (I), or in any chemical structure illustrated herein, is not specified, the structure is intended to encompass any stereoisomer and all mixtures thereof. Thus, compounds according to formula (I) containing one or more chiral centres may be used as racemic modifications including racemic mixtures and racemates, enantiomerically-enriched mixtures, or as enantiomerically-pure individual stereoisomers. For example, the fragment (Z) of the compounds of formula (I) illustrated below:

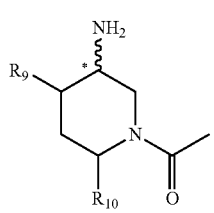

contains a chiral centre at the junction of the amino-group with the ring (marked with an asterisk (*)). The stereochemistry at this chiral centre may be R, S, RS, or any mixture of R and S stereoisomers.

Individual stereoisomers of a compound according to formula (I) which contain one or more asymmetric centres may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. It will be appreciated that where the desired stereoisomer is converted into another chemical entity by one of the separation procedures described above, a further step is required to liberate the desired form. Alternatively, specific stereoisomers may be synthesised by asymmetric synthesis using optically active reagents, substrates, catalysts or solvents, or by converting one enantiomer to the other by asymmetric transformation.

It is to be understood that the references herein to compounds of formula (I) and salts thereof covers the compounds of formula (I) as free bases, or as salts thereof, for example as pharmaceutically acceptable salts thereof. Thus, in one embodiment, the invention is directed to compounds of formula (I) as the free base. In another embodiment, the invention is directed to compounds of formula (I) and salts thereof. In a further embodiment, the invention is directed to compounds of formula (I) and pharmaceutically acceptable salts thereof.

It will be appreciated that pharmaceutically acceptable salts of the compounds according to formula (I) may be prepared. Indeed, in certain embodiments of the invention, pharmaceutically acceptable salts of the compounds according to formula (I) may be preferred over the respective free base because such salts impart greater stability or solubility to the molecule thereby facilitating formulation into a dosage form. Accordingly, the invention is further directed to compounds of formula (I) and pharmaceutically acceptable salts thereof.

As used herein, the term 'pharmaceutically acceptable salts' refers to salts that retain the desired biological activity of the subject compound and exhibit minimal undesired toxicological effects. These pharmaceutically acceptable salts may be prepared in situ during the final isolation and purification of the compound, or by separately reacting the purified compound in its free base form with a suitable acid.

Salts and solvates having non-pharmaceutically acceptable counter-ions or associated solvents are within the scope of the present invention, for example, for use as intermediates in the preparation of other compounds of formula (I) and their pharmaceutically acceptable salts. Thus one embodiment of the invention embraces compounds of formula (I) and salts thereof.

Compounds according to formula (I) contain a basic functional group and are therefore capable of forming pharmaceutically acceptable acid addition salts by treatment with a suitable acid. Suitable acids include pharmaceutically acceptable inorganic acids and pharmaceutically acceptable organic acids. Representative pharmaceutically acceptable acid addition salts include hydrochloride, hydrobromide, nitrate, methylnitrate, sulfate, bisulfate, sulfamate, phosphate, acetate, hydroxyacetate, phenylacetate, propionate, butyrate, iso-butyrate, valerate, maleate, hydroxymaleate, acrylate, fumarate, malate, tartrate, citrate, salicylate, p-aminosalicyclate, glycollate, lactate, heptanoate, phthalate, oxalate, succinate, benzoate, o-acetoxybenzoate, chlorobenzoate, methylbenzoate, dinitrobenzoate, hydroxybenzoate, methoxybenzoate, naphthoate, hydroxynaphthoate, mandelate, tannate, formate, stearate, ascorbate, palmitate, oleate, pyruvate, pamoate, malonate, laurate, glutarate, glutamate, estolate, methanesulfonate (mesylate), ethanesulfonate (esylate), 2-hydroxyethanesulfonate, benzenesulfonate (besylate), p-aminobenzenesulfonate, p-toluenesulfonate (tosylate), and naphthalene-2-sulfonate.

Compound Preparation

The compounds of the invention may be made by a variety of methods, including standard chemistry. Any previously defined variable will continue to have the previously defined meaning unless otherwise indicated. Illustrative general synthetic methods are set out in the following schemes, and can be readily adapted to prepare other compounds of the invention. Specific compounds of the invention are prepared in the Examples section.

A compound of formula (I) may be prepared by deprotection of a compound of formula (II). Accordingly, in a first aspect, there is provided a process for the preparation of a compound of formula (I) by deprotection of a compound of formula (II):

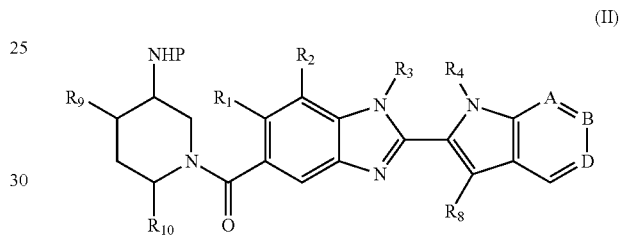

(II)

wherein $R_1$, $R_2$, $R_3$, $R_4$, A, B, D, $R_8$, $R_9$, and $R_{10}$ are as hereinbefore defined, and P is a suitable protecting group for amines, for example tert-butoxycarbonyl (Boc), and thereafter, if required, preparing a salt of the compound so formed.

For example, to a solution of a compound of formula (II) in a suitable solvent, for example dichloromethane, is added trifluoroacetic acid and the reaction stirred at a suitable temperature, for example ambient temperature, for a suitable period of time, for example 1-3 hours. The reaction mixture is then concentrated under reduced pressure. The crude product is then dissolved in a suitable solvent, for example methanol, and loaded onto an ion-exchange cartridge, for example a strong cation-exchange cartridge. The product is then eluted as the free base with a suitable solvent, for example 2M ammonia in methanol and the eluant concentrated under reduced pressure to yield a compound of formula (I).

A compound of formula (II) may be prepared by condensation of a compound of formula (III):

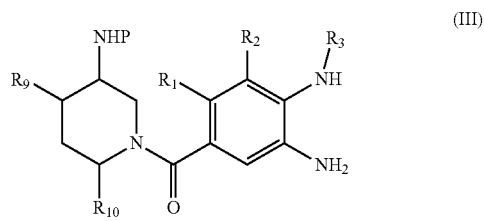

(III)

wherein $R_1$, $R_2$, $R_3$, $R_9$, $R_{10}$, and P are as hereinbefore defined, with a compound of formula (IV)

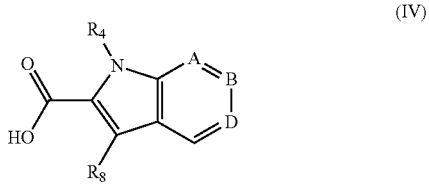

(IV)

wherein $R_4$, A, B, D, and $R_8$ are as hereinbefore defined.

In a further aspect, there is provided a process for the preparation of a compound of formula (II) by reaction of a compound of formula (III) with a compound of formula (IV).

For example, a compound of formula (IV) and a suitable peptide coupling reagent, for example o-(7-azabenzotriazol-1-yl)-N,N,N',N'-tetramethyluronium hexafluorophosphate (HATU), are dissolved in a suitable solvent, for example N,N-dimethylformamide and stirred at a suitable temperature, for example ambient temperature, for a suitable period of time, for example 5-10 minutes. To this is added a solution of a compound of formula (III), and a suitable hindered base, for example N,N-di-iso-propylethylamine (DIPEA), in a suitable solvent, for example N,N-dimethylformamide, and the resulting mixture stirred under nitrogen at a suitable temperature, for example ambient temperature, for a suitable period of time, for example 3-5 hours. The reaction mixture is diluted with water and partitioned with a suitable organic solvent, for example ether. The organic layer is isolated then the aqueous layer re-extracted with ether. The combined organic layers are washed with water then dried over sodium sulfate then passed through a hydrophobic frit and concentrated under reduced pressure to give the crude amide intermediate. The solid is dried under reduced pressure for 12-24 hours then dissolved in a suitable solvent, for example toluene. A suitable organic acid, for example acetic acid is added to the reaction mixture and then the mixture is heated to reflux for a suitable period of time, for example which was refluxed for 4-6 hours. A suitable aqueous base, for example sodium bicarbonate solution is added to the reaction mixture and the organic layer isolated. The aqueous layer is re-extracted with a suitable organic solvent, for example toluene, and the combined organic layers concentrated under reduced pressure to give the crude product. The crude material may be purified by, for example, column chromatography.

A compound of formula (II) may also be prepared by reaction of a compound of formula (XX):

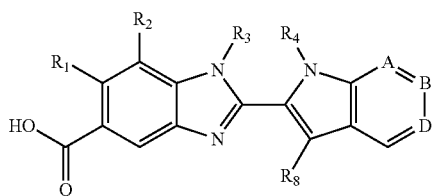

(XX)

wherein $R_1$, $R_2$, $R_3$, $R_4$, A, B, D, and $R_8$ are as hereinbefore defined, with a compound of formula (X) as hereinafter defined.

For example, to a solution of a compound of formula (XX) in a suitable solvent, for example N,N-dimethylformamide (DMF) is added a suitable peptide coupling reagent, for example o-(7-azabenzotriazol-1-yl)-N,N,N',N'-tetramethyluronium hexafluorophosphate (HATU) followed by a suitable hindered base, for example N,N-di-iso-propylethylamine (DIPEA), and the reaction stirred at a suitable temperature, for example ambient temperature, for a suitable period of time, for example 15-30 minutes. A compound of formula (X) is added in a suitable solvent, for example DMF and the reaction stirred at a suitable temperature, for example ambient temperature, for a suitable period of time, for example 3-8 hours. Water and a suitable organic solvent, for example diethyl ether are added and the layers separated. The aqueous layer is extracted with further organic solvent, for example diethyl ether and the combined organic layers washed with water, dried, for example using anhydrous sodium sulfate, and concentrated under reduced pressure. The crude product may be purified for example by column chromatography.

A compound of formula (III) may be prepared by reduction of a compound of formula (VIII):

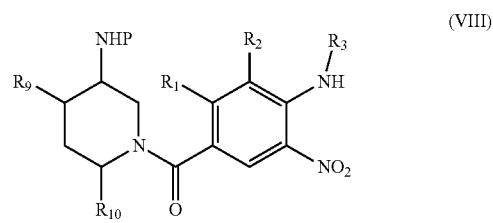

(VIII)

wherein $R_1$, $R_2$, $R_3$, $R_9$, $R_{10}$, and P are as hereinbefore defined.

For example, a compound of formula (VIII) is dissolved in a suitable solvent, for example ethanol and added to a flushed hydrogenation flask containing a suitable catalyst, for example palladium on carbon. The resultant mixture is flushed with nitrogen/vacuum, then stirred under an atmosphere of hydrogen at a suitable temperature, for example ambient temperature, for a suitable period of time, for example 24 hours. The reaction mixture is then flushed from the hydrogen atmosphere with nitrogen/vacuum. To this solution, Celite is added and the mixture stirred for a suitable period of time, for example 2-5 minutes, then filtered under reduced pressure. The solution is concentrated under reduced pressure to give a crude product that may be purified by, for example, chromatography.

A compound of formula (VIII) may be prepared by reaction of a compound of formula (IX):

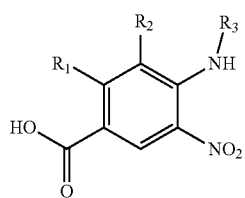

(IX)

wherein $R_1$, $R_2$, and $R_3$ are as hereinbefore defined, with a compound of formula (X):

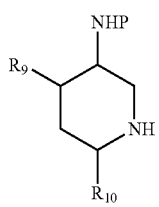

wherein $R_9$, $R_{10}$, and P are as hereinbefore defined.

For example, to a solution of a compound of formula (X), a compound of formula (IX) and and a suitable peptide coupling reagent, for example o-(7-azabenzotriazol-1-yl)-N,N,N',N'-tetramethyluronium hexafluorophosphate (HATU) in a suitable solvent, for example N,N-dimethylformamide, is added a suitable hindered base, for example N,N-di-iso-propylethylamine (DIPEA) and the reaction stirred at a suitable temperature, for example ambient temperature, for a suitable period of time, for example 12-18 hours. Water and a suitable organic solvent, for example diethyl ether, are added and the layers separated. The aqueous layer is extracted with further organic solvent, for example diethyl ether, and the combined organic layers washed with water, dried, for example over anhydrous sodium sulfate, and concentrated in vacuo. The crude product may be purified using conventional techniques such as chromatography.

A compound of formula (IX) may be prepared by hydrolysis of a compound of formula (XI):

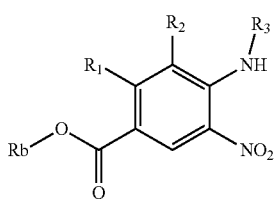

wherein Rb is $C_{1-6}$alkyl and $R_1$, $R_2$, $R_3$ are as hereinbefore defined.

For example, a compound of formula (XI) is dissolved in a suitable solvent, for example a 1:1 v/v ratio of tetrahydrofuran and water. To this solution is added a suitable base, for example lithium hydroxide, and the reaction stirred at a suitable temperature, for example ambient temperature, for a suitable period of time, for example 12-18 hours. The reaction mixture was cooled to a suitable temperature, for example 0° C. and acidified by the addition of a suitable aqueous mineral acid, for example 5M HCl solution, until the pH reaches about 5. The slurry is filtered and the product residue washed with distilled water and dried.

A compound of formula (XI) may be prepared by reaction of a compound of formula (XIV):

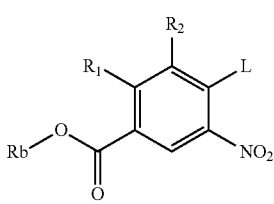

wherein Rb, $R_1$, and $R_2$, are as hereinbefore defined and L is a suitable leaving group, for example a halo group, for example chloro, with a compound of formula (XIII):

$$R_3—NH_2 \quad (XIII)$$

wherein $R_3$ is as hereinbefore defined.

For example, a compound of formula (XIV) is dissolved in a suitable solvent, for example N,N-dimethylformamide (DMF) and cooled to a suitable temperature, for example about 0° C. in an ice/water bath. A solution of a compound of formula (XIII) in a suitable solvent, for example tetrahydrofuran, is added dropwise with vigorous stirring and the mixture flushed with nitrogen and heated to a suitable temperature, for example 70-90° C. for a suitable period of time, for example 3 hours. The mixture is allowed to cool to a suitable temperature, for example ambient temperature, over a suitable period of time, for example 60-70 hours. The reaction mixture is diluted with water and filtered under reduced pressure to give a compound of formula (XI).

A compound of formula (IV) wherein $R_4$ is other than hydrogen may be prepared by hydrolysis of a compound of formula (V):

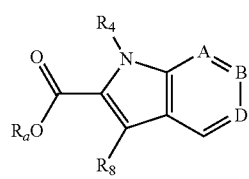

wherein $R_a$ is $C_{1-6}$alkyl, $R_4$, is other than hydrogen, and A, B, D, and $R_8$ are as hereinbefore defined.

For example, to a mixture of a compound of formula (V) in a suitable solvent, for example a mixture of methanol, tetrahydrofuran (THF), and water, is added a suitable base, for example lithium hydroxide monohydrate, and the mixture stirred at a suitable temperature, for example ambient temperature under an inert atmosphere, for example an atmosphere of nitrogen, for a suitable period of time, for example 1-2 hours. The mixture is concentrated under reduced pressure, then treated with a suitable aqueous mineral acid, for example 2N HCl, and the product isolated by filtration.

A compound of formula (V) wherein $R_4$ is other than hydrogen may be prepared by alkylation of a compound of formula (IV) wherein $R_4$ is hydrogen i.e. a compound of formula (VI):

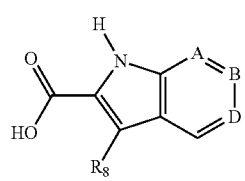

wherein A, B, D, and $R_8$ are as hereinbefore defined.

For example, a suitable organic solvent, for example dimethyl sulfoxide (DMSO) is added to a flask containing a suitable base, for example potassium hydroxide and the mixture stirred under an inert atmosphere, for example an atmosphere of nitrogen, for a suitable period of time, for example 8-12 minutes. A compound of formula (VI) and a suitable alkylating agent, for example bromoethane, is added and the mixture stirred at a suitable temperature, for example ambient temperature, under the inert atmosphere for a suitable period of time, for example 18-24 hours. The reaction is quenched by the slow careful addition of water. A suitable organic solvent, for example diethyl ether, is added and the reaction mixture separated into the organic and aqueous layers. The aqueous layer is further extracted with a suitable organic solvent, for example diethyl ether, and the combined organic layers dried, for example by passing through a hydrophobic frit, and concentrated under reduced pressure to give a compound of formula (V) wherein $R_4$ is other than hydrogen.

A compound of formula (II) may also be prepared by condensation with a compound of formula (VII). Accordingly, in a further aspect, there is provided a process for the preparation of a compound of formula (II) by reaction of a compound of formula (VII):

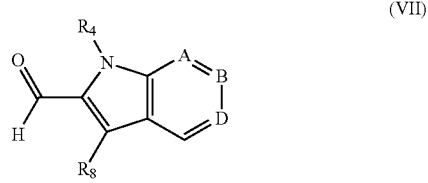

(VII)

wherein $R_4$, A, B, D, and $R_8$, are as hereinbefore defined, with a compound of formula (VIII) as hereinbefore defined.

For example, to a solution of a compound of formula (VIII) and a compound of formula (VII) in a suitable solvent, for example ethanol, is added portionwise a solution of a suitable reducing agent, for example sodium dithionite in a suitable solvent, for example water. The mixture is flushed with, for example nitrogen, then heated at a suitable temperature, for example 100° C., for a suitable period of time, for example 12-18 hours. The reaction mixture is concentrated under vacuum then diluted with a suitable solvent, for example dichloromethane and water added. The organic layer is collected and the aqueous layer washed with further solvent, for example dichloromethane. The organic layers are combined, back washed with water, collected, dried with, for example anhydrous sodium sulfate, filtered through a hydrophobic frit and concentrated under vacuum to yield the crude product. The crude product may be purified by conventional means, for example chromatography.

A compound of formula (VII) wherein $R_4$ is other than hydrogen may be prepared by reaction of a compound of formula (VII) wherein $R_4$ is hydrogen by reaction with a compound of formula (XV):

$R_4$-M (XV)

wherein $R_4$ is as hereinbefore defined and M is a suitable leaving group, for example a halo group, for example iodo, or an alkylsulfonyl group, for example trifluoromethanesulfonyl.

For example, to a suspension of compound of formula (VII) wherein $R_4$ is hydrogen and a suitable base, for example caesium carbonate, in a suitable organic medium, for example N,N-dimethylformamide stirred under an inert atmosphere, for example an atmosphere of nitrogen, at a suitable temperature, for example 20° C. is added a compound of formula (XV) dropwise over a suitable period of time, for example 0.5-1 minute. The reaction mixture is stirred at a suitable temperature, for example ambient temperature. for a suitable period of time, for example 1 hour. The reaction mixture is quenched with water, partitioned between a suitable organic solvent, for example dichloromethane, and water. The aqueous phase is extracted with a suitable organic solvent, for example dichloromethane. The organic phase is washed with saturated brine, dried over, for example sodium sulfate, and evaporated in vacuo to give the crude product. The crude product may be purified by conventional means, for example chromatography.

A compound of formula (VII) wherein $R_4$ is hydrogen may be prepared by deprotection of a compound of formula (XVI):

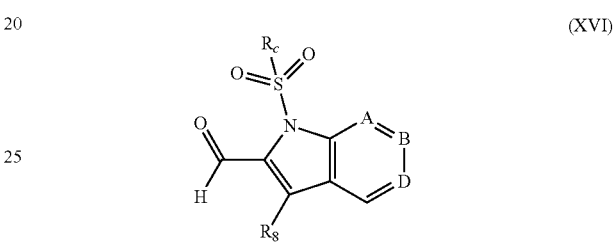

(XVI)

wherein $R_c$ is an aryl group, for example phenyl, and A, B, D, and $R_8$ are as hereinbefore defined.

For example, to a solution of a suitable base, for example potassium hydroxide, in a suitable organic solvent, for example methanol, stirred at a suitable temperature, for example ambient temperature, is added a solution of a compound of formula (XVI) in a suitable solvent, for example methanol, dropwise over a suitable period of time, for example 0.5-1 minute. The mixture is stirred at a suitable temperature, for example ambient temperature, until the starting material is consumed. The reaction mixture is then diluted with water and then a suitable organic solvent, for example dichloromethane is added. The pH is adjusted to 7 with a suitable mineral acid, for example concentrated hydrochloric acid, and extracted with further organic solvent, for example dichloromethane. The organic phase is then washed, dried, and the solvent removed to give a compound of formula (VII).

A compound of formula (XVI) may be prepared from a compound of formula (XVII)

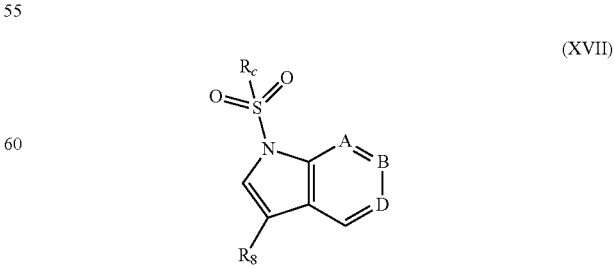

(XVII)

wherein $R_c$, A, B, D, and $R_8$ are as hereinbefore defined.

For example, to a solution of a suitable organic base, for example diisopropylamine, in a suitable anhydrous organic solvent, for example anhydrous tetrahydrofuran, stirred under an inert atmosphere, for example an atmosphere of nitrogen, at a suitable temperature, for example −78° C. is added a suitable base, for example n-butyllithium, over a suitable period of time, for example 10-20 minutes. The reaction mixture is stirred at a suitable temperature, for example −78° C. for a suitable period of time, for example 20-40 minutes, then warmed to a suitable temperature, for example ambient temperature, and stirred for a suitable period of time, for example 45-90 minutes. To this solution of lithium diisopropylamide in a suitable anhydrous solvent, for example anhydrous tetrahydrofuran, stirred under an inert atmosphere, for example an atmosphere of nitrogen, at a suitable temperature, for example −30° C., is added a solution of a compound of formula (XVII) and a suitable base, for example tetramethylethylenediamine in a suitable organic solvent, for example tetrahydrofuran, dropwise over a suitable period of time, for example 10-20 minutes. The reaction mixture is stirred at a suitable temperature, for example −30° C., for a suitable period of time, for example 2-3 hours, then a suitable organic solvent, for example N,N-dimethylformamide is added dropwise over a suitable period of time, for example 1 minute. The reaction mixture is stirred at at a suitable temperature, for example −30° C. for a further suitable period of time, for example 1.5-3 hours. The reaction mixture is quenched with water and partitioned between a suitable organic solvent, for example dichloromethane, and water. The organic phase is washed, dried, and evaporated to give a crude compound of formula (XVI), which may be purified by conventional means, for example, recrystallisation.

A compound of formula (XVII) may be prepared by reaction of a compound of formula (XVIII):

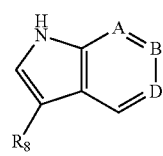

(XVIII)

wherein A, B, D, and $R_8$ are as hereinbefore defined, with a compound of formula (XIX):

$R_cSO_2$-Q (XIX)

wherein Rc is as hereinbefore defined and Q is a suitable leaving group, for example a halo group, for example chloro.

For example, to a solution of a compound of formula (XVIII) in a suitable organic solvent, for example tetrahydrofuran, is added a suitable base, for example sodium hydride portionwise over a suitable period of time, for example 5 minutes, under an inert atmosphere, for example an atmosphere of nitrogen, at a suitable temperature, for example 0° C. The reaction mixture is stirred at a suitable temperature, for example 0° C. for a suitable period of time, for example 30-45 minutes, then a compound of formula (XIX) is added dropwise under an inert atmosphere, for example an atmosphere of nitrogen, at a suitable temperature, for example 0° C., then stirred for a suitable period of time, for example 1.5-3 hours at a suitable temperature, for example ambient temperature, until the starting material had been completely consumed. The mixture is poured into water and extracted with a suitable organic solvent, for example ethyl acetate. The organic phase is washed, dried, and evaporated to give a crude compound of formula (XVII), which may be purified by conventional means, for example, recrystallisation.

A compound of formula (XX) may be prepared by hydrolysis of a compound of formula (XXI):

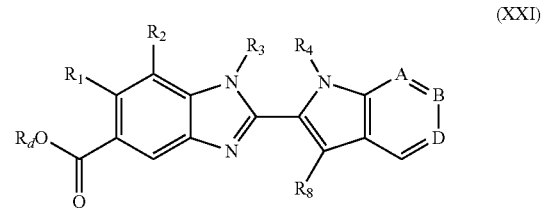

(XXI)

wherein $R_1$, $R_2$, $R_3$, $R_4$, A, B, D, and $R_8$ are as hereinbefore defined and $R_d$ is an alkyl group, for example $C_{1-6}$alkyl, For example, a compound of formula (XXI) is dissolved in a suitable solvent, for example a mixture of a suitable organic solvent and water, for example a mixture of tetrahydrofuran (THF) and water, for example in a 1:1 ratio. To this is added a suitable base, for example lithium hydroxide anhydrous and the reaction stirred at a suitable temperature, for example ambient temperature, for a suitable period of time, for example 15-24 hours. The reaction mixture is then neutralised by the addition of a suitable acid, for example 2M hydrochloric acid. The suspension is filtered and the residue washed with water and dried in vacuo to afford a compound of formula (XX).

A compound of formula (XXI) may be prepared by reaction of a compound of formula (VII) as hereinbefore defined with a compound of formula (XI) as hereinbefore defined.

For example, a solution of a suitable reducing agent, for example sodium hydrosulfite, in a suitable solvent, for example water is added to a suspension of a compound of formula (XI) and a compound of formula (VII) in a suitable medium, for example; ethanol. The reaction mixture is heated, for example in a microwave oven, to a suitable temperature, for example, 90-110° C. for a suitable period of time, for example 3-6 hours. The reaction mixture is diluted with a suitable solvent, for example dichloromethane, dried, for example using anhydrous sodium sulfate, filtered and concentrated under reduced pressure to afford the crude product. The crude product may be purified by, for example, column chromatography.

A compound of formula (X) wherein $R_9$ is hydroxy may be prepared by hydrogenolysis of a compound of formula (XXII):

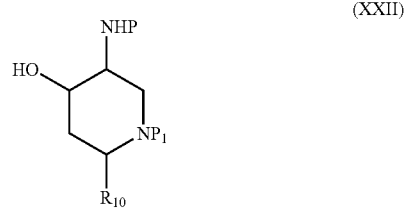

(XXII)

wherein P and $R_{10}$ are as hereinbefore defined and $P_1$ is a protecting group, for example a carboxybenzyl group.

For example, a solution of a compound of formula (XXII) in a suitable solvent, for example ethanol is added to a hydrogenation flask containing a suitable catalyst, for example 10% palladium on carbon, under an inert atmosphere, for example an atmosphere of nitrogen. The flask is then evacuated and back-filled with hydrogen. The system is closed and the mixture allowed to stir under an atmosphere of hydrogen for a suitable period of time, for example 12-18 hours. The reaction mixture was filtered and washed with a suitable solvent, for example ethanol, followed by a further solvent wash with, for example ethyl acetate. The combined filtrate is concentrated under reduced pressure to afford a compound of formula (X).

A compound of formula (XXII) wherein the —OH group and —NHP groups are cis with respect to each other may be prepared by hydrolysis of a compound of formula (XXIII):

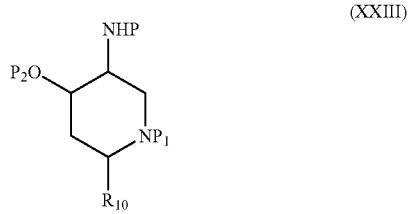

(XXIII)

wherein P and $P_1$, and $R_{10}$ are as hereinbefore defined and $P_2$ is a suitable protecting group, for example a benzoyl group.

For example, a solution of a suitable base, for example potassium carbonate in a suitable solvent, for example water is added to a solution of a compound of formula (XXIII) in a suitable solvent, for example ethanol, and the mixture stirred at a suitable temperature, for example 60-70° C. for 18-24 hours. The reaction mixture is concentrated under reduced pressure, diluted with water, and extracted using a suitable solvent, for example dichloromethane. The organic extracts are combined and dried using, for example anhydrous sodium sulfate, and concentrated under reduced pressure to afford the crude compound of formula (XXII) wherein the —OH group and —NHP groups are cis with respect to each other. The crude product may be purified by, for example, column chromatography.

A compound of formula (XXIII) wherein the $P_2O$— and —NHP groups are cis with respect to each other may be prepared from a compound of formula (XXII) where the HO— and —NHP groups are trans with respect to each other via the Mitsunobu reaction.

For example, to a solution of triphenylphosphine in a suitable solvent, for example tetrahydrofuran is added di-iso-propyl azodicarboxylate and the mixture was stirred at a suitable temperature, for example in an ice-water bath for a suitable period of time, for example 10-15 minutes and then allowed to warm to ambient temperature. A compound of formula (XXII) where the HO— and —NHP groups are trans with respect to each other in a suitable solvent, for example tetrahydrofuran, is added followed by a suitable acid, for example benzoic acid. The reaction is stirred at a suitable temperature, for example ambient temperature, for a suitable period of time, for example 18-24 hours. The reaction mixture is then concentrated, for example under reduced pressure. The crude product is then purified using, for example, column chromatography.

A compound of formula (XXII) wherein the —OH group and —NHP groups are trans with respect to each other may be prepared by hydrolysis of a compound of formula (XXIV):

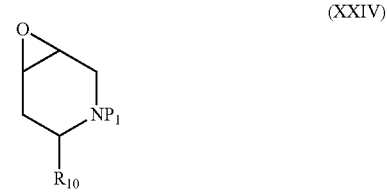

(XXIV)

wherein $P_1$ and $R_{10}$ are as hereinbefore defined.

A solution of a compound of formula (XIV) in a suitable basic solvent mixture, for example a mixture of aqueous ammonium hydroxide solution and a suitable organic solvent, for example ethanol is stirred at a suitable temperature, for example 60-80° C. for a suitable period of time, for example 4-6 hours. The reaction mixture is concentrated under reduced pressure, diluted with brine, and the organic layer extracted into a suitable solvent, for example dichloromethane. The combined organic layers are dried using, for example anhydrous sodium sulfate, and concentrated under reduced pressure to give the intermediate primary amine. The residue is diluted with a suitable solvent, for example dichloromethane and a suitable base, for example triethylamine, and the precursor to a suitable protecting group, for example di-tert-butyl dicarbonate. The reaction is allowed to stir for a suitable period of time, for example 1-3 hours, quenched with, for example, saturated aqueous ammonium chloride solution, and the layers separated. The combined organic layers are dried using, for example, a hydrophobic frit and the solvent was removed under reduced pressure to yield a compound of formula (XXII) wherein the —OH group and —NHP groups are trans with respect to each other.

A compound of formula (XXIV) may be prepared by reaction of a suitable peracid, for example 3-chlorobenzoperoxoic acid, with a compound of formula (XXV):

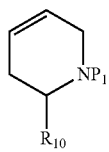

(XXV)

wherein P₁ and R₁₀ are as hereinbefore defined.

For example, a suitable peracid, for example 3-chlorobenzoperoxoic acid, is added portionwise under an inert atmosphere, for example an atmosphere of nitrogen, to a stirred solution of a compound of formula (XXV) (available, for example, from Fluorochem, Hadfield, Derbyshire, UK) in a suitable anhydrous solvent, for example anhydrous dichloromethane, under cooling, for example using an ice bath. The resulting mixture is allowed to reach ambient temperature and stirred for a suitable period of time, for example 12-24 hours. Water is added to the reaction mixture and the layers partitioned. The organic layer is added to a stirred solution of a reducing agent for example an aqueous solution of sodium metabisulfite to destroy excess peracid. The layers are separated and aqueous layer washed with a suitable solvent, for example dichloromethane. The combined organic layers are then dried, for example using anhydrous sodium sulfate, and concentrated under reduced pressure to afford the crude product, which may be purified by chromatography.

The preparations of compounds of formula (I) are summarised in the following synthetic schemes:

Scheme 1

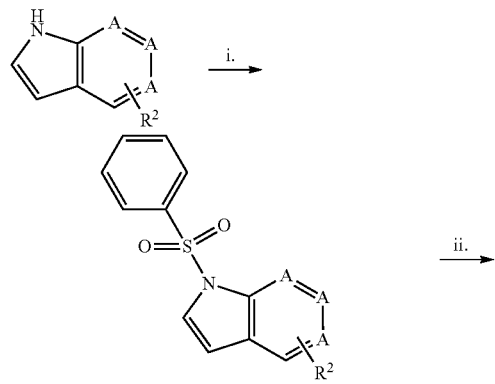

i. NaH, PhSO₂Cl, DMF;
ii. nBuLi / iPr2NH, DMF, TMEDA, THF;
iii. KOH / MeOH
Where A = C, CH or N, provided that at least one A is N.

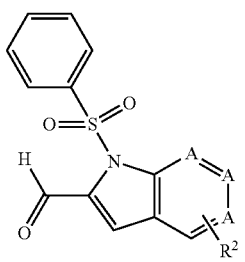

Scheme 2

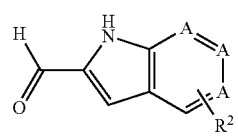

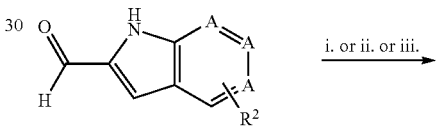

i. NaH, R¹X, DMF;
ii. M₂CO₃, R¹X, DMF;
iii. KOH, R¹X, DMSO.

Scheme 3

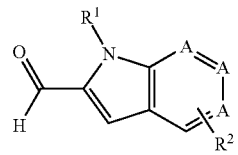

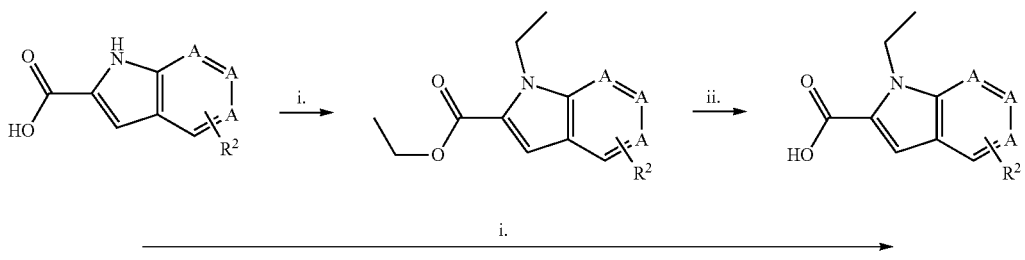

i. KOH, EtBr, DMSO
ii. aq. LiOH, MeOH, thf

Scheme 4
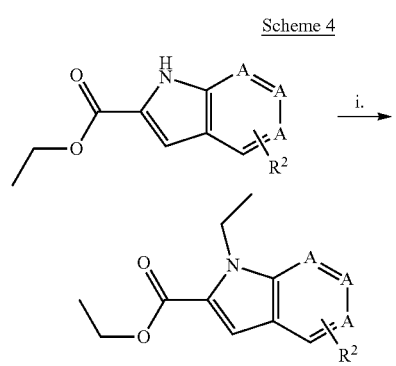
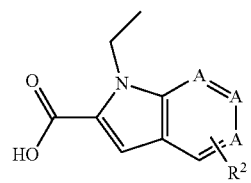
i. KOH, EtBr, DMSO
ii. aq. LiOH, MeOH, thf
Scheme 5
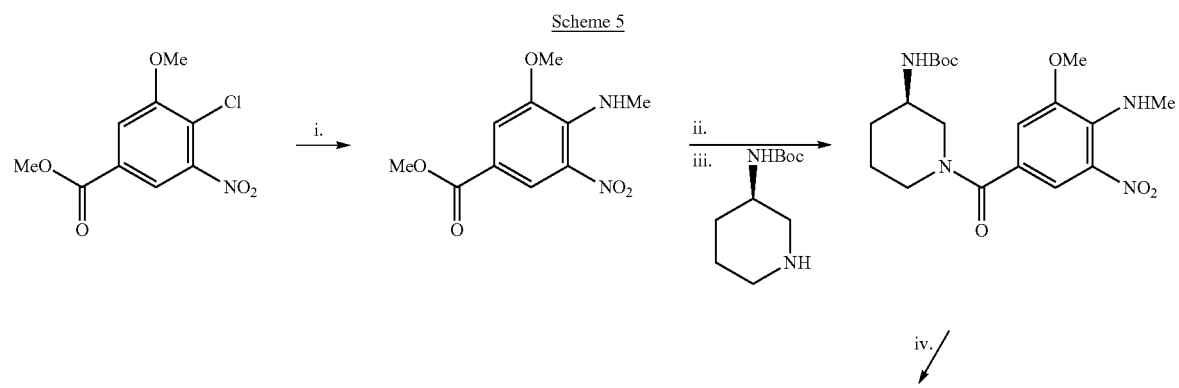
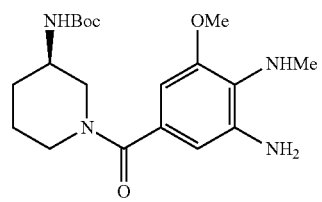
i. MeNH2 (thf) / DMF;
ii. LiOH, THF / H2O;
iii. HATU, DIPEA, DMF
iv. H2, 10% Pd/C, EtOH
Scheme 6
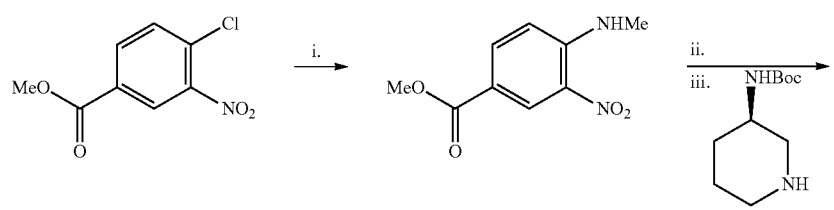

27 -continued 28
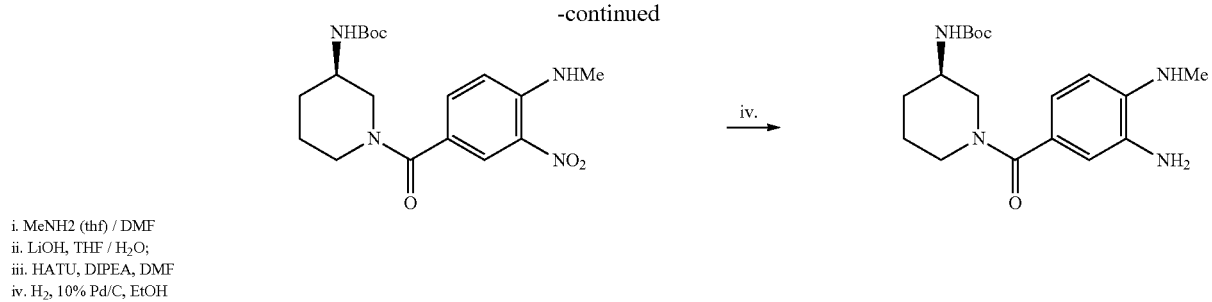
i. MeNH2 (thf) / DMF
ii. LiOH, THF / H₂O;
iii. HATU, DIPEA, DMF
iv. H₂, 10% Pd/C, EtOH
Scheme 7
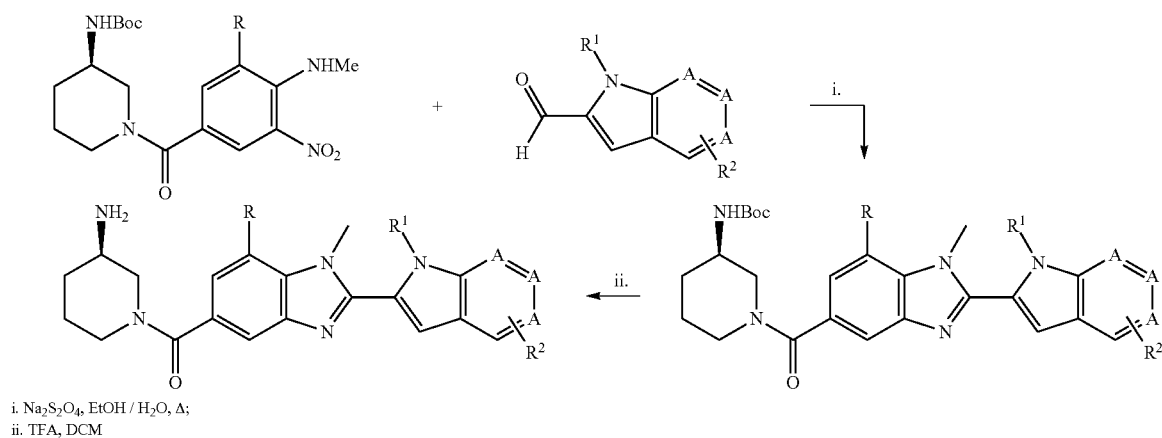
i. Na₂S₂O₄, EtOH / H₂O, Δ;
ii. TFA, DCM
Scheme 8
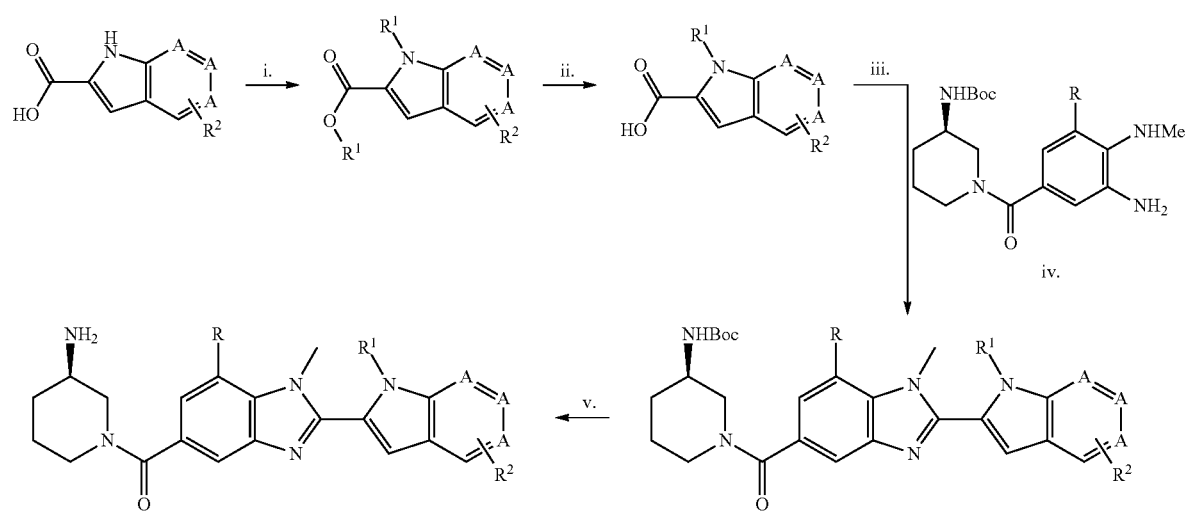
i. K₂CO₃, R¹X, DMF or KOH, R¹X, DMSO;
ii. LiOH, THH / H₂O;
iii. HATU, DIPEA, DMF;
iv. Toluene / AcOH, Δ;
v. TFA, DCM Scheme 9
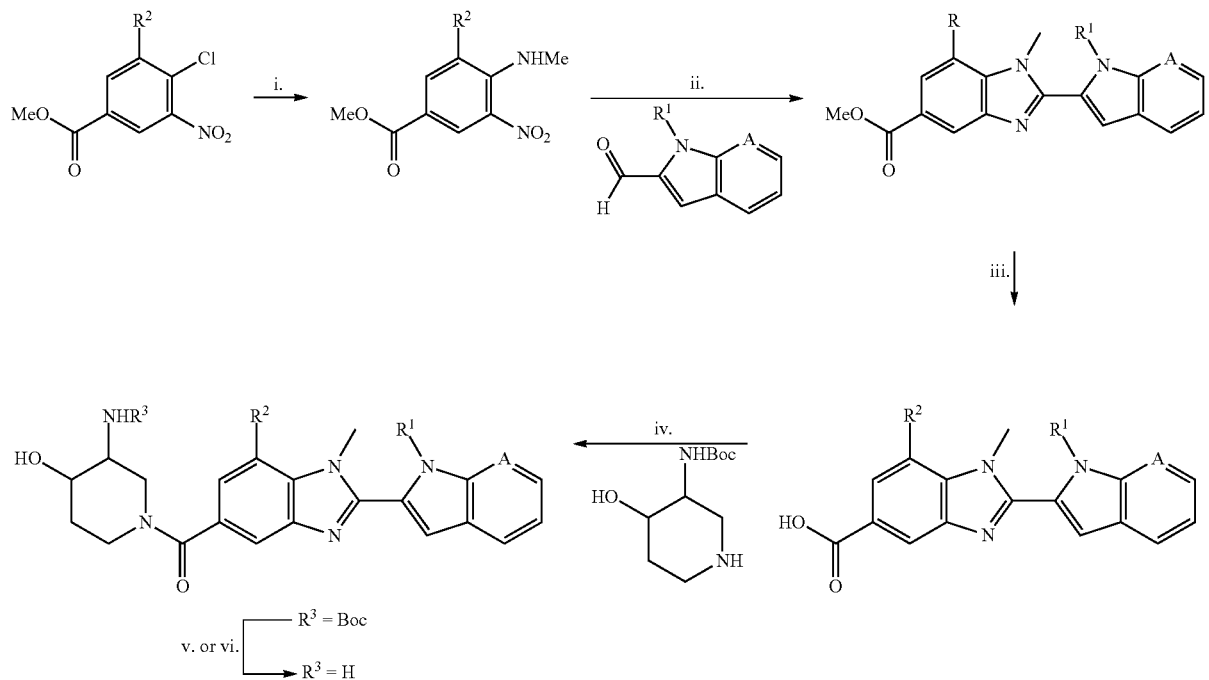
i. MeNH₂, (THF) / DMF;
ii. Na₂S₂O₄, EtOH / H₂O;
iii. LiOH, THF / H₂O;
iv. HATU, DIPEA, DMF;
v. TFA, DCM;
vi. 4N HCl in 1,4-dioxane
Where A = CH or N; $R^1$ = CH₂cPr, Et or CH₂CF₃; $R^2$ = H or OMe.
Scheme 10
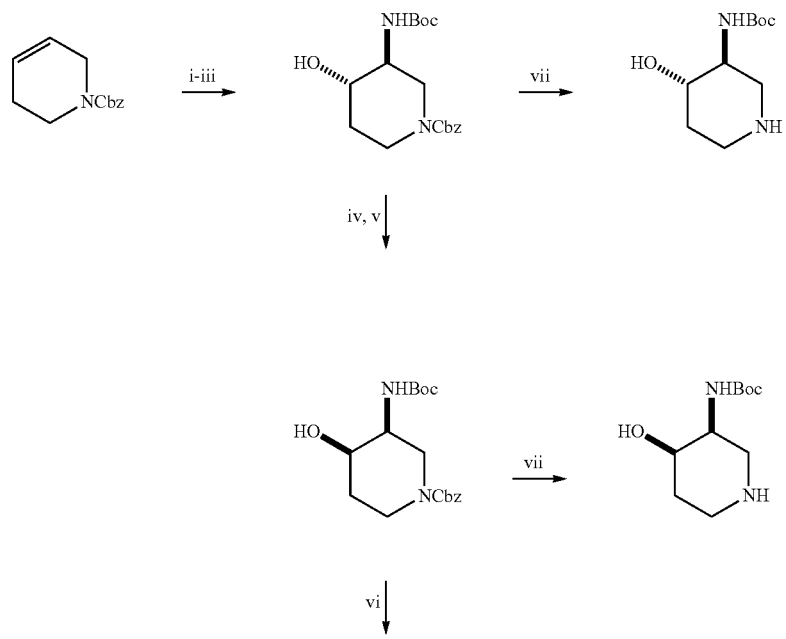

31 32
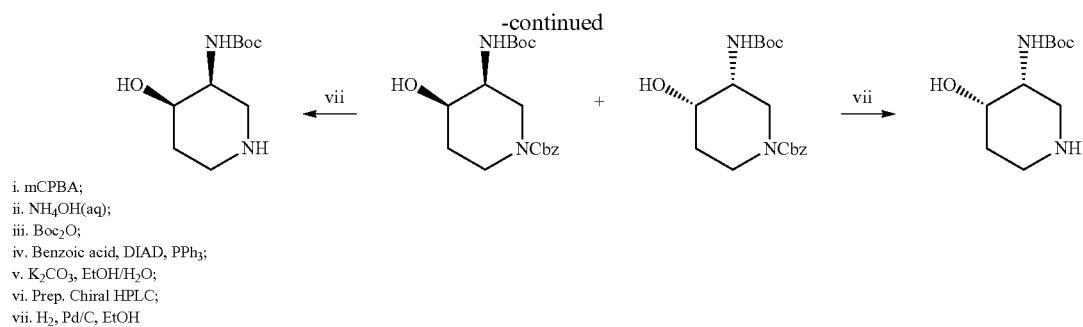
i. mCPBA;
ii. NH$_4$OH(aq);
iii. Boc$_2$O;
iv. Benzoic acid, DIAD, PPh$_3$;
v. K$_2$CO$_3$, EtOH/H$_2$O;
vi. Prep. Chiral HPLC;
vii. H$_2$, Pd/C, EtOH
Scheme 11
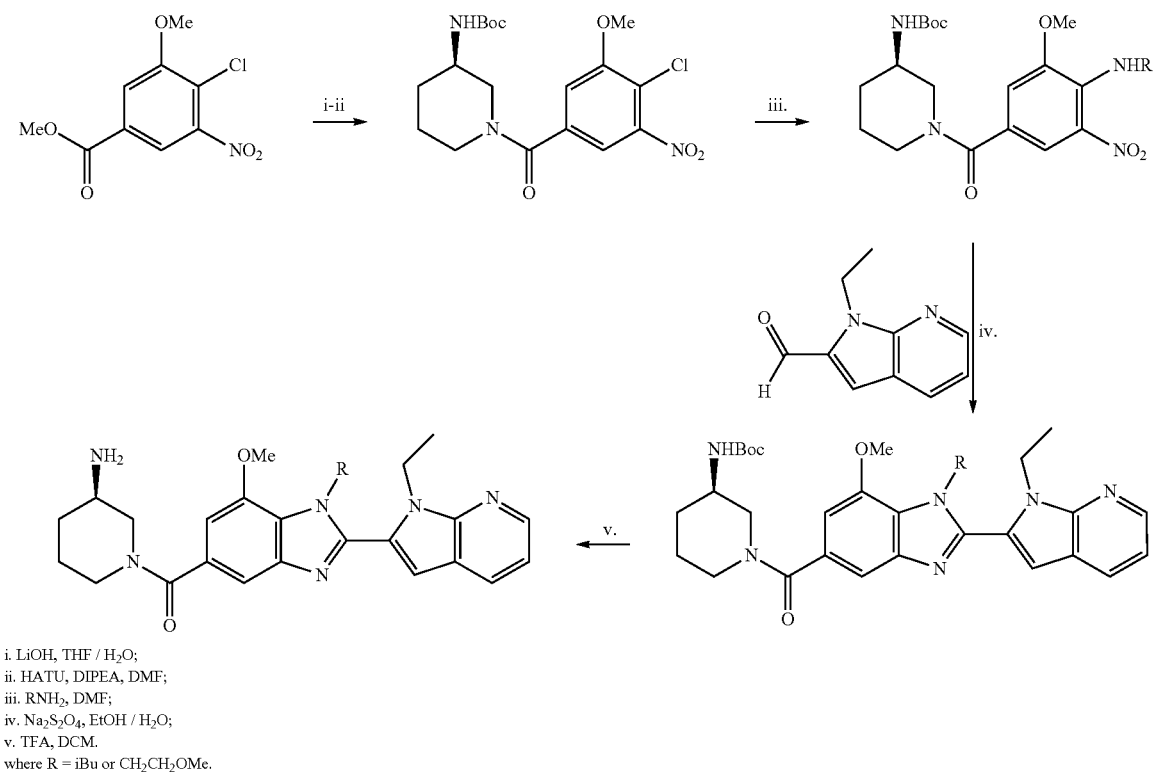
i. LiOH, THF / H$_2$O;
ii. HATU, DIPEA, DMF;
iii. RNH$_2$, DMF;
iv. Na$_2$S$_2$O$_4$, EtOH / H$_2$O;
v. TFA, DCM.
where R = iBu or CH$_2$CH$_2$OMe.
Scheme 12
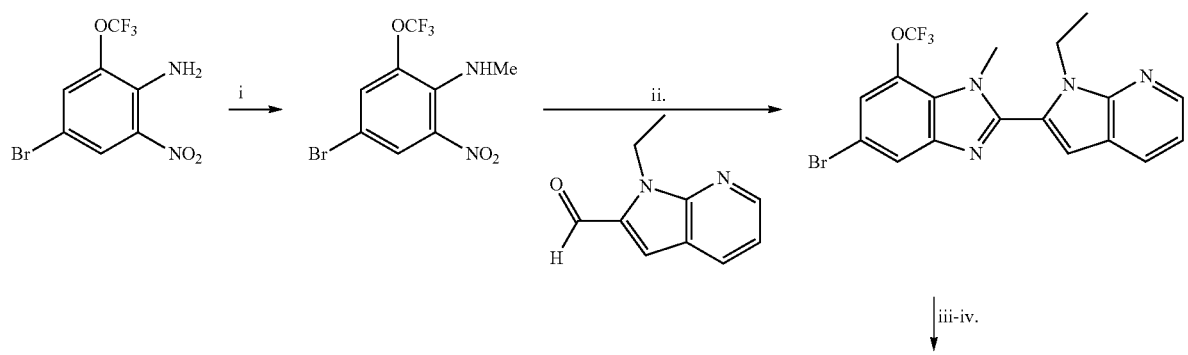

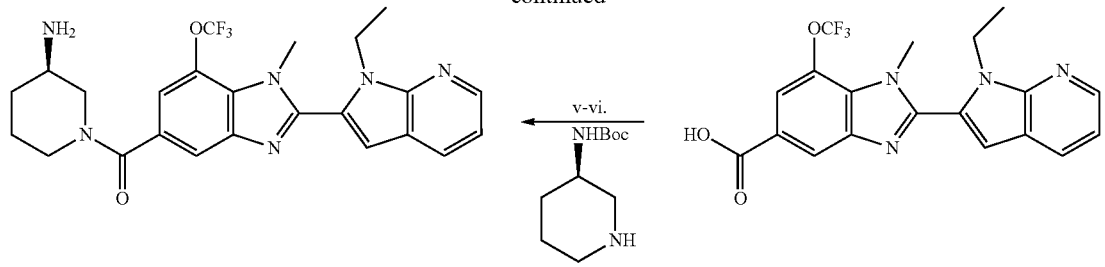

i. Cs₂CO₃, MeI, DMF;
ii. Na₂S₂O₄, EtOH / H₂O;
iii. Mo(CO)₆, trans-bis(acetato)bis[o-(di-o-tolylphosphino)benzyl]dipalladium(II), DIPEA, DMAP, MeOH, 1-4-dioxane;
iv. LiOH, THF / H₂O;
v. HATU, DIPEA, DMF;
v. TFA, DCM.

Compounds of formulae (VI), (XIII), (X), (XIV), (XV), (XVIII), (XIX), and (XXV) are either known in the literature or are commercially available, for example from Sigma-Aldrich, UK, Apollo Scientific Limited, Alfa Aesar, Shanghai Haoyuan Chemexpress Co. Ltd, Activate Scientific GmbH, Lancaster Synthesis Ltd, Fluorochem, Hadfield, Derbyshire, UK, or may be prepared by analogy with known procedures, for example those disclosed in standard reference texts of synthetic methodology such as *J. March, Advanced Organic Chemistry, 6th Edition* (2007), Wiley-Blackwell, or *Comprehensive Organic Synthesis* (Trost B. M. and Fleming I., (Eds.), Pergamon Press, 1991), each incorporated herein by reference as it relates to such procedures.

Examples of other protecting groups that may be employed in the synthetic routes described herein and the means for their removal can be found in *T. W. Greene 'Protective Groups in Organic Synthesis', 4th Edition*, J. Wiley and Sons, 2006, incorporated herein by reference as it relates to such procedures.

For any of the hereinbefore described reactions or processes, conventional methods of heating and cooling may be employed, for example temperature-regulated oil-baths or temperature-regulated hot-blocks, and ice/salt baths or dry ice/acetone baths respectively. Conventional methods of isolation, for example extraction from or into aqueous or non-aqueous solvents may be used. Conventional methods of drying organic solvents, solutions, or extracts, such as shaking with anhydrous magnesium sulfate, or anhydrous sodium sulfate, or passing through a hydrophobic frit, may be employed. Conventional methods of purification, for example crystallisation and chromatography, for example silica chromatography or reverse-phase chromatography, may be used as required. Crystallisation may be performed using conventional solvents such as ethyl acetate, methanol, ethanol, or butanol, or aqueous mixtures thereof. It will be appreciated that specific reaction times and temperatures may typically be determined by reaction-monitoring techniques, for example thin-layer chromatography and LC-MS.

Where appropriate individual isomeric forms of the compounds of the invention may be prepared as individual isomers using conventional procedures such as the fractional crystallisation of diastereoisomeric derivatives or chiral high performance liquid chromatography (chiral HPLC).

The absolute stereochemistry of compounds may be determined using conventional methods, such as X-ray crystallography or VCD (vibrational circular dichroism) analysis.

Methods of Use

The compounds of the invention are inhibitors of PAD4. Compounds which inhibit PAD4 may be useful in the treatment of various disorders, for example rheumatoid arthritis, vasculitis, systemic lupus erythematosus, ulcerative colitis, cancer, cystic fibrosis, asthma, cutaneous lupus erythematosis, and psoriasis.

The methods of treatment of the invention comprise administering a safe and effective amount of a compound of formula (I), or a pharmaceutically acceptable salt thereof, to a patient in need thereof. Individual embodiments of the invention include methods of treating any one of the above-mentioned disorders by administering a safe and effective amount of a compound of formula (I), or a pharmaceutically acceptable salt thereof, to a patient in need thereof.

As used herein, 'treat' in reference to a disorder means: (1) to ameliorate or prevent the disorder or one or more of the biological manifestations of the disorder, (2) to interfere with (a). one or more points in the biological cascade that leads to or is responsible for the disorder, or (b). one or more of the biological manifestations of the disorder, (3) to alleviate one or more of the symptoms or effects associated with the disorder, or (4) to slow the progression of the disorder or one or more of the biological manifestations of the disorder.

As indicated above, 'treatment' of a disorder includes prevention of the disorder. It will be appreciated that 'prevention' is not an absolute term. In medicine, 'prevention' is understood to refer to the prophylactic administration of a drug to substantially diminish the likelihood or severity of a disorder or biological manifestation thereof, or to delay the onset of such disorder or biological manifestation thereof.

As used herein, 'safe and effective amount' in reference to a compound of formula (I), or a pharmaceutically acceptable salt thereof, or other pharmaceutically-active agent means an amount of the compound sufficient to treat the patient's condition but low enough to avoid serious side effects (at a reasonable benefit/risk ratio) within the scope of sound medical judgment. A safe and effective amount of a compound will vary with the particular compound chosen (for example, the potency, efficacy, and half-life of the compound will be considered); the route of administration chosen; the disorder being treated; the severity of the disorder being treated; the age, size, weight, and physical condition of the patient being treated; the medical history of the patient to be treated; the duration of the treatment; the nature of concurrent therapy; the desired therapeutic effect; and like factors, but can nevertheless be routinely determined by the skilled artisan.

As used herein, 'patient' refers to a human (including adults and children) or other animal. In one embodiment, 'patient' refers to a human.

The compounds of formula (I), or pharmaceutically acceptable salts thereof, may be administered by any suitable route of administration, including both systemic administration and topical administration. Systemic administration includes oral administration, parenteral administration, transdermal administration and rectal administration. Parenteral administration refers to routes of administration other than enteral or transdermal, and is typically by injection or infusion. Parenteral administration includes intravenous, intramuscular, and subcutaneous injection or infusion. Topical administration includes application to the skin as well as intraocular, otic, intravaginal, inhaled and intranasal administration. Inhalation refers to administration into the patient's lungs whether inhaled through the mouth or through the nasal passages. In one embodiment, the compounds of formula (I) or pharmaceutically acceptable salts thereof may be administered orally. In another embodiment, the compounds of formula (I) or pharmaceutically acceptable salts thereof may be administered topically. In another embodiment, the compounds of formula (I) or pharmaceutically acceptable salts thereof may be administered by inhalation. In a further embodiment, the compounds of formula (I) or pharmaceutically acceptable salts thereof may be administered intranasally.

The compounds of formula (I) or pharmaceutically acceptable salts thereof may be administered once or according to a dosing regimen wherein a number of doses are administered at varying intervals of time for a given period of time. For example, doses may be administered one, two, three, or four times per day. In one embodiment, a dose is administered once per day. In a further embodiment, a dose is administered twice per day. Doses may be administered until the desired therapeutic effect is achieved or indefinitely to maintain the desired therapeutic effect. Suitable dosing regimens for a compound of formula (I) or a pharmaceutically acceptable salt thereof depend on the pharmacokinetic properties of that compound, such as absorption, distribution, and half-life, which can be determined by the skilled artisan. In addition, suitable dosing regimens, including the duration such regimens are administered, for a compound of formula (I) or a pharmaceutically acceptable salt thereof depend on the disorder being treated, the severity of the disorder being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

Typical daily dosages may vary depending upon the particular route of administration chosen. Typical daily dosages for oral administration range from 0.1 mg to 10 mg per kg of total body weight, for example from 1 mg to 5 mg per kg of total body weight. For example, daily dosages for oral administration may be from 5 mg to 1 g per patient, such as 5 mg to 500 mg per patient, or 5 mg to 250 mg.

Additionally, the compounds of formula (I) may be administered as prodrugs. As used herein, a 'prodrug' of a compound of formula (I) is a functional derivative of the compound which, upon administration to a patient, eventually liberates the compound of formula (I) in vivo. Administration of a compound of formula (I) as a prodrug may enable the skilled artisan to do one or more of the following: (a) modify the onset of the activity of the compound in vivo; (b) modify the duration of action of the compound in vivo; (c) modify the transportation or distribution of the compound in vivo; (d) modify the solubility of the compound in vivo; and (e) overcome a side effect or other difficulty encountered with the compound. Typical functional derivatives used to prepare prodrugs include modifications of the compound that are chemically or enzymatically cleavable in vivo. Such modifications, which include the preparation of phosphates, amides, esters, thioesters, carbonates, and carbamates, are well known to those skilled in the art.

The invention thus provides a method of treating a disorder mediated by inappropriate PAD4 activity comprising administering a safe and effective amount of a compound of formula (I), or a pharmaceutically acceptable salt thereof, to a patient in need thereof.

In one embodiment, the disorder mediated by inappropriate PAD4 activity is selected from the group consisting of rheumatoid arthritis, vasculitis, systemic lupus erythematosus, ulcerative colitis, cancer, cystic fibrosis, asthma, cutaneous lupus erythematosis, and psoriasis. In a further embodiment, the disorder mediated by inappropriate PAD4 activity is rheumatoid arthritis. In a further embodiment, the disorder mediated by inappropriate PAD4 activity is systemic lupus. In a further embodiment, the disorder mediated by inappropriate PAD4 activity is vasculitis. In a further embodiment, the disorder mediated by inappropriate PAD4 activity is cutaneous lupus erythematosis. In a further embodiment, the disorder mediated by inappropriate PAD4 activity is psoriasis.

In one embodiment there is provided a method of treatment of rheumatoid arthritis, vasculitis, systemic lupus erythematosus, ulcerative colitis, cancer, cystic fibrosis, asthma, cutaneous lupus erythematosis, or psoriasis, which method comprises administering to a human subject in need thereof, a therapeutically effective amount of a compound of formula (I), or a pharmaceutically acceptable salt thereof.

In one embodiment there is provided a method of treatment of rheumatoid arthritis, which method comprises administering to a human subject in need thereof, a therapeutically effective amount of a compound of formula (I), or a pharmaceutically acceptable salt thereof. In one embodiment there is provided a method of treatment of systemic lupus, which method comprises administering to a human subject in need thereof, a therapeutically effective amount of a compound of formula (I), or a pharmaceutically acceptable salt thereof. In one embodiment there is provided a method of treatment of vasculitis, which method comprises administering to a human subject in need thereof, a therapeutically effective amount of a compound of formula (I), or a pharmaceutically acceptable salt thereof. In one embodiment there is provided a method of treatment of cutaneous lupus erythematosis, which method comprises administering to a human subject in need thereof, a therapeutically effective amount of a compound of formula (I), or a pharmaceutically acceptable salt thereof. In one embodiment there is provided a method of treatment of psoriasis, which method comprises administering to a human subject in need thereof, a therapeutically effective amount of a compound of formula (I), or a pharmaceutically acceptable salt thereof.

In one embodiment, the invention provides a compound of formula (I), or a pharmaceutically acceptable salt thereof, for use in therapy. In another embodiment, the invention provides a compound of formula (I), or a pharmaceutically acceptable salt thereof, for use in the treatment of a disorder mediated by inappropriate PAD4 activity. In another embodiment, the invention provides a compound of formula (I), or a pharmaceutically acceptable salt thereof, for use in the treatment of rheumatoid arthritis, vasculitis, systemic lupus erythematosus, ulcerative colitis, cancer, cystic fibrosis, asthma, cutaneous lupus erythematosis, or psoriasis. In another embodiment, the invention provides a compound of formula (I), or a pharmaceutically acceptable salt thereof, for use in the treatment of rheumatoid arthritis. In another embodiment, the invention provides a compound of formula (I), or a pharmaceutically acceptable salt thereof, for use in the treatment of systemic lupus. In another embodiment, the invention provides a compound of formula (I), or a pharmaceutically acceptable salt thereof, for use in the treatment of vasculitis. In another embodiment, the invention provides a compound of formula (I), or a pharmaceutically acceptable salt thereof, for use in the treatment of cutaneous lupus erythematosis. In another embodiment, the invention provides a compound of formula (I), or a pharmaceutically acceptable salt thereof, for use in the treatment of psoriasis. In another embodiment, the invention provides the use of a compound of formula (I), or a pharmaceutically acceptable salt thereof, in the manufacture of a medicament for use in the treatment of a disorder mediated by inappropriate PAD4 activity. In another embodiment, the invention provides the use of a compound of formula (I), or a pharmaceutically acceptable salt thereof, in the manufacture of a medicament for use in the treatment of rheumatoid arthritis, vasculitis, systemic lupus erythematosus, ulcerative colitis, cancer, cystic fibrosis, asthma, cutaneous lupus erythematosis, or psoriasis. In another embodiment, the invention provides the use of a compound of formula (I), or a pharmaceutically acceptable salt thereof, in the manufacture of a medicament for use in the treatment of rheumatoid arthritis. In another embodiment, the invention provides the use of a compound of formula (I), or a pharmaceutically acceptable salt thereof, in the manufacture of a medicament for use in the treatment of systemic lupus. In another embodiment, the invention provides the use of a compound of formula (I), or a pharmaceutically acceptable salt thereof, in the manufacture of a medicament for use in the treatment of vasculitis. In another embodiment, the invention provides the use of a compound of formula (I), or a pharmaceutically acceptable salt thereof, in the manufacture of a medicament for use in the treatment of cutaneous lupus erythematosis. In another embodiment, the invention provides the use of a compound of formula (I), or a pharmaceutically acceptable salt thereof, in the manufacture of a medicament for use in the treatment of psoriasis. In a further embodiment, the invention provides a pharmaceutical composition for the treatment or prophylaxis of a disorder mediated by inappropriate PAD4 activity comprising a compound of formula (I) or a pharmaceutically acceptable salt thereof. In a further embodiment, the invention provides a pharmaceutical composition for the treatment or prophylaxis of rheumatoid arthritis, vasculitis, systemic lupus erythematosus, ulcerative colitis, cancer, cystic fibrosis, asthma, cutaneous lupus erythematosis, or psoriasis, comprising a compound of formula (I) or a pharmaceutically acceptable salt thereof. In a further embodiment, the invention provides a pharmaceutical composition for the treatment or prophylaxis of rheumatoid arthritis comprising a compound of formula (I) or a pharmaceutically acceptable salt thereof. In a further embodiment, the invention provides a pharmaceutical composition for the treatment or prophylaxis of systemic lupus comprising a compound of formula (I) or a pharmaceutically acceptable salt thereof. In a further embodiment, the invention provides a pharmaceutical composition for the treatment or prophylaxis of vasculitis comprising a compound of formula (I) or a pharmaceutically acceptable salt thereof. In a further embodiment, the invention provides a pharmaceutical composition for the treatment or prophylaxis of cutaneous lupus erythematosis comprising a compound of formula (I) or a pharmaceutically acceptable salt thereof. In a further embodiment, the invention provides a pharmaceutical composition for the treatment or prophylaxis of psoriasis comprising a compound of formula (I) or a pharmaceutically acceptable salt thereof Compositions The compounds of formula (I) and pharmaceutically acceptable salts thereof will normally, but not necessarily, be formulated into pharmaceutical compositions prior to administration to a patient. Accordingly, in another aspect there is provided a pharmaceutical composition comprising a compound of formula (I), or a pharmaceutically acceptable salt thereof, and one or more pharmaceutically acceptable excipients. In a further aspect the invention is directed to pharmaceutical compositions for the treatment or prophylaxis of a disorder mediated by inappropriate PAD4 activity comprising a compound of formula (I) or a pharmaceutically acceptable salt thereof.

The pharmaceutical compositions of the invention may be prepared and packaged in bulk form wherein a safe and effective amount of a compound of formula (I) or a pharmaceutically acceptable salt thereof can be extracted and then given to the patient such as with powders or syrups. Alternatively, the pharmaceutical compositions of the invention may be prepared and packaged in unit dosage form wherein each physically discrete unit contains a compound of formula (I) or a pharmaceutically acceptable salt thereof. When prepared in unit dosage form, the pharmaceutical compositions of the invention typically may contain, for example, from 0.25 mg to 1 g, or from 0.5 mg to 500 mg, or from 1 mg to 100 mg, of a compound of formula (I) or a pharmaceutically acceptable salt thereof.

The pharmaceutical compositions of the invention typically contain one compound of formula (I) or a pharmaceutically acceptable salt thereof.

As used herein, 'pharmaceutically acceptable excipient' means a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound of formula (I) or a pharmaceutically acceptable salt thereof when administered to a patient and interactions which would result in pharmaceutical compositions that are not pharmaceutically acceptable are avoided. In addition, each excipient must of course be pharmaceutically acceptable e.g. of sufficiently high purity.

The compound of formula (I) or a pharmaceutically acceptable salt thereof and the pharmaceutically acceptable excipient or excipients will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols, solutions, and dry powders; and (6) topical administration such as creams, ointments, lotions, solutions, pastes, sprays, foams, and gels.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting of the compound or compounds of formula (I) or pharmaceutically acceptable salts thereof once administered to the patient from one organ, or portion of the body, to another organ, or portion of the body. Certain pharmaceutically acceptable excipients may be chosen for their ability to enhance patient compliance.

Suitable pharmaceutically-acceptable excipients include the following types of excipients: Diluents, fillers, binders, disintegrants, lubricants, glidants, granulating agents, coating agents, wetting agents, solvents, co-solvents, suspending agents, emulsifiers, sweetners, flavouring agents, flavour-masking agents, colouring agents, anti-caking agents, humectants, chelating agents, plasticisers, viscosity increasing agents, antioxidants, preservatives, stabilisers, surfactants, and buffering agents. The skilled artisan will appreciate that certain pharmaceutically-acceptable excipients may serve more than one function and may serve alternative functions depending on how much of the excipient is present in the formulation and what other excipients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically-acceptable excipients and may be useful in selecting suitable pharmaceutically-acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in Remington's Pharmaceutical Sciences (Mack Publishing Company).

Accordingly, in another aspect the invention is directed to process for the preparation of a pharmaceutical composition comprising a compound of formula (I) or a pharmaceutically acceptable salt thereof and one or more pharmaceutically-acceptable excipients which comprises mixing the ingredients. A pharmaceutical composition comprising a compound of formula (I) or a pharmaceutically acceptable salt thereof may be prepared by, for example, admixture at ambient temperature and atmospheric pressure.

In one embodiment, the compounds of formula (I) or pharmaceutically acceptable salts thereof will be formulated for oral administration. In another embodiment, the compounds of formula (I) or pharmaceutically acceptable salts thereof will be formulated for inhaled administration. In a further embodiment, the compounds of formula (I) or pharmaceutically acceptable salts thereof will be formulated for intranasal administration.

In one aspect, the invention is directed to a solid oral dosage form such as a tablet or capsule comprising a safe and effective amount of a compound of formula (I) or a pharmaceutically acceptable salt thereof and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmellose, alginic acid, and sodium carboxymethyl cellulose. The oral solid dosage form may further comprise a lubricant. Suitable lubricants include stearic acid, magnesium stearate, calcium stearate, and talc.

Where appropriate, dosage unit formulations for oral administration can be microencapsulated. The composition can also be prepared to prolong or sustain the release as for example by coating or embedding particulate material in polymers, wax or the like.

The compounds of formula (I) or pharmaceutically acceptable salts thereof may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds of formula (I) or pharmaceutically acceptable salts thereof may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

In another aspect, the invention is directed to a liquid oral dosage form. Oral liquids such as solution, syrups and elixirs can be prepared in dosage unit form so that a given quantity contains a predetermined amount of a compound of formula (I) or a pharmaceutically acceptable salt thereof. Syrups can be prepared by dissolving the compound of formula (I) or a pharmaceutically acceptable salt thereof in a suitably flavoured aqueous solution, while elixirs are prepared through the use of a non-toxic alcoholic vehicle. Suspensions can be formulated by dispersing the compound of formula (I) or a pharmaceutically acceptable salt thereof in a non-toxic vehicle. Solubilisers and emulsifiers such as ethoxylated isostearyl alcohols and polyoxy ethylene sorbitol ethers, preservatives, flavour additive such as peppermint oil or natural sweeteners or saccharin or other artificial sweeteners, and the like can also be added.

In another aspect, the invention is directed to a dosage form adapted for administration to a patient by inhalation, for example, as a dry powder, an aerosol, a suspension, or a solution composition.

Dry powder compositions for delivery to the lung by inhalation typically comprise a compound of formula (I) or a pharmaceutically acceptable salt thereof as a finely divided powder together with one or more pharmaceutically-acceptable excipients as finely divided powders. Pharmaceutically-acceptable excipients particularly suited for use in dry powders are known to those skilled in the art and include lactose, starch, mannitol, and mono-, di-, and polysaccharides. The finely divided powder may be prepared by, for example, micronisation and milling. Generally, the size-reduced (eg micronised) compound can be defined by a $D_{50}$ value of about 1 to about 10 microns (for example as measured using laser diffraction).

The dry powder may be administered to the patient via a reservoir dry powder inhaler (RDPI) having a reservoir suitable for storing multiple (un-metered doses) of medicament in dry powder form. RDPIs typically include a means for metering each medicament dose from the reservoir to a delivery position. For example, the metering means may comprise a metering cup, which is movable from a first position where the cup may be filled with medicament from the reservoir to a second position where the metered medicament dose is made available to the patient for inhalation.

Alternatively, the dry powder may be presented in capsules (e.g. gelatin or plastic), cartridges, or blister packs for use in a multi-dose dry powder inhaler (MDPI). MDPIs are inhalers wherein the medicament is comprised within a multi-dose pack containing (or otherwise carrying) multiple defined doses (or parts thereof) of medicament. When the dry powder is presented as a blister pack, it comprises multiple blisters for containment of the medicament in dry powder form. The blisters are typically arranged in regular fashion for ease of release of the medicament therefrom. For example, the blisters may be arranged in a generally circular fashion on a disc-form blister pack, or the blisters may be elongate in form, for example comprising a strip or a tape. Each capsule, cartridge, or blister may, for example, contain between 200 μg-10 mg of the compound of formula (I) or a pharmaceutically acceptable salt thereof.

Aerosols may be formed by suspending or dissolving a compound of formula (I) or a pharmaceutically acceptable salt thereof in a liquified propellant. Suitable propellants include halocarbons, hydrocarbons, and other liquified gases. Representative propellants include: trichlorofluoromethane (propellant 11), dichlorofluoromethane (propellant 12), dichlorotetrafluoroethane (propellant 114), tetrafluoroethane (HFA-134a), 1,1-difluoroethane (HFA-152a), difluoromethane (HFA-32), pentafluoroethane (HFA-12), heptafluoropropane (HFA-227a), perfluoropropane, perfluorobutane, perfluoropentane, butane, isobutane, and pentane. Aerosols comprising a compound of formula (I) or a pharmaceutically acceptable salt thereof will typically be administered to a patient via a metered dose inhaler (MDI). Such devices are known to those skilled in the art.

The aerosol may contain additional pharmaceutically-acceptable excipients typically used with MDIs such as surfactants, lubricants, cosolvents and other excipients to improve the physical stability of the formulation, to improve valve performance, to improve solubility, or to improve taste.

There is thus provided as a further aspect of the invention a pharmaceutical aerosol formulation comprising a compound of formula (I) or a pharmaceutically acceptable salt thereof and a fluorocarbon or hydrogen-containing chlorofluorocarbon as propellant, optionally in combination with a surfactant and/or a cosolvent.

According to another aspect of the invention, there is provided a pharmaceutical aerosol formulation wherein the propellant is selected from 1,1,1,2-tetrafluoroethane, 1,1,1,2,3,3,3-heptafluoro-n-propane and mixtures thereof.

The formulations of the invention may be buffered by the addition of suitable buffering agents.

Capsules and cartridges for use in an inhaler or insufflator, of for example gelatine, may be formulated containing a powder mix for inhalation of a compound of formula (I) or a pharmaceutically acceptable salt thereof and a suitable powder base such as lactose or starch. Each capsule or cartridge may generally contain from 200 μg to 10 mg of the compound of formula (I) or pharmaceutically acceptable salt thereof. Alternatively, the compound of formula (I) or pharmaceutically acceptable salt thereof may be presented without excipients such as lactose.

The proportion of the active compound of formula (I) or pharmaceutically acceptable salt thereof in the local compositions according to the invention depends on the precise type of formulation to be prepared but will generally be within the range of from 0.01 to 10% by weight. Generally, for most types of preparations, the proportion used will be within the range of from 0.05 to 1%, for example from 0.1 to 0.5%.

Aerosol formulations are preferably arranged so that each metered dose or 'puff' of aerosol contains from 20 μg to 10 mg, preferably from 20 μg to 5 mg, more preferably from about 20 μg to 0.5 mg of a compound of formula (I). Administration may be once daily or several times daily, for example 2, 3, 4 or 8 times, giving for example 1, 2 or 3 doses each time. The overall daily dose with an aerosol will be within the range from 100 μg to 10 mg, for example from 200 μg to 5 mg. The overall daily dose and the metered dose delivered by capsules and cartridges in an inhaler or insufflator will generally be double that delivered with aerosol formulations.

In the case of suspension aerosol formulations, the particle size of the particulate (e.g., micronised) drug should be such as to permit inhalation of substantially all the drug into the lungs upon administration of the aerosol formulation and will thus be less than 100 microns, desirably less than 20 microns, and in particular in the range of from 1 to 10 microns, such as from 1 to 5 microns, more preferably from 2 to 3 microns.

The formulations of the invention may be prepared by dispersal or dissolution of the medicament and a compound of formula (I) or a pharmaceutically acceptable salt thereof in the selected propellant in an appropriate container, for example, with the aid of sonication or a high-shear mixer. The process is desirably carried out under controlled humidity conditions.

The chemical and physical stability and the pharmaceutical acceptability of the aerosol formulations according to the invention may be determined by techniques well known to those skilled in the art. Thus, for example, the chemical stability of the components may be determined by HPLC assay, for example, after prolonged storage of the product. Physical stability data may be gained from other conventional analytical techniques such as, for example, by leak testing, by valve delivery assay (average shot weights per actuation), by dose reproducibility assay (active ingredient per actuation) and spray distribution analysis.

The stability of the suspension aerosol formulations according to the invention may be measured by conventional techniques, for example, by measuring flocculation size distribution using a back light scattering instrument or by measuring particle size distribution by cascade impaction or by the 'twin impinger' analytical process. As used herein reference to the 'twin impinger' assay means 'Determination of the deposition of the emitted dose in pressurised inhalations using apparatus A' as defined in British Pharmacopaeia 1988, pages A204-207, Appendix XVII C. Such techniques enable the 'respirable fraction' of the aerosol formulations to be calculated. One method used to calculate the 'respirable fraction' is by reference to 'fine particle fraction' which is the amount of active ingredient collected in the lower impingement chamber per actuation expressed as a percentage of the total amount of active ingredient delivered per actuation using the twin impinger method described above.

The term 'metered dose inhaler' or MDI means a unit comprising a can, a secured cap covering the can and a formulation metering valve situated in the cap. MDI system includes a suitable channelling device. Suitable channelling devices comprise for example, a valve actuator and a cylindrical or cone-like passage through which medicament may be delivered from the filled canister via the metering valve to the nose or mouth of a patient such as a mouthpiece actuator.

MDI canisters generally comprise a container capable of withstanding the vapour pressure of the propellant used such as a plastic or plastic-coated glass bottle or preferably a metal can, for example, aluminium or an alloy thereof which may optionally be anodised, lacquer-coated and/or plastic-coated (for example incorporated herein by reference WO 96/32099 wherein part or all of the internal surfaces are coated with one or more fluorocarbon polymers optionally in combination with one or more non-fluorocarbon polymers), which container is closed with a metering valve. The cap may be secured onto the can via ultrasonic welding, screw fitting or crimping. MDIs taught herein may be prepared by methods of the art (e.g. see Byron, above and WO 96/32099). Preferably the canister is fitted with a cap assembly, wherein a drug-metering valve is situated in the cap, and said cap is crimped in place.

In one embodiment of the invention the metallic internal surface of the can is coated with a fluoropolymer, more preferably blended with a non-fluoropolymer. In another embodiment of the invention the metallic internal surface of the can is coated with a polymer blend of polytetrafluoroethylene (PTFE) and polyethersulfone (PES). In a further embodiment of the invention the whole of the metallic internal surface of the can is coated with a polymer blend of polytetrafluoroethylene (PTFE) and polyethersulfone (PES).

The metering valves are designed to deliver a metered amount of the formulation per actuation and incorporate a gasket to prevent leakage of propellant through the valve. The gasket may comprise any suitable elastomeric material such as, for example, low density polyethylene, chlorobutyl, bromobutyl, EPDM, black and white butadiene-acrylonitrile rubbers, butyl rubber and neoprene. Suitable valves are commercially available from manufacturers well known in the aerosol industry, for example, from Valois, France (e.g. DF10, DF30, DF60), Bespak plc, UK (e.g. BK300, BK357) and 3M-Neotechnic Ltd, UK (e.g. Spraymiser™).

In various embodiments, the MDIs may also be used in conjunction with other structures such as, without limitation, overwrap packages for storing and containing the MDIs, including those described in U.S. Pat. Nos. 6,119,853; 6,179,118; 6,315,112; 6,352,152; 6,390,291; and 6,679,374, as well as dose counter units such as, but not limited to, those described in U.S. Pat. Nos. 6,360,739 and 6,431,168.

Conventional bulk manufacturing methods and machinery well known to those skilled in the art of pharmaceutical aerosol manufacture may be employed for the preparation of large-scale batches for the commercial production of filled canisters. Thus, for example, in one bulk manufacturing method for preparing suspension aerosol formulations a metering valve is crimped onto an aluminium can to form an empty canister. The particulate medicament is added to a charge vessel and liquefied propellant together with the optional excipients is pressure filled through the charge vessel into a manufacturing vessel. The drug suspension is mixed before recirculation to a filling machine and an aliquot of the drug suspension is then filled through the metering valve into the canister. In one example bulk manufacturing method for preparing solution aerosol formulations a metering valve is crimped onto an aluminium can to form an empty canister. The liquefied propellant together with the optional excipients and the dissolved medicament is pressure filled through the charge vessel into a manufacturing vessel.

In an alternative process, an aliquot of the liquefied formulation is added to an open canister under conditions which are sufficiently cold to ensure the formulation does not vaporise, and then a metering valve crimped onto the canister.

Typically, in batches prepared for pharmaceutical use, each filled canister is check-weighed, coded with a batch number and packed into a tray for storage before release testing.

Suspensions and solutions comprising a compound of formula (I) or a pharmaceutically acceptable salt thereof may also be administered to a patient via a nebuliser. The solvent or suspension agent utilized for nebulization may be any pharmaceutically-acceptable liquid such as water, aqueous saline, alcohols or glycols, e.g., ethanol, isopropylalcohol, glycerol, propylene glycol, polyethylene glycol, etc. or mixtures thereof. Saline solutions utilize salts which display little or no pharmacological activity after administration. Both organic salts, such as alkali metal or ammonium halogen salts, e.g., sodium chloride, potassium chloride or organic salts, such as potassium, sodium and ammonium salts or organic acids, e.g., ascorbic acid, citric acid, acetic acid, tartaric acid, etc. may be used for this purpose.

Other pharmaceutically-acceptable excipients may be added to the suspension or solution. The compound of formula (I) or pharmaceutically acceptable salt thereof may be stabilized by the addition of an inorganic acid, e.g., hydrochloric acid, nitric acid, sulfuric acid and/or phosphoric acid; an organic acid, e.g., ascorbic acid, citric acid, acetic acid, and tartaric acid, etc., a complexing agent such as EDTA or citric acid and salts thereof; or an antioxidant such as antioxidant such as vitamin E or ascorbic acid. These may be used alone or together to stabilize the compound of formula (I) or pharmaceutically acceptable salt thereof. Preservatives may be added such as benzalkonium chloride or benzoic acid and salts thereof. Surfactant may be added particularly to improve the physical stability of suspensions. These include lecithin, disodium dioctylsulfosuccinate, oleic acid and sorbitan esters.

In a further aspect, the invention is directed to a dosage form adapted for intranasal administration.

Formulations for administration to the nose may include pressurised aerosol formulations and aqueous formulations administered to the nose by pressurised pump. Formulations which are non-pressurised and adapted to be administered topically to the nasal cavity are of particular interest. Suitable formulations contain water as the diluent or carrier for this purpose. Aqueous formulations for administration to the lung or nose may be provided with conventional excipients such as buffering agents, tonicity modifying agents and the like. Aqueous formulations may also be administered to the nose by nebulisation.

The compounds of formula (I) or pharmaceutically acceptable salts thereof may be formulated as a fluid formulation for delivery from a fluid dispenser, for example a fluid dispenser having a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. A fluid dispenser of the aforementioned type is described and illustrated in WO 05/044354, the entire content of which is hereby incorporated herein by reference. The dispenser has a housing which houses a fluid discharge device having a compression pump mounted on a container for containing a fluid formulation. The housing has at least one finger-operable side lever which is movable inwardly with respect to the housing to cam the container upwardly in the housing to cause the pump to compress and pump a metered dose of the formulation out of a pump stem through a nasal nozzle of the housing. In one embodiment, the fluid dispenser is of the general type illustrated in FIGS. 30-40 of WO 05/044354.

Pharmaceutical compositions adapted for intranasal administration wherein the carrier is a solid include a coarse powder having a particle size for example in the range 20 to 500 microns which is administered by rapid inhalation through the nasal passage from a container of the powder held close up to the nose. Suitable compositions wherein the carrier is a liquid, for administration as a nasal spray or as nasal drops, include aqueous or oil solutions of the compound of formula (I) or a pharmaceutically acceptable salt thereof.

Pharmaceutical compositions adapted for transdermal administration may be presented as discrete patches intended to remain in intimate contact with the epidermis of the patient for a prolonged period of time. For example, the active ingredient may be delivered from the patch by iontophoresis as generally described in Pharmaceutical Research, 3(6), 318 (1986).

Pharmaceutical compositions adapted for topical administration may be formulated as ointments, creams, suspensions, lotions, powders, solutions, pastes, gels, sprays, aerosols or oils.

Ointments, creams and gels, may, for example, be formulated with an aqueous or oily base with the addition of suitable thickening and/or gelling agent and/or solvents. Such bases may thus, for example, include water and/or an oil such as liquid paraffin or a vegetable oil such as *arachis* oil or castor oil, or a solvent such as polyethylene glycol. Thickening agents and gelling agents which may be used according to the nature of the base include soft paraffin, aluminium stearate, cetostearyl alcohol, polyethylene glycols, woolfat, beeswax, carboxypolymethylene and cellulose derivatives, and/or glyceryl monostearate and/or non-ionic emulsifying agents.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilising agents, suspending agents or preservatives.

Topical preparations may be administered by one or more applications per day to the affected area. Over skin areas, occlusive dressings may advantageously be used. Continuous or prolonged delivery may be achieved by an adhesive reservoir system.

For treatments of the eye or other external tissues, for example mouth and skin, the compositions may be applied as a topical ointment or cream. When formulated in an ointment, the compound of formula (I) or a pharmaceutically acceptable salt thereof may be employed with either a paraffinic or a water-miscible ointment base. Alternatively, the compound of formula (I) or pharmaceutically acceptable salt thereof may be formulated in a cream with an oil-in-water cream base or a water-in-oil base.

Pharmaceutical compositions adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

The invention will now be illustrated by way of the following non-limiting examples.

General Methods

Unless stated otherwise, starting materials were commercially available. All solvents and commercial reagents were of laboratory grade and were used as received.

Where diastereoisomers are represented and only the relative stereochemistry is referred to, the bold or hashed solid bond symbols (━/⁙⁙⁙) are used. Where the absolute stereochemistry is known and the compound is a single enantiomer, the bold or hashed wedges symbols (━/⁙⁙⁙) are used as appropriate.

Analytical Methods

Method A

LCMS was conducted on an Acquity UPLC BEH $C_{18}$ column (50 mm×2.1 mm i.d. 1.7 µm packing diameter) at 40 degrees centigrade, eluting with 10 mM ammonium bicarbonate in water adjusted to pH 10 with ammonia solution (Solvent A) and acetonitrile (Solvent B) using the following elution gradient: 0-1.5 min: 1-97% B, 1.5-1.9 min: 97% B, 1.9-2.0 min: 100% B at a flow rate of 1 ml/min. The UV detection was a summed signal from wavelength of 210 nm to 350 nm. The mass spectra were recorded on a Waters ZQ Mass Spectrometer using Alternate-scan Positive and Negative Electrospray. Ionisation data were rounded to the nearest integer.

Method B

LCMS was conducted on an Acquity UPLC BEH $C_{18}$ column (50 mm×2.1 mm i.d. 1.7 µm packing diameter) at 40 degrees centigrade, eluting with 0.1% v/v solution of formic acid in water (Solvent A) and 0.1% v/v solution of formic acid in acetonitrile (Solvent B) using the following elution gradient: 0-1.5 min: 3-100% B, 1.5-1.9 min: 100% B, 1.9-2.0 min: 3% B at a flow rate of 1 ml/min. The UV detection was a summed signal from wavelength of 210 nm to 350 nm. The mass spectra were recorded on a Waters ZQ Mass Spectrometer using Alternate-scan Positive and Negative Electrospray. Ionisation data were rounded to the nearest integer.

Method C

LCMS was conducted on an Acquity UPLC BEH $C_{18}$ column (50 mm×2.1 mm i.d. 1.7 µm packing diameter) at 40 degrees centigrade, eluting with 0.1% v/v solution of trifluoroacetic acid in water (Solvent A) and 0.1% v/v solution of trifluoroacetic acid in acetonitrile (Solvent B) using the following elution gradient: 0-1.5 min: 3-100% B, 1.5-1.9 min: 100% B, 1.9-2.0 min: 3% B at a flow rate of 1 ml/min. The UV detection was a summed signal from wavelength of 210 nm to 350 nm. The mass spectra were recorded on a Waters ZQ Mass Spectrometer using Alternate-scan Positive and Negative Electrospray. Ionisation data were rounded to the nearest integer.

Method D

LCMS was conducted on a HALO $C_{18}$ column (50 mm×4.6 mm i.d. 2.7 µm packing diameter) at 40 degrees centigrade, eluting with 0.1% v/v solution of formic acid in water (Solvent A) and 0.1% v/v solution of formic acid in acetonitrile (Solvent B) using the following elution gradient: 0-1.8 min: 5% B, 1.8-2.01 min: 100% B, 2.01-2.8 min: 5% B at a flow rate of 1.5 ml/min. The UV detection was a summed signal at wavelength: 214 nm and 254 nm. MS: Ion Source: ESI; Detector Voltage: 1.4 KV; Heat Block temp.: 250° C.; CDL temp.: 250° C.; Nebuliser Gas Flow: 1.5 mL/min.

Method E

LCMS was conducted on a HALO $C_{18}$ column (50 mm×4.6 mm i.d. 2.7 µm packing diameter) at 40 degrees centigrade, eluting with 0.1% v/v solution of formic acid in water (Solvent A) and 0.1% v/v solution of formic acid in acetonitrile (Solvent B) using the following elution gradient: 0-1 min: 5% B, 1-2.01 min: 95% B, 2.01-2.5 min: 5% B at a flow rate of 1.8 ml/min. The UV detection was a summed signal at wavelength: 214 nm and 254 nm. MS: Ion Source: ESI; Drying Gas Flow: 10 L/min; Nebuliser Pressure: 45 psi; Drying Gas Temperature: 330° C.; Capillary Voltage: 4000V.

General GC Method

GCMS was conducted on an Agilent 6890/5973 GCMS equipment with an Agilent capillary column HP-5 (0.25 um×30 m, i.d. 0.25 mm). The initial temperature is 50° C. The equilibration time is 0.50 min. The initial time is 1.00 min. The temperature then increase to 180° C. with a rate of 10°/min, then rise to 240° C. with a rate of 20° C./min, then hold 240° C. for 5.00 min. The injection mode is splitless. The gas flow is 1.00 ml/min and the total flow is 23.2 ml/min. The average velocity is 36 cm/sec. The acquisition mode is scan. The ionization method is 70 eV EI (Electronic Ionization).

$^1$H NMR spectra were recorded using a Bruker DPX 400 MHz or AV 600 MHz spectrometer, referenced to tetramethylsilane.

Silica chromatography techniques include either automated (Flashmaster, Biotage SP4) techniques or manual chromatography on pre-packed cartridges (SPE) or manually-packed flash columns.

When the name of a commercial supplier is given after the name of a compound or a reagent, for instance "compound X (Aldrich)" or "compound X/Aldrich", this means that compound X is obtainable from a commercial supplier, such as the commercial supplier named.

Similarly, when a literature or a patent reference is given after the name of a compound, for instance 'compound Y (EP 0 123 456)', this means that the preparation of the compound is described in the named reference.

The names of the intermediates and examples have been obtained using the compound naming programme within ChemBioDraw Ultra v12, or alternatively using "ACD Name Pro 6.02".

General MDAP Purification Methods

Listed below are examples of mass-directed autopreparative chromatography (MDAP) methods that have been used or may be used in compound purification.

MDAP (Method A). The HPLC analysis is conducted on an XBridge $C_{18}$ column (100 mm×30 mm i.d. 5 µm packing diameter) at ambient temperature, eluting with 10 mM ammonium bicarbonate in water adjusted to pH 10 with ammonia solution (Solvent A) and acetonitrile (Solvent B) using the following elution gradient:

| Time (min) | Flow Rate (ml/min) | % A | % B |
|---|---|---|---|
| 0 | 40 | 85 | 15 |
| 1 | 40 | 85 | 15 |
| 10 | 40 | 45 | 55 |
| 11 | 40 | 1 | 99 |
| 15 | 40 | 1 | 99 |

The UV detection is an averaged signal from wavelength of 210 nm to 350 nm. The mass spectra are recorded on a Waters ZQ Mass Spectrometer using Alternate-scan Positive and Negative Electrospray. Ionisation data are rounded to the nearest integer.

MDAP (Method B). The HPLC analysis is conducted on an XBridge $C_{18}$ column (100 mm×30 mm i.d. 5 µm packing diameter) at ambient temperature, eluting with 10 mM ammonium bicarbonate in water adjusted to pH 10 with ammonia solution (Solvent A) and acetonitrile (Solvent B) using the following elution gradient:

| Time (min) | Flow Rate (ml/min) | % A | % B |
|---|---|---|---|
| 0 | 40 | 85 | 15 |
| 1 | 40 | 85 | 15 |
| 20 | 40 | 45 | 55 |
| 21 | 40 | 1 | 99 |
| 25 | 40 | 1 | 99 |

The UV detection is an averaged signal from wavelength of 210 nm to 350 nm. The mass spectra are recorded on a Waters ZQ Mass Spectrometer using Alternate-scan Positive and Negative Electrospray. Ionisation data are rounded to the nearest integer.

MDAP (Method C). The HPLC analysis is conducted on a Sunfire $C_{18}$ column (150 mm×30 mm i.d. 5 µm packing diameter) at ambient temperature, eluting with 0.1% v/v solution of trifluoroacetic acid in water (Solvent A) and 0.1% v/v solution of trifluoroacetic acid in acetonitrile (Solvent B) using the following elution gradient:

| Time (min) | Flow Rate (ml/min) | % A | % B |
|---|---|---|---|
| 0 | 40 | 100 | 0 |
| 3 | 40 | 100 | 0 |
| 3.5 | 30 | 100 | 0 |
| 24.5 | 30 | 70 | 30 |
| 25 | 30 | 1 | 99 |
| 32 | 30 | 1 | 99 |

The UV detection is an averaged signal from wavelength of 210 nm to 350 nm. The mass spectra are recorded on a Waters ZQ Mass Spectrometer using Alternate-scan Positive and Negative Electrospray. Ionisation data are rounded to the nearest integer.

MDAP (Method D). The HPLC analysis is conducted on a Sunfire $C_{18}$ column (150 mm×30 mm i.d. 5 µm packing diameter) at ambient temperature, eluting with 10 mM ammonium bicarbonate in water adjusted to pH 10 with ammonia solution (Solvent A) and acetonitrile (Solvent B) using the following elution gradient:

| Time (min) | Flow Rate (ml/min) | % A | % B |
|---|---|---|---|
| 0 | 40 | 100 | 0 |
| 3 | 40 | 100 | 0 |
| 3.5 | 30 | 100 | 0 |
| 24.5 | 30 | 70 | 30 |
| 25 | 30 | 1 | 99 |
| 32 | 30 | 1 | 99 |

The UV detection is an averaged signal from wavelength of 210 nm to 350 nm. The mass spectra are recorded on a Waters ZQ Mass Spectrometer using Alternate-scan Positive and Negative Electrospray. Ionisation data are rounded to the nearest integer.

MDAP (Method E). The HPLC analysis was conducted on an XBridge C18 column (100 mm×30 mm i.d. 5 µm packing diameter) at ambient temperature, eluting with 10 mM Ammonium Bicarbonate in water adjusted to pH 10 with Ammonia solution (Solvent A) and Acetonitrile (Solvent B) using an elution gradient of between 0 and 100% Solvent B over 15 or 25 minutes.

The UV detection was an averaged signal from wavelength of 210 nm to 350 nm. The mass spectra were recorded on a Waters ZQ Mass Spectrometer using Alternate-scan Positive and Negative Electrospray. Ionisation data was rounded to the nearest integer.

MDAP (Method F). The HPLC analysis was conducted on a Sunfire C18 column (150 mm×30 mm i.d. 5 µm packing diameter) at ambient temperature, eluting with 0.1% v/v solution of Trifluoroacetic Acid in Water (Solvent A) and 0.1% v/v solution of Trifluoroacetic Acid in Acetonitrile (Solvent B) using an elution gradient of between 0 and 100% Solvent B over 15 or 25 minutes.

The UV detection was an averaged signal from wavelength of 210 nm to 350 nm. The mass spectra were recorded on a Waters ZQ Mass Spectrometer using Alternate-scan Positive and Negative Electrospray. Ionisation data was rounded to the nearest integer.

MDAP (Method G). The HPLC analysis was conducted on a Sunfire C18 column (150 mm×30 mm i.d. 5 µm packing diameter) at ambient temperature, eluting with 0.1% formic acid in water (Solvent A) and 0.1% formic acid in acetonitrile (Solvent B) using an elution gradient of between 0 and 100% Solvent B over 15 or 25 minutes.

The UV detection was an averaged signal from wavelength of 210 nm to 350 nm. The mass spectra were recorded on a Waters ZQ Mass Spectrometer using Alternate-scan Positive and Negative Electrospray. Ionisation data was rounded to the nearest integer.

General Chiral HPLC Methods

| Method A: Chiral Analytical Chromatography | |
|---|---|
| Column | Chiralpak AD-H, 250 × 4.6 mm |
| Mobile Phase | A: n-Hexane    B: Ethanol |
| Gradient Profile | 90:10 mobile phase A:B |
| Flow Rate | 1 mL/min |
| Column Temperature | 20° C. |
| Detection wavelength | 215 nm or UV DAD (300 nm (bandwidth 180 nm, reference 550 nm (bandwidth 100 nm)) |

| Method B: Chiral Preparative Chromatography | |
|---|---|
| Column | Chiralpak AD-H, 250 × 30 mm, 5 µm [ADH10029-01] |
| Mobile Phase | A: n-Hexane    B: Ethanol |
| Gradient Profile | Stepped Isocratic system - 90:10 mobile phase A:B |
| Run Time | 20 min |
| Flow Rate | 45 mL/min |
| Column Temperature | 20° C. |
| Detection | UV DAD (300 nm (bandwidth 180 nm, reference 550 nm (bandwidth 100 nm)) |

| Method C: Chiral Preparative Chromatography Initial Conditions: | |
|---|---|
| Column | Chiralpak AD, 250 × 20 mm, 20 µm [self packed] |
| Mobile Phase | A: n-Hexane    B: Ethanol |
| Gradient Profile | 90:10 mobile phase A:B |
| Flow Rate | 75 mL/min |
| Column Temperature | 20° C. |
| Detection wavelength | 215 nm |

An initial cut of the leading edge of the peak was taken using the initial conditions. This gave an enriched cut of the desired first eluting isomer which was then further purified using the secondary conditions.

| Secondary conditions: | |
|---|---|
| Column | Chiralpak AD-H, 250 × 30 mm, 5 µm [ADH10029-01] |
| Mobile Phase | A: n-Hexane    B: Ethanol |
| Gradient Profile | 90:10 mobile phase A:B |
| Flow Rate | 40 mL/min |
| Column Temperature | 20° C. |
| Detection wavelength | 215 nm |

| Method D: Chiral Preparative Chromatography | |
|---|---|
| Column | Chiralpak AD-H, 25 cm × 30 mm, [ADH10029-01] |
| Mobile Phase | A: n-Heptane    B: isopropanol |
| Gradient Profile | 70:30 mobile phase A:B |
| Flow Rate | 15 mL/min |
| Column Temperature | 20° C. |
| Detection wavelength | 215 nm |

INTERMEDIATES

Intermediate 1: 1-(Phenylsulfonyl)-1H-pyrrolo[2,3-b]pyridine

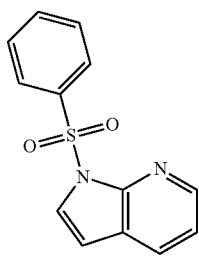 [SMILES: O=S(=O)(c1ccccc1)n1ccc2cccnc21]

To a solution of 1H-pyrrolo[2,3-b]pyridine (20 g, 169 mmol, (available from, for example Sigma Aldrich) in tetrahydrofuran (THF) (250 mL) was added sodium hydride (10.16 g, 254 mmol) portionwise during 5 min under nitrogen at 0° C. The reaction mixture was stirred at 0° C. for 30 min, then benzenesulfonyl chloride was added dropwise under nitrogen at 0° C. then stirred for 2 h at r.t., until the starting material had been completely consumed (TLC, EtOAc: PE=1:1). The mixture was poured into $H_2O$ (200 mL) and extracted with EtOAc (3×200 mL). The organic layers were washed with brine (3×150 mL), dried over $Na_2SO_4$ and filtered. The solvent was evaporated in vacuo to give the crude product, which was purified by recrystallization with (EtOAc and PE) to give desired product as a white solid (30 g, 69%) LCMS (Method D): Rt=1.76 min, MH$^+$=259

Intermediate 2: 1-(Phenylsulfonyl)-1H-pyrrolo[2,3-c]pyridine

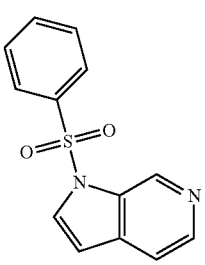 [SMILES: O=S(=O)(c1ccccc1)n1ccc2ccncc21]

Prepared similarly to intermediate 1 starting from 1H-pyrrolo[2,3-c]pyridine (available from, for example, Apollo Scientific Ltd).

1H NMR (DMSO-d6): 9.24 (1H, s, CH), 8.40 (1H, d, CH), 8.11-8.08 (3H, m, CH), 7.82-7.62 (4H, m, CH), 6.95 (1H, d, CH).

Intermediate 3: 1-(Phenylsulfonyl)-1H-pyrrolo[3,2-c]pyridine

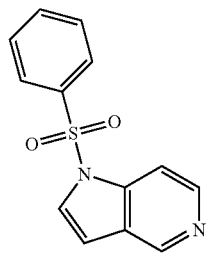 [SMILES: O=S(=O)(c1ccccc1)n1ccc2cnccc21]

Prepared similarly to intermediate 1 starting from 1H-pyrrolo[3,2-c]pyridine (available from, for example, Apollo Scientific Ltd).

$^1$H NMR (400 MHz, DMSO-d$_6$) δ ppm: 8.91 (1H, s, CH), 8.46 (1H, d, CH), 8.07 (2H, d, CH), 7.96-7.92 (2H, m, CH), 7.74 (1H, t, CH), 7.64 (2H, t, CH), 6.99 (1H, d, CH).

Intermediate 4: 1-(Phenylsulfonyl)-1H-pyrrolo[2,3-b]pyridine-2-carbaldehyde

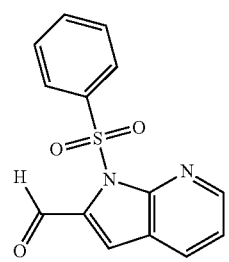

To a solution of diisopropylamine (4.13 mL, 0.029 mol) in anhydrous tetrahydrofuran (THF) (50 mL) stirred under nitrogen at −78° C. was added nBuLi (10.42 mL, 0.026 mol) over 15 min. The reaction mixture was stirred at −78° C. for 30 min. then warmed to r.t. and stirred for 1 h. To this solution of LDA in anhydrous tetrahydrofuran (THF) (250 mL) stirred under nitrogen at −30° C. was added a solution of 1-(phenylsulfonyl)-1H-pyrrolo[2,3-b]pyridine (5 g, 19.36 mmol) and TMEDA (4.38 mL, 29.0 mmol) in tetrahydrofuran (THF) (150 mL) dropwise over 15 min. The reaction mixture was stirred at −30° C. for 2.5 h, then DMF (3 mL, 38.7 mmol) was added dropwise over 1 min. The reaction mixture was stirred at −30° C. for another 2 h, TLC and LC-MS showed complete conversion. The reaction mixture was quenched with water and partitioned between dichloromethane (700 mL) and water (100 mL). The organic phase was washed with water (3×100 mL), dried over sodium sulfate and evaporated in vacuo to give the crude product as a yellow solid. This was purified by recrystallization (EtOAc and PE) to give the desired product—1-(phenylsulfonyl)-1H-pyrrolo[2,3-b]pyridine-2-carbaldehyde (4.8 g, 78%) as a yellow solid.

1H NMR (DMSO-d6): 10.45 (1H, s, CH), 8.58 (1H, dd, CH), 8.24-8.16 (3H, m, CH), 7.74 (1H, t, CH), 7.66-7.58 (3H, m, CH), 7.41 (1H, dd, CH).

Intermediate 5: 1-(Phenylsulfonyl)-1H-pyrrolo[2,3-c]pyridine-2-carbaldehyde

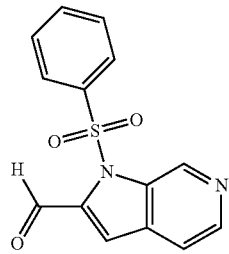 [SMILES: O=Cc1cc2ccncc2n1S(=O)(=O)c1ccccc1]

Prepared similarly to intermediate 4 starting from 1-(phenylsulfonyl)-1H-pyrrolo[2,3-c]pyridine.

1H NMR (DMSO-d6): 10.43 (1H, s, CH), 8.68 (1H, dd, CH), 8.55 (1H, d, CH), 8.02 (2H, dd, CH), 7.76-7.72 (2H, m, CH), 7.62-7.56 (3H, m, CH).

Intermediate 6: 1-(Phenylsulfonyl)-1H-pyrrolo[3,2-c]pyridine-2-carbaldehyde

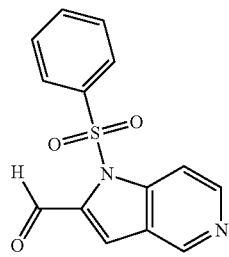 [SMILES: O=Cc1cc2cnccc2n1S(=O)(=O)c1ccccc1]

Prepared similarly to intermediate 4 starting from 1-(phenylsulfonyl)-1H-pyrrolo[3,2-c]pyridine LCMS (Method D): Rt=1.39 min, MH+=286.9.

Intermediate 7: 1H-Pyrrolo[2,3-b]pyridine-2-carbaldehyde

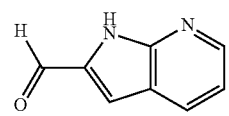 [SMILES: O=Cc1cc2cccnc2[nH]1]

To a solution of 1-(phenylsulfonyl)-1H-pyrrolo[2,3-b]pyridine-2-carbaldehyde (2.5 g, 8.73 mmol) in methanol (50 mL) stirred under nitrogen at r.t. was added a solution of KOH (1.96 g, 34.9 mmol) in water (5 mL) dropwise during 1 min. The reaction mixture was stirred at r.t. for 30 min, TLC showed complete conversion. The reaction mixture was diluted with H$_2$O (150 mL), extracted with dichloromethane (3×150 mL) and the organic phase was washed with saturated brine (3×50 mL), water 100 mL, dried over sodium sulfate and evaporated in vacuo to give the title compound as a yellow solid (1 g, 54.9% yield) which was used in the next reaction without further purification.

1H NMR (DMSO-d6): 12.51 (1H, br s, NH), 9.90 (1H, s, CH), 8.48 (1H, dd, CH), 8.21 (1H, d, CH), 7.41 (1H, s, CH), 7.20 (1H, dd, CH).

Intermediate 8: 1H-Pyrrolo[2,3-c]pyridine-2-carbaldehyde

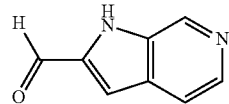 [SMILES: O=Cc1cc2ccncc2[nH]1]

Prepared similarly to intermediate 7 starting from 1-(phenylsulfonyl)-1H-pyrrolo[2,3-c]pyridine-2-carbaldehyde.

1H NMR (DMSO-d6): 12.40 (1H, brs, NH), 9.99 (1H, s, CH), 8.87 (1H, s, CH), 8.19 (1H, d, CH), 7.74 (1H, dd, CH), 7.42 (1H, s, CH).

Intermediate 9: 1H-Pyrrolo[3,2-c]pyridine-2-carbaldehyde

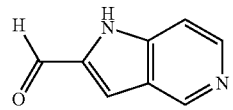 [SMILES: O=Cc1cc2cnccc2[nH]1]

Prepared similarly to intermediate 7 starting from 1-(phenylsulfonyl)-1H-pyrrolo[3,2-c]pyridine-2-carbaldehyde.

1H NMR (DMSO-d6): 12.34 (1H, brs, NH), 9.94 (1H, s, CH), 9.07 (1H, s, CH), 8.34 (1H, d, CH), 7.57 (1H, s, CH), 7.41 (1H, d, CH).

Intermediate 10: 1-Ethyl-1H-pyrrolo[2,3-b]pyridine-2-carbaldehyde

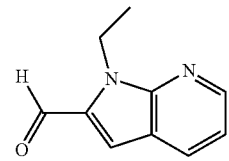

To a suspension of 1H-pyrrolo[2,3-b]pyridine-2-carbaldehyde (700 mg, 4.79 mmol) and Cs$_2$CO$_3$ (3121 mg, 9.58 mmol) in N,N-dimethylformamide (DMF) (20 mL) stirred under nitrogen at 20° C., was added iodoethane (0.581 mL, 7.18 mmol) dropwise during 0.5 min. The reaction mixture was stirred at rt for 1 h, TLC showed complete conversion.

In a separate reaction: To a suspension of 1H-pyrrolo[2,3-b]pyridine-2-carbaldehyde (600 mg, 4.11 mmol) and Cs$_2$CO$_3$ (2675 mg, 8.21 mmol) in N,N-Dimethylformamide (DMF) (20 mL) stirred under nitrogen at 20° C. was added iodoethane (0.498 mL, 6.16 mmol) dropwise during 0.5 min. The reaction mixture was stirred at r.t. for 1 h, TLC showed complete conversion.

The combined reaction mixtures were quenched with water, partitioned between dichloromethane (100 mL) and water (50 mL). the water phase was extracted with dichloromethane (3×100 mL). The organic phase was washed with saturated brine (3×50 mL), dried over sodium sulfate and evaporated in vacuo to give the crude product as a yellow oil. The crude product was purified by a silica gel column (Hex/EtOAc, 10/1) to give the title compound (511 mg, 32%).

LCMS (Method E): Rt=1.45 min, MH+=175.1.

Intermediate 11: 1-Ethyl-1H-pyrrolo[2,3-c]pyridine-2-carbaldehyde

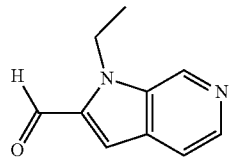

Prepared similarly to intermediate 10 starting from 1H-pyrrolo[2,3-c]pyridine-2-carbaldehyde GCMS: Rt=14.32 min, M+=174.

Intermediate 12: 1-Ethyl-1H-pyrrolo[3,2-c]pyridine-2-carbaldehyde

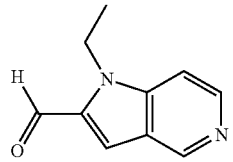

Prepared similarly to intermediate 10 starting from 1H-pyrrolo[3,2-c]pyridine-2-carbaldehyde.
LCMS (Method E): Rt=0.61 min, MH+=175.1.

Intermediate 13: 1-(Cyclopropylmethyl)-1H-pyrrolo[2,3-b]pyridine-2-carbaldehyde

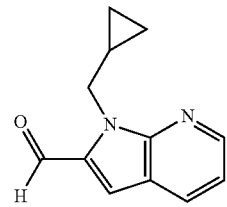 [SMILES: O=Cc1cc2cccnc2n1CC1CC1]

A solution of sodium hydride (60.2 mg, 1.51 mmol) in N,N-dimethylformamide (20 mL) was stirred at 00° C. for 10 min. 1H-Pyrrolo[2,3-b]pyridine-2-carbaldehyde (200 mg, 1.37 mmol) was added and the mixture was stirred at 0° C. for 30 min and at rt for 30 min. (Bromomethyl)cyclopropane (0.16 mL, 1.64 mmol available, for example, from Alfa Aesar) was added and the resulting mixture was stirred at 0° C. for 30 min and at rt for 21 h. Reaction mixture was quenched by the addition of water (50 mL). After addition of Et2O (50 mL), the layers were separated. The aqueous layer was further extracted with Et2O (2×50 mL) and the combined organic layers were washed with H2O (2×35 mL). The organic phase was dried through a hydrophobic frit and concentrated under reduced pressure to give a brown oil which was loaded in DCM on a 50 g SNAP silica cartridge and purified by SP4, eluting with a gradient of 0-20% ethyl acetate/cyclohexane (15 CV). The appropriate fractions were combined and evaporated under reduced pressure to give the required product 1-(cyclopropylmethyl)-1H-pyrrolo[2,3-b]pyridine-2-carbaldehyde (201 mg, 73.4%) as a colourless oil.
LCMS (Method B): Rt=0.99 min, MH+=201.0

Intermediate 14: 1-(2,2,2-Trifluoroethyl)-1H-pyrrolo[2,3-b]pyridine-2-carbaldehyde

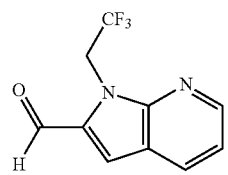 [SMILES: O=Cc1cc2cccnc2n1CC(F)(F)F]

1H-Pyrrolo[2,3-b]pyridine-2-carbaldehyde (1.8 g, 12.32 mmol) was added to a solution of sodium hydride (0.54 g, 13.55 mmol) in N,N-dimethylformamide (50 mL) at rt under nitrogen. The reaction mixture was allowed to stir for 1 h before the reaction mixture was cooled to 0° C. and 2,2,2-trifluoroethyl trifluoromethanesulfonate (2.04 ml, 14.78 mmol available, for example, from Sigma Aldrich) was added dropwise. The reaction mixture was stirred for 1 h at 0° C. and for 14 h at rt under nitrogen. The reaction was quenched by addition of water (150 mL). After addition of Et2O (150 mL), the layers were separated. The aqueous layer was further extracted with Et2O (3×150 mL) and the combined organic layers were washed with H2O. The combined water layers were extracted with Et2O (150 mL). The organic layers collected were combined, dried over Na2SO4, filtered and concentrated under reduced pressure. The residue was loaded in dichloromethane on two 100 g SNAP silica cartridge and purified by SP4, eluting with 0-30% ethyl acetate/cyclohexane gradient. The appropriate fractions were combined and evaporated under reduced pressure to give the required product 1-(2,2,2-trifluoroethyl)-1H-pyrrolo[2,3-b]pyridine-2-carbaldehyde (2.6 g, 11.39 mmol, 93% yield) as a white solid.
LCMS (Method B): Rt=0.92 min, MH+=229.14.

Intermediate 15: Ethyl 1-ethyl-5-methoxy-1H-pyrrolo[2,3-b]pyridine-2-carboxylate

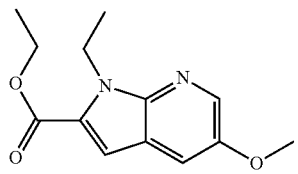 [SMILES: CCOC(=O)c1cc2cc(OC)cnc2n1CC]

To a solution of ethyl 5-methoxy-1H-pyrrolo[2,3-b]pyridine-2-carboxylate (150 mg, 0.68 mmol available, for example, from Shanghai Haoyuan Chemexpress Co., Ltd) in DMSO (4 ml) was added powdered potassium hydroxide (115 mg, 2.04 mmol) followed by bromoethane (0.071 ml, 0.95 mmol). The mixture was stirred at rt for 2 hr then further bromoethane (0.020 ml) was added and the mixture stirred for a further 18 hr. The reaction was quenched by the addition of water then partitioned between water and diethyl ether. The organic phase was washed with water then passed through a hydrophobic frit and finally concentrated under reduced pressure to give the product as an orange/brown oil. The crude material was purified with column chromatography (eluted with DCM and ethyl acetate from 0 to 10%) to give the title compound as clear oil (60 mg, 36%).

LCMS (Method C): MH+=249.1, Rt=1.15 min

Intermediate 16: 1-Ethyl-5-methoxy-1H-pyrrolo[2,3-b]pyridine-2-carboxylic acid

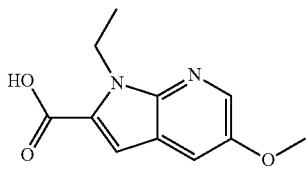 [SMILES: CCn1c(C(=O)O)cc2cc(OC)cnc21]

To a solution of ethyl 1-ethyl-5-methoxy-1H-pyrrolo[2,3-b]pyridine-2-carboxylate (60 mg, 0.24 mmol) in THF (2 ml) and MeOH (0.5 ml) was added lithium hydroxide (35 mg, 1.45 mmol) in water (2 mL). A cloudy solution formed which became clear after 30 s. The reaction mixture was allowed to stand at room temperature for 18 hr then concentrated under a stream of nitrogen. 2M HCl (2 ml, aqueous) was added to the crude product and the resulting solid filtered then dried under reduced pressure to give the title compound as an off-white solid (32 mg, 60%).

LCMS (Method C): Rt=0.80 min, MH+=221.1

Intermediate 17: 1-Ethyl-5-methoxy-1H-pyrrolo[2,3-c]pyridine-2-carboxylic acid

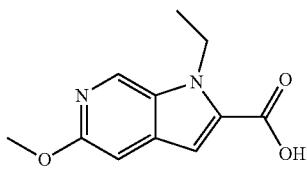 [SMILES: CCn1c(C(=O)O)cc2cc(OC)ncc21]

To a solution of 5-methoxy-1H-pyrrolo[2,3-c]pyridine-2-carboxylic acid (500 mg, 2.60 mmol) (available from, for example, Activate Scientific GmbH) in dimethyl sulfoxide (DMSO) (5 mL) was added potassium hydroxide (438 mg, 7.81 mmol) and bromoethane (0.427 mL, 5.72 mmol). The reaction was stirred at room temperature for 18 h before adding further potassium hydroxide (120 mg) and bromoethane (0.13 ml). After stirring for a further 4 h, the reaction mixture was stood under nitrogen for ca. 66 h. It was then partitioned between water and diethyl ether. The layers were separated and the aqueous was washed with diethyl ether. The aqueous was acidified to pH=3, and was extracted with ethyl acetate (twice). The combined ethyl acetate extracts were washed with water and concentrated in vacuo to yield the title compound as a pale beige solid (148 mg).

LCMS (Method C): Rt=0.46 min, MH+=221

Intermediate 18: Methyl 4-(methylamino)-3-nitrobenzoate

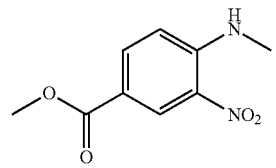

Methylamine (2M in THF) (23.19 mL, 46.4 mmol) was added to a solution of methyl 4-chloro-3-nitrobenzoate (5 g, 23.19 mmol) (available, for example, from Lancaster Synthesis Ltd.) in N,N-dimethylformamide (DMF) (8 mL) at rt under nitrogen. The reaction mixture was heated to 80° C. and stirred overnight. LCMS showed major peak product, but reaction had not gone to completion. Further methylamine (2M in THF, 10 ml) was added and the reaction heated to 90° C. for 6 h. Further methylamine (2M in THF, 6 ml) was added and the reaction stirred for 1 h at rt and 72 h at 70° C. Further methylamine (2M in THF, 10 ml) was added and the reaction heated to 80° C. for 3 h. The reaction was allowed to cool to rt and then the product was precipitated by the addition of water (50 mL). The resultant suspension was cooled to 0° C. and then filtered. The residue was washed with further water (3×25 mL) and allowed to dry on the filter pad for ~15 mins. The solid was collected and dried in vacuo to afford the title compound as a yellow solid (4.54 g, 21.60 mmol, 93% yield).

LCMS (Method B): Rt=0.69 min, MH+=197.2

Intermediate 19: 4-(Methylamino)-3-nitrobenzoic acid

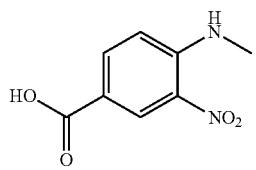

Methyl 4-(methylamino)-3-nitrobenzoate (1.82 g, 8.66 mmol) was dissolved in a 1:1 ratio of tetrahydrofuran (THF) (41.4 mL) and water (41.4 mL). To this was added lithium hydroxide (1.817 g, 43.3 mmol) and the reaction stirred at r.t. for 16 h. The reaction mixture was cooled to 0° C. and acidified by the addition of 5M HCl (~20 mL, until the pH reached ~5)—a bright yellow precipitate formed, the slurry was filtered and the residue washed with distilled $H_2O$ (2×30 mL). The residue was collected and dried in vacuo at 50° C.

to afford the product as a yellow solid (1.43 g, 7.29 mmol, 84% yield). This was used without further purification in the subsequent reactions.

LCMS (Method B): Rt=0.92 min, MH+=211

Intermediate 20: (R)-tert-Butyl (1-(4-(methyl-amino)-3-nitrobenzoyl)piperidin-3-yl)carbamate

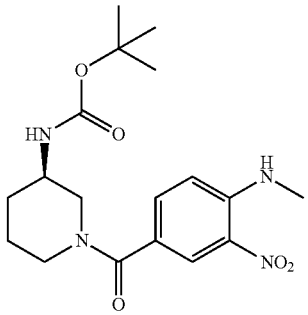 [SMILES: CNc1ccc(C(=O)N2CCC[C@@H](NC(=O)OC(C)(C)C)C2)cc1[N+](=O)[O-]]

To a solution of (R)-tert-butyl piperidin-3-ylcarbamate (1.460 g, 7.29 mmol) (available from, for example, Apollo Scientific Ltd), 4-(methylamino)-3-nitrobenzoic acid (1.43 g, 7.29 mmol) and HATU (2.77 g, 7.29 mmol) in N,N-dimethylformamide (DMF) (50 mL) was added DIPEA (2.55 mL, 14.58 mmol) and the reaction stirred at r.t. for 16 h. Water (200 mL) and Et$_2$O (200 mL) were added and the layers separated. The aqueous layer was extracted with further Et$_2$O (2×200 mL) and the combined organics washed with water (2×50 mL), dried (Na$_2$SO$_4$) and concentrated in vacuo to afford a bright yellow oil. The crude product was purified on silica (100 g) using a gradient of 40% EtOAc/cyclohexane→100% ethyl acetate/cyclohexane. The appropriate fractions were combined and evaporated under vacuum to give the title product as an orange-gold solid (2.76 g, 7.29 mmol, 100% yield).

LCMS (Method B): Rt=0.96 min, MH+=379.3

Intermediate 21: tert-Butyl (1-(4-(methylamino)-3-nitrobenzoyl)piperidin-3-yl)carbamate

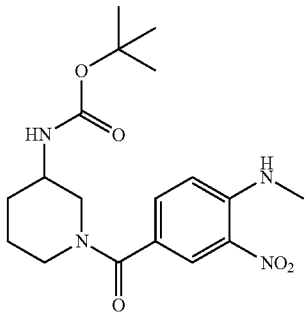 [SMILES: CNc1ccc(C(=O)N2CCCC(NC(=O)OC(C)(C)C)C2)cc1[N+](=O)[O-]]

Prepared similarly to intermediate 20 from tert-butyl piperidin-3-ylcarbamate (available from, for example, Apollo Scientific Ltd) and 4-(methylamino)-3-nitrobenzoic acid.

LCMS (Method B): Rt=0.96 min, MH+=379.2

Intermediate 22: (R)-tert-Butyl (1-(3-amino-4-(methylamino)benzoyl)piperidin-3-yl)carbamate

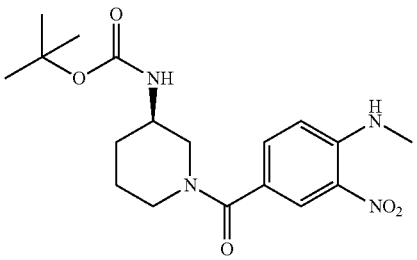 [SMILES: CNc1ccc(C(=O)N2CCC[C@@H](NC(=O)OC(C)(C)C)C2)cc1[N+](=O)[O-]]

(R)-tert-Butyl (1-(4-(methylamino)-3-nitrobenzoyl)piperidin-3-yl)carbamate (3.79 g, 10.02 mmol) was dissolved in ethanol (75 mL) and added to a flushed hydrogenation flask containing Pd/C (380 mg, 0.411 mmol). The resultant mixture was flushed with nitrogen/vacuum 3 times, then stirred under an atmosphere of hydrogen at room temperature for 24 hours. The reaction mixture was flushed from hydrogen atmosphere with nitrogen/vacuum three times. To this solution Celite (33 g) was added and stirred for 2 min. then filtered under vacuum. The solution was concentrated under vacuum to give a crude product that was purified on a 100 g SNAP cartridge using SP4 column chromotography. The column was eluted with 0-6% 2M NH$_3$ in MeOH in DCM over 25 CV. The appropriate fractions were combined and concentrated in vacuo to give a product that was further purified using SP4 column chromotography on a 100 g SNAP cartridge. The column was eluted with 0-100% EtOAc in cyclohexane over 15 CV followed by 100% EtOAc 5 CV followed by 0-6% 2M NH3 in MeOH in DCM over 15 CV. The appropriate fractions were combined and concentrated in vacuo to give the title compound as a pink solid (1.26 g).

LCMS (Method B): Rt=0.70 min, MH+=349.1

Intermediate 23: Methyl 3-methoxy-4-(methylamino)-5-nitrobenzoate

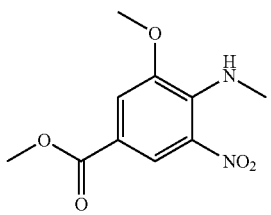

Methyl 4-chloro-3-methoxy-5-nitrobenzoate (available from, for example, Apollo Scientific Ltd) (14 g, 57.0 mmol) was dissolved in N,N-dimethylformamide (DMF) (140 mL) and cooled to ~0° C. in an ice/water bath. Methanamine (2M in THF) (114 mL, 228 mmol) was added dropwise with vigorous stirring using a dropping funnel and the mixture was flushed with nitrogen and heated at 80° C. for 3 hr. The mixture was allowed to cool to room temperature over the weekend. The reaction mixture was diluted with water (500 mL), and filtered under vacuum to give the title compound as an orange solid (13.69 g).

LCMS (Method A): Rt=1.04 min, MH+=241.05

Intermediate 24: 3-Methoxy-4-(methylamino)-5-nitrobenzoic acid

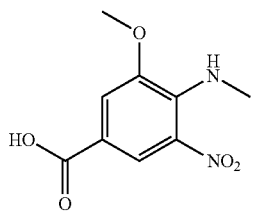 [SMILES: CNc1c(OC)cc(C(=O)O)cc1[N+](=O)[O-]]

To a solution of methyl 3-methoxy-4-(methylamino)-5-nitrobenzoate (13.69 g, 57.0 mmol) in tetrahydrofuran (THF) (100 mL) and water (50.0 mL) was added a single portion of lithium hydroxide (4.09 g, 171 mmol). The resulting suspension was stirred for 19 hr at room temperature. The reaction was acidified with aq. 2N HCl (~50 mL), until pH reached ~4. The resultant suspension was filtered and the orange solid dried on the high vacuum line overnight to give the title compound as an orange solid (11.09 g).
LCMS (Method A): Rt=0.51 min, MH+=227.0

Intermediate 25: (R)-tert-Butyl (1-(3-methoxy-4-(methylamino)-5-nitrobenzoyl)piperidin-3-yl)carbamate

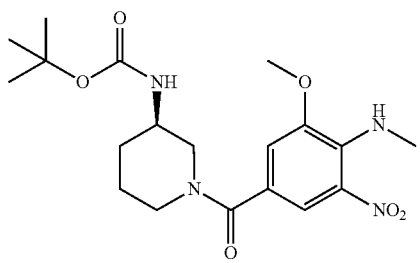 [SMILES: CNc1c(OC)cc(C(=O)N2CCC[C@@H](NC(=O)OC(C)(C)C)C2)cc1[N+](=O)[O-]]

To a solution of 3-methoxy-4-(methylamino)-5-nitrobenzoic acid (11.09 g, 49.0 mmol) and HATU (18.64 g, 49.0 mmol) in N,N-dimethylformamide (DMF) (300 mL) was added DIPEA (17.13 mL, 98 mmol) and the mixture stirred for 30 mins. Upon addition of the DIPEA the mixture went cloudy after ~1 min with stirring. (R)-tert-Butyl piperidin-3-ylcarbamate (9.82 g, 49.0 mmol) was then added and stirred for 1.5 hr, after which time LCMS showed the reaction was complete. To 5 mL of the reaction mixture was added sat.aq. LiCl solution (5 mL) and Et₂O (10 mL) and the layers separated. The aqueous layer was re-extracted with Et₂O (2×10 mL), the combined organics were backwashed with water (10 mL), dried with Na₂SO₄, filtered and concentrated in vacuo to give the crude product as an orange gum. The gum was dissolved in the minimum amount of DCM and purified by Si SNAP 25 g column using a 50-100% ethyl acetate/cyclohexane. The appropriate fractions were combined and evaporated in vacuo before being azeotroped with cyclohexane and dried under vacuum to give the required product, 281 mg as an orange solid. The remaining reaction mixture was concentrated in vacuo to remove some of the DMF. Saturated aq.LiCl solution (300 mL) and Et₂O (700 mL) were added and the mixture separated. The aqueous layer was re-extracted with Et₂O (2×700 mL), the combined organic layers were backwashed with water (1 L), dried with Na₂SO₄, filtered and concentrated in vacuo to give the crude product as an orange gum. This was purified on a 340 g SNAP silica cartridge eluting with 30%-60% ethyl acetate in cyclohexane. Appropriate fractions were combined and concentrated in vacuo to yield the title compound as an orange solid (19.4 g).
LCMS: (Method B): Rt=1.02 min, MH+=409.1

Intermediate 26: (R)-tert-Butyl (1-(2-(1-ethyl-1H-pyrrolo[2,3-c]pyridin-2-yl)-1-methyl-1H-benzo[d]imidazole-5-carbonyl)piperidin-3-yl)carbamate

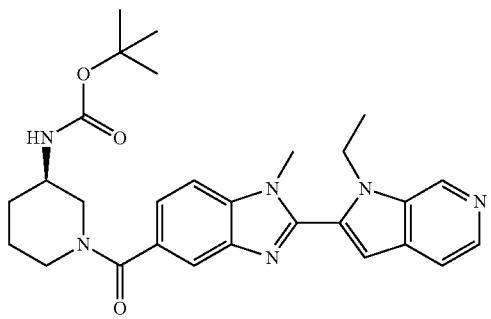 [SMILES: CCn1c(-c2nc3cc(C(=O)N4CCC[C@@H](NC(=O)OC(C)(C)C)C4)ccc3n2C)cc2ccncc21]

Sodium hydrosulfite (162 mg, 0.793 mmol) dissolved in water (1 mL) was added to a solution of (R)-tert-butyl (1-(4-(methylamino)-3-nitrobenzoyl)piperidin-3-yl)carbamate (100 mg, 0.264 mmol) and 1-ethyl-1H-pyrrolo[2,3-c]pyridine-2-carbaldehyde (46.0 mg, 0.264 mmol) in ethanol (2 mL) at RT under nitrogen. The reaction mixture was heated to 100° C. in a microwave for 5 h. The reaction mixture was diluted with DCM (20 mL), sodium sulfate was added and the resultant suspension filtered and concentrated in vacuo to yield the crude product. This was purified by Biotage SP4 on a SNAP 10 g silica cartridge using a gradient of 0% (20% MeOH/DCM)/DCM→50% (20% MeOH/DCM)/DCM. Appropriate fractions were combined and evaporated under vacuum to give the title compound (42 mg) LCMS (Method A): Rt=0.71 min, MH+=503.3

Intermediate 27: tert-Butyl (1-(2-(1-ethyl-1H-pyrrolo[3,2-c]pyridin-2-yl)-1-methyl-1H-benzo[d]imidazole-5-carbonyl)piperidin-3-yl)carbamate

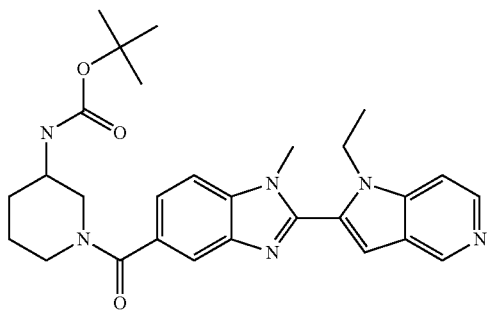 [SMILES: CCn1c(-c2nc3cc(C(=O)N4CCCC(NC(=O)OC(C)(C)C)C4)ccc3n2C)cc2cnccc21]

Sodium hydrosulfite (277.4 mg, 1.275 mmol) dissolved in water (1.5 mL) was added to a stirred solution of tert-butyl (1-(4-(methylamino)-3-nitrobenzoyl)piperidin-3-yl)carbamate (143.2 mg, 0.378 mmol) and 1-ethyl-1H-pyrrolo[3,2-c]pyridine-2-carbaldehyde (67.6 mg, 0.388 mmol) in ethanol (3.5 mL) at room temperature in a 5 ml microwave vial. The reaction mixture was then heated in a microwave for 5 hr at 100° C. Methanol was added to the reaction mixture and dried using Na$_2$SO$_4$. The reaction mixture was then filtered under gravity through a hydrophobic frit and the eluent collected and concentrated under vacuum. The crude product was dissolved in a minimum volume of DCM and purified using SP4 on a 25 g SNAP silica cartridge. The cartridge was eluted using a gradient of 0-100% 20% methanol in DCM/DCM. Appropriate fractions were collected and concentrated under vacuum to give the title compound as a yellow oil (76 mg).

LCMS (Method B): Rt=0.71 min, MH+=503.2

Intermediate 28: (R)-tert-Butyl (1-(1-methyl-2-(1-(2,2,2-trifluoroethyl)-1H-pyrrolo[2,3-b]pyridin-2-yl)-1H-benzo[d]imidazole-5-carbonyl)piperidin-3-yl)carbamate

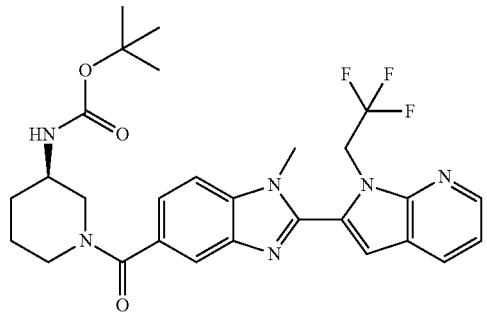 [SMILES: Cn1c(-c2cc3cccnc3n2CC(F)(F)F)nc2cc(C(=O)N3CCC[C@@H](NC(=O)OC(C)(C)C)C3)ccc21]

To a mixture of (R)-tert-butyl (1-(4-(methylamino)-3-nitrobenzoyl)piperidin-3-yl)carbamate (2.1 g, 5.55 mmol) and 1-(2,2,2-trifluoroethyl)-1H-pyrrolo[2,3-b]pyridine-2-carbaldehyde (1.3 g, 5.70 mmol) in ethanol (55 ml) was added portionwise a solution of sodium hydrosulfite (3.41 g, 16.65 mmol) in water (25 ml). The mixture was flushed with nitrogen and heated at 90° C. overnight for 17 hours. The reaction mixture was allowed to cool to room temperature and the solvent was evaporated in vacuo. DCM was added to the residue and the heterogeneous solution was dried over sodium sulfate. The solid was filtered off and the filtrate was concentrated under vacuo. The residue was loaded in dichloromethane and purified by SP4 SNAP on 2 silica (Si) 100 g columns using an initial gradient of 25-80% (15 CVs), followed by 80-100% (10 CVs) ethyl acetate/cyclohexane. The appropriate fractions were combined and evaporated in vacuo to give the title compound as a pale yellow solid (1.934 g).

LCMS (Method B): Rt=1.09 min, MH+=557.5

Intermediate 29: (R)-tert-Butyl (1-(2-(1-(cyclopropylmethyl)-1H-pyrrolo[2,3-b]pyridin-2-yl)-1-methyl-1H-benzo[d]imidazole-5-carbonyl)piperidin-3-yl)carbamate

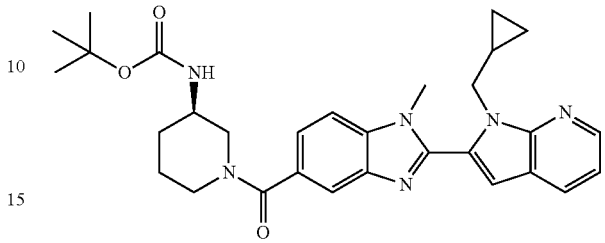

A solution of 1-(cyclopropylmethyl)-1H-pyrrolo[2,3-b]pyridine-2-carbaldehyde (2 g, 8.99 mmol) in ethanol (90 mL) was added to a round bottom flask containing (R)-tert-butyl (1-(4-(methylamino)-3-nitrobenzoyl)piperidin-3-yl)carbamate (3.4 g, 8.98 mmol) and the resulting solution stirred at room temperature. A solution of sodium dithionite (3.14 g, 15.33 mmol) in water (45 mL) was added portionwise to the reaction mixture. The reaction mixture was heated to 100° C. and stirred under nitrogen for 4 hours. The reaction mixture was concentrated under vacuum then diluted with DCM (150 ml) and water (150 ml). The organic layer was collected and the aqueous layer washed with DCM (3×100 ml). Organic layers were collected and backwashed with water (2×100 ml). The organic layer was collected, dried with Na$_2$SO$_4$, filtered through a hydrophobic frit and concentrated under vacuum to yield a crude product. This was dissolved in a minimum volume of DCM and purified using Biotage SP4 on a 100 g SNAP silica cartridge. The column was eluted with a gradient of 70-100% ethyl acetate in DCM for 10 CV. Appropriate fractions were collected and concentrated under vacuum. This was dried under vacuum to yield the title compound as a yellow solid (1.867 g).

LCMS (Method B): Rt=1.08 min, MH+=529.4

Intermediate 30: (R)-tert-Butyl (1-(2-(1-ethyl-5-methoxy-1H-pyrrolo[2,3-c]pyridin-2-yl)-1-methyl-1H-benzo[d]imidazole-5-carbonyl)piperidin-3-yl)carbamate

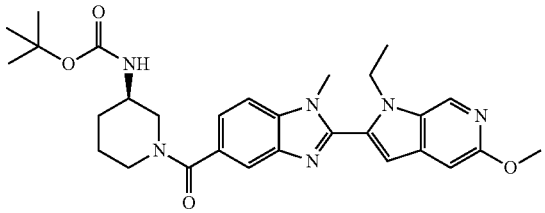 [SMILES: CCn1c(-c2nc3cc(C(=O)N4CCC[C@@H](NC(=O)OC(C)(C)C)C4)ccc3n2C)cc2cc(OC)ncc21]

1-Ethyl-5-methoxy-1H-pyrrolo[2,3-c]pyridine-2-carboxylic acid (200 mg, 0.908 mmol, reported in WO 2010/118208) and HATU (380 mg, 0.999 mmol) were dissolved in DMF (2 mL) and stirred at rt for 5 min. To this was added a solution of (R)-tert-butyl (1-(4-(methylamino)-3-nitrobenzoyl)piperidin-3-yl)carbamate (316 mg, 0.908 mmol) and DIPEA (0.476 ml, 2.72 mmol) in DMF (2 ml), and the resulting mixture stirred under nitrogen at rt for 3.5 hr. The reaction mixture was diluted with water (40 ml) and partitioned with ether (50 ml). The organic layer was isolated then the aqueous layer re-extracted with ether (2×50 ml). Combined organic layers were washed with water (2×30 ml) then dried over sodium sulfate then passed through a hydrophobic frit and concentrated under reduced pressure to give the crude amide intermediate as a blue solid. The solid was dried under reduced pressure overnight then dissolved in toluene (12.5 ml). Acetic acid (0.052 ml, 0.908 mmol) was added to the reaction mixture which was refluxed for 5 hr. Sodium bicarbonate (40 ml) was added to the reaction mixture and the organic layer isolated. The aqueous layer was reextracted with toluene (2×40 ml) and combined organic layers were concentrated under reduced pressure to give 238 mg of the crude product as a red-brown gum. The crude material was purified with column chromatography (eluted with 100% EtOAc) then further purified by high pH MDAP (Method E) to give the title compound as an off-white solid (106 mg, 22%).
LCMS (Method A): MH+=533.4, Rt=1.06 min Intermediate 31: (R)-tert-Butyl (1-(2-(1-ethyl-5-methoxy-1H-pyrrolo[2,3-b]pyridin-2-yl)-1-methyl-1H-benzo[d]imidazole-5-carbonyl)piperidin-3-yl)carbamate

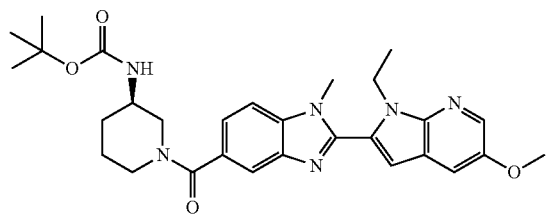 [SMILES: CCn1c(-c2nc3cc(C(=O)N4CCC[C@@H](NC(=O)OC(C)(C)C)C4)ccc3n2C)cc2cc(OC)cnc21]

Prepared similarly to intermediate 30 starting from 1-ethyl-5-methoxy-1H-pyrrolo[2,3-b]pyridine-2-carboxylic acid.
LCMS (Method A): Rt=1.10 min, MH+=533.3

Intermediate 32: (R)-tert-Butyl (1-(2-(1-ethyl-1H-pyrrolo[2,3-b]pyridin-2-yl)-7-methoxy-1-methyl-1H-benzo[d]imidazole-5-carbonyl)piperidin-3-yl)carbamate

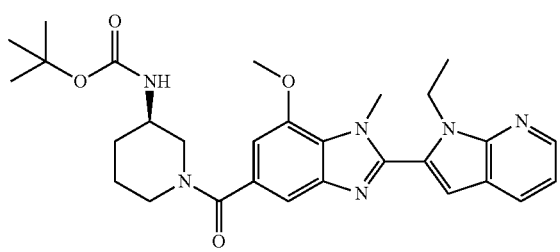 [SMILES: CCn1c(-c2nc3cc(C(=O)N4CCC[C@@H](NC(=O)OC(C)(C)C)C4)cc(OC)c3n2C)cc2cccnc21]

To a solution of (R)-tert-butyl (1-(3-methoxy-4-(methylamino)-5-nitrobenzoyl)piperidin-3-yl)carbamate (4.5 g, 11.02 mmol) and 1-ethyl-1H-pyrrolo[2,3-b]pyridine-2-carbaldehyde (2.015 g, 11.57 mmol) in ethanol (100 mL) was added portionwise a solution of sodium dithionite (4.25 g, 20.75 mmol) in water (50 mL). The mixture was flushed with nitrogen then heated at 100° C. overnight (16 hours). The reaction mixture was concentrated under vacuum then diluted with DCM (150 ml) and water (150 ml). The organic layer was collected and the aqueous layer washed with DCM (3×100 ml). Organic layers were combined and back washed with water (3×150 ml), collected, dried with Na$_2$SO$_4$, filtered through a hydrophobic frit and concentrated under vacuum to yield 5.5 g of crude product as white solid. The crude product was dissolved in a minimum volume of DCM and purified using Biotage SP4 on a SNAP 100 g silica cartridge. The column was eluted with a gradient of 70-100% ethyl acetate in DCM for 10 CV. Appropriate fractions were collected and concentrated in vacuo to afford the title compound as a white solid (4.40 g).
LCMS (Method B): Rt=1.05 min, MH+=533.4

Intermediate 33: (R)-tert-Butyl (1-(7-methoxy-1-methyl-2-(1-(2,2,2-trifluoroethyl)-1H-pyrrolo[2,3-b]pyridin-2-yl)-1H-benzo[d]imidazole-5-carbonyl)piperidin-3-yl)carbamate

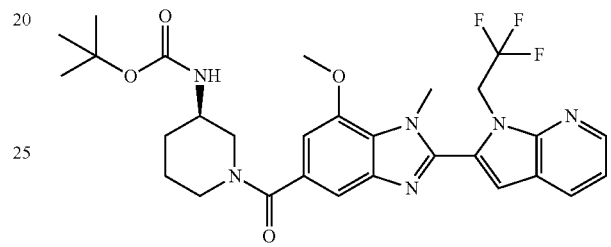

To a solution of (R)-tert-butyl (1-(3-methoxy-4-(methylamino)-5-nitrobenzoyl)piperidin-3-yl)carbamate (3.58 g, 8.76 mmol) and 1-(2,2,2-trifluoroethyl)-1H-pyrrolo[2,3-b]pyridine-2-carbaldehyde (2.61 g, 11.44 mmol) in ethanol (140 ml) was added portionwise a solution of sodium hydrosulfite (3.18 g, 15.53 mmol) in water (70 ml). The mixture was flushed with nitrogen then heated at 100° C. overnight (16 hours). The reaction mixture was concentrated under vacuum then diluted with DCM (150 ml) and water (150 ml). The organic layer was collected and the aqueous layer washed with DCM (3×100 ml). Organic layers were collected, dried with Na$_2$SO$_4$, filtered through a hydrophobic frit and concentrated under vacuum to yield 5.5 g of crude product as white solid. This was dissolved in a minimum volume of DCM and purified using Biotage SP4 on a 100 g SNAP silica cartridge. The column was eluted with a gradient of 70-100% ethyl acetate in DCM for 10 CV. Appropriate fractions were collected and concentrated under vacuum to yield the title compound as a white solid (4.31 g).
LCMS (Method B): Rt=1.17 min, MH+=587.4

Intermediate 34: (R)-tert-Butyl (1-(2-(1-(cyclopropylmethyl)-1H-pyrrolo[2,3-b]pyridin-2-yl)-7-methoxy-1-methyl-1H-benzo[d]imidazole-5-carbonyl)piperidin-3-yl)carbamate

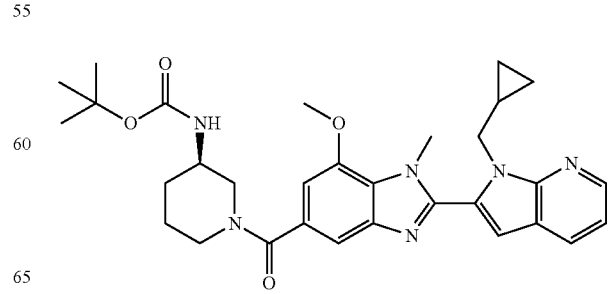

A solution of 1-(cyclopropylmethyl)-1H-pyrrolo[2,3-b]pyridine-2-carbaldehyde (0.743 g, 3.71 mmol) in ethanol (60 mL) was added to a round bottom flask containing (R)-tert-butyl (1-(3-methoxy-4-(methylamino)-5-nitrobenzoyl)piperidin-3-yl)carbamate (1.529 g, 3.74 mmol) and the resulting solution stirred at room temperature. A solution of sodium dithionite (1.375 g, 6.71 mmol) in water (30 mL) was added portionwise to the reaction mixture. The reaction mixture was heated to 100° C. and stirred under nitrogen for 4 hours. The reaction mixture was concentrated under vacuum then diluted with DCM (150 ml) and water (150 ml). The organic layer was collected and the aqueous layer washed with DCM (3×100 ml). Organic layers were collected, dried with Na$_2$SO$_4$, filtered through a hydrophobic frit and concentrated under vacuum to yield ~2 g of crude product as yellow solid. This was dissolved in a minimum volume of DCM and purified using Biotage SP4 on a 50 g SNAP silica cartridge. The column was eluted with a gradient of 70-100% ethyl acetate in DCM for 10 CV. Appropriate fractions were collected and concentrated under vacuum to yield the title compound as a yellow solid (1.55 g).

LCMS (Method B): Rt=1.15 min, MH+=559.4

Intermediate 35: tert-Butyl (1-(2-(1-ethyl-1H-pyrrolo[2,3-b]pyridin-2-yl)-1-methyl-1H-benzo[d]imidazole-5-carbonyl)piperidin-3-yl)carbamate

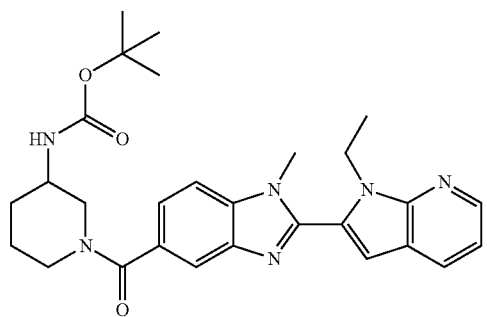 [SMILES: CCn1c(-c2nc3cc(C(=O)N4CCCC(NC(=O)OC(C)(C)C)C4)ccc3n2C)cc2cccnc21]

Sodium hydrosulfite (235 mg, 1.150 mmol) dissolved in water (1.500 mL) was added to a solution of tert-butyl (1-(4-(methylamino)-3-nitrobenzoyl)piperidin-3-yl)carbamate (145 mg, 0.383 mmol) and 1-ethyl-1H-pyrrolo[2,3-b]pyridine-2-carbaldehyde (66.7 mg, 0.383 mmol) in ethanol (3 mL) at RT under nitrogen. The reaction mixture was heated to 100° C. in a microwave for 5 h. The reaction mixture was diluted with DCM (20 mL), Na$_2$SO$_4$ was added and the resultant suspension filtered and concentrated in vacuo to yield the crude product as a yellow oil. The crude product was purified by Biotage SP4 on a SNAP 25 g silica cartridge using a gradient of 0% (20% MeOH/DCM)/DCM→100% (20% MeOH/DCM)/DCM. Appropriate fractions were combined and evaporated under vacuum to give the title compound as a yellow solid (104 mg).

LCMS (Method B): Rt=1.01 min, MH+=503.2

Intermediate 36: Benzyl 7-oxa-3-azabicyclo[4.1.0]heptane-3-carboxylate

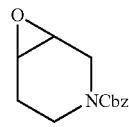

3-Chlorobenzoperoxoic acid (16.79 g, 97 mmol) was added portionwise under an atmosphere of nitrogen to a stirred solution of benzyl 5,6-dihydropyridine-1(2H)-carboxylate (15.1 g, 69.5 mmol) (available, for example, from Fluorochem) in anhydrous dichloromethane (DCM) (100 mL) cooled using an ice bath. The resulting mixture was allowed to reach rt and stirred for 18 h. Water (100 mL) was added to the reaction mixture and the layers were partitioned. The organic layer was added dropwise to a stirred 5% aqueous solution of NaS$_2$O$_5$ (200 mL). At the end of the addition, the mixture was stirred for a further 1 h, then the layers were separated and the aqueous layer was back extracted with DCM (50 mL×2). The organics were combined and washed with 5% aqueous K$_2$CO$_3$ solution (100 mL×3), followed by brine (100 mL). At this stage peroxide test showed there was still 25 mg/mL peroxide in the organic layer. The organics were therefore added to a stirred solution of 5% NaS$_2$O$_5$(aq) (200 mL) and the resultant biphasic mixture stirred for 1 h. Peroxide test now showed <0.5 mg/mL peroxide. The layers were separated and aqueous layer washed with further DCM (2×50 mL). The combined organics were then dried (Na$_2$SO$_4$). and concentrated in vacuo to afford the crude product as a pale-gold oil. The crude product was purified by silica gel chromatography, (340 g Si), eluting with 30→80% EtOAc/cyclohexane. The appropriate fractions were combined and concentrated in vacuo to afford the title compound as a colourless oil—benzyl 7-oxa-3-azabicyclo[4.1.0]heptane-3-carboxylate (12.75 g, 54.7 mmol, 79% yield).

LCMS (Method B): Rt=0.88 min, MH$^+$=234.2

Intermediate 37: trans-Benzyl 3-((tert-butoxycarbonyl)amino)-4-hydroxypiperidine-1-carboxylate

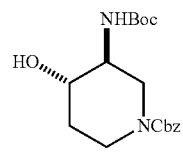

Three separate reactions were performed under the same reaction conditions outlined below. Where reagent/solvent quantities vary, the specific quantities used are outlined in the table. The crude material from the three reactions was combined for purification as indicated:

| Reagent/Solvent: | Reaction 1 | Reaction 2 | Reaction 3 |
|---|---|---|---|
| Benzyl 7-oxa-3-azabicyclo[4.1.0]heptane-3-carboxylate (A) | 4.37 g, 18.73 mmol | 4.45 g, 19.08 mmol | 3.94 g, 16.89 mmol |
| DCM (B) | 120 mL | 100 ml | 100 ml |
| Triethylamine (C) | 2.87 ml, 20.61 mmol | 2.92 ml, 20.98 mmol | 2.59 mL, 18.58 mmol |

| Reagent/Solvent: | Reaction 1 | Reaction 2 | Reaction 3 |
|---|---|---|---|
| Boc₂O (D) | 4.35 ml, 18.73 mmol | 4.43 ml, 19.08 mmol | 3.92 mL, 16.89 mmol |

A solution of benzyl 7-oxa-3-azabicyclo[4.1.0]heptane-3-carboxylate (A) in 25-30% ammonium hydroxide aqueous solution (150 ml, 3766 mmol) and ethanol (100 mL) was stirred in a HASTC alloy bomb at 70° C. for 5 h. The reaction mixture was transferred to a rb flask and concentrated in vacuo by half (caution large amount of NH₃ given off). The resultant solution was diluted with brine (50 mL) and the organics extracted into DCM (100 mL). Subsequently the aqueous layer was further extracted with 10% MeOH/DCM (3×50 mL). The combined organic layers were dried (Na₂SO₄) and concentrated in vacuo to give the intermediate primary amine as a yellow oil. The oily residue was diluted with dichloromethane (DCM) (B) and triethylamine (C) and Boc₂O (D) added dropwise. The reaction was allowed to stir for 2 h. LCMS showed complete reaction to two regiomeric products with similar Rt. The reaction mixture was quenched with sat. NH₄Cl (aq) (100 mL) and the layers separated. The aqueous was further extracted with DCM (2×75 mL). The combined organics were dried through a hydrophobic frit and the solvent was removed under vacuum to give a white gum.

The crude material from the three reactions was combined for purification: The combined residue was dissolved in DCM and split in two and purified by column chromatography on two 340 g silica cartridges, using a gradient of 0-100% ethyl acetate/cyclohexane. The appropriate fractions were combined and evaporated in vacuo to give two main products:
First eluting peak from column: trans-benzyl 4-((tert-butoxycarbonyl)amino)-3-hydroxypiperidine-1-carboxylate (10.492 g, 29.9 mmol, 59% yield) as a white solid (undesired regioisomer).
Second eluting peak from column: trans-benzyl 3-((tert-butoxycarbonyl)amino)-4-hydroxypiperidine-1-carboxylate (6.485 g, 18.51 mmol, 37% yield) as a white solid (desired regioisomer indicated above.)
LCMS (Method B): Rt=0.96 min, MH⁺=351.2

Intermediate 38: cis-Benzyl 4-(benzoyloxy)-3-((tert-butoxycarbonyl)amino)piperidine-1-carboxylate

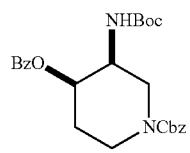

To a solution of triphenylphosphine (5.83 g, 22.24 mmol) in tetrahydrofuran (THF) (60 mL) was added DIAD (4.38 mL, 22.24 mmol) and the mixture was stirred in an ice-water bath for 15 min and then allowed to warm to rt. To the suspension was added a suspension of trans-benzyl 3-((tert-butoxycarbonyl)amino)-4-hydroxypiperidine-1-carboxylate (6.495 g, 18.54 mmol) in tetrahydrofuran (THF) (75 mL) followed by benzoic acid (2.72 g, 22.24 mmol). The reaction mixture cleared to a yellow solution and was stirred for 2 h. LCMS analysis showed product formation, however the SM peak was obscured by by-product so it was difficult to confirm reaction had gone to completion. The reaction was left to stir overnight (20 h). The reaction mixture was concentrated under vacuum. The residue was purified by silica chromotagraphy. The residue was loaded in DCM on a 340 g silica cartridge and purified using a 0-40% EtOAc/cyclohexane gradient. The appropriate fractions were combined and the evaporated in vacuo to give the crude product cis-benzyl 4-(benzoyloxy)-3-((tert-butoxycarbonyl)amino)piperidine-1-carboxylate (8.11 g, 17.84 mmol, 96% yield) as a pale yellow oil.
LCMS (Method B): Rt=1.27 min, MH⁺=455.3.

Intermediate 39: cis-Benzyl 3-((tert-butoxycarbonyl)amino)-4-hydroxypiperidine-1-carboxylate

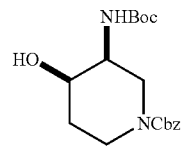

Intermediate 40: (3S,4R)-Benzyl 3-((tert-butoxycarbonyl)amino)-4-hydroxypiperidine-1-carboxylate

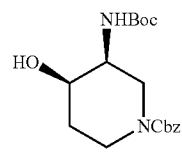 [SMILES: CC(C)(C)OC(=O)N[C@H]1CN(C(=O)OCc2ccccc2)CC[C@H]1O]

Intermediate 41: (3R,4S)-Benzyl 3-((tert-butoxycarbonyl)amino)-4-hydroxypiperidine-1-carboxylate

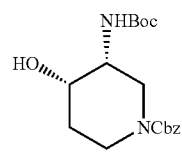

A solution of potassium carbonate (3.70 g, 26.8 mmol) in water (80 mL) was added to a solution of cis-benzyl 4-(benzoyloxy)-3-((tert-butoxycarbonyl)amino)piperidine-1-carboxylate (8.11 g, 17.84 mmol) in ethanol (160 mL) and the mixture was stirred at 70° C. for 20 h. The reaction mixture was concentrated in vacuo to ⅓rd volume and the resultant suspension was diluted with water (50 mL) and extracted using DCM (3×70 mL). The collected organics were combined and dried (Na₂SO₄) and concentrated in vacuo to afford the crude product as a colourless oil. The crude product was then purified by column chromatography on a silica cartridge (340 g) using a 0-100% ethyl acetate/cyclohexane gradient. The appropriate fractions were combined and evaporated in vacuo to give the required product cis-benzyl 3-((tert-butoxycarbonyl)amino)-4-hydroxypiperidine-1-carboxylate (5.54 g, 15.81 mmol, 89% yield) as a white foam.

LCMS (Method B): Rt=0.98 min, MH+=351.2
1 g of the racemic product was submitted for chiral purification using Chiral HPLC Method B. The isomers were successfully resolved:
Isomer 1, was obtained as a colourless oil—(3S,4R)-benzyl 3-((tert-butoxycarbonyl)amino)-4-hydroxypiperidine-1-carboxylate (405 mg, 1.156 mmol, 6.48% yield).
LCMS (Method B): Rt=0.97 min, MH+=351.2
Chiral HPLC (Method A): 100% ee.
Isomer 2, was obtained as a colourless oil—(3R,4S)-benzyl 3-((tert-butoxycarbonyl)amino)-4-hydroxypiperidine-1-carboxylate (411 mg, 1.173 mmol, 6.57% yield).
LCMS (Method B): Rt=0.99 min, MH+=351.2
Chiral HPLC (Method A): 95% ee.
The remaining 4.5 g of racemate was also submitted for chiral purification using Chiral HPLC Method C. The isomers were successfully resolved:
Isomer 1, was obtained as a colourless oil—(3S,4R)-benzyl 3-((tert-butoxycarbonyl)amino)-4-hydroxypiperidine-1-carboxylate (1.94 g, 5.54 mmol, 31.0% yield).
LCMS (Method B): Rt=0.98 min, MH+=351.2
Chiral HPLC (Method A): 98.7% ee.
Isomer 2, obtained as a colourless oil—(3R,4S)-benzyl 3-((tert-butoxycarbonyl)amino)-4-hydroxypiperidine-1-carboxylate (1.92 g, 5.48 mmol, 30.7% yield).
LCMS (Method B): Rt=0.97 min, MH+=351.1
Chiral HPLC (Method A): 96.3% ee.

Intermediate 42: tert-Butyl ((3S,4R)-4-hydroxypiperidin-3-yl)carbamate

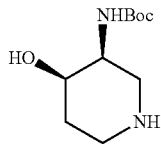 [SMILES: CC(C)(C)OC(=O)N[C@H]1CNCC[C@H]1O]

A solution of (3S,4R)-benzyl 3-((tert-butoxycarbonyl) amino)-4-hydroxypiperidine-1-carboxylate (1.94 g, 5.54 mmol) in ethanol (48 mL) was added to a hydrogenation flask containing 10% Pd/C (0.059 g, 0.554 mmol) that had been evacuated and back-filled with $N_2$ (×3). The flask was again evacuated and then back-filled with $H_2$ (×3). Enough $H_2$ to allow complete reaction was then introduced to a burette and the system closed and the flask allowed to stir under a $H_2$ atmosphere overnight. The reaction mixture was filtered through Celite and washed with EtOH (2×20 mL) and ethyl acetate (2×20 mL). The combined filtrate was concentrated in vacuo to afford the product as a cream oily solid—tert-butyl ((3S,4R)-4-hydroxypiperidin-3-yl)carbamate (1.13 g, 5.22 mmol, 94% yield).
LCMS (Method B): Rt=0.40 min, MH+=217.1

Intermediate 43: tert-Butyl ((3R,4S)-4-hydroxypiperidin-3-yl)carbamate

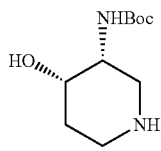

A solution of benzyl 3-((tert-butoxycarbonyl)amino)-4-hydroxypiperidine-1-carboxylate (141 mg, 0.402 mmol) in methanol (8.05 mL) was hydrogenated using the H-cube (settings: 25° C., full $H_2$ mode, 1 mL/min flow rate) and 10% Pd/C CatCart 30 as the catalyst. The eluent was evaporated in vacuo to give the required tert-butyl (4-hydroxypiperidin-3-yl)carbamate (85.1 mg, 0.393 mmol, 98% yield) as a clear oil.
$^1$H NMR (DMSO-d6, 393K): 5.60 (1H, br s, NH), 3.77 (1H, dt, CH), 3.45 (1H, ddd, CH), 2.80 (1H, ddd, C$\underline{H}_A$H$_B$), 2.72 (1H, dd, C$\underline{H}_A$H$_B$), 2.63 (1H, dd, CH$_A\underline{H}_B$), 2.55-2.48 (1H, obs, CH$_A\underline{H}_B$), 1.59-1.53 (2H, m, CH$_2$), 1.42 (9H, s, 3×CH$_3$).
Proof of Absolute Stereochemistry for Intermediates 42 and 43
The absolute configuration of intermediates 42 and 43 was assigned using ab initio VCD analysis. The confidence level for this assignment was estimated to be >99%.
Theoretical Analysis:
Conformational Search: MOE stochastic csearch using MMFF94x force field
Model Chemistry: # opt freq=(noraman,vcd) b3lyp/dgdzvp
Conformational Analysis: Fractional populations estimated using Boltzmann statistics
Lorentzian band width: 6 cm$^{-1}$
Frequency scale factor: 0.975
Estimation of Confidence Limit: CompareVOA (BioTools, Inc.) analysis
Experimental:
Spectrometer: BioTools Chiral/R-2X FT-VCD spectrometer operated at 4 cm$^{-1}$
Frequency Range: 2000-800 cm$^{-1}$
PEM Calibration: PEM calibrated at 1400 cm$^{-1}$
PEM Retardation Settings: PEM1=0.250*λ; PEM2=0.260*λ
Scan Method: single 4 h scan; total #=3120×4=12480 scans) scans; t~6 h.)
Solvent: CDCl$_3$
Concentrations: ~10 mg/250 uL
Baseline Correction Method: modified half-difference (VCDE1 (corr'd)=VCDE1 minus VCDE2; VCDE2 (corr'd) =VCDE2 minus VCDE1)
Additional Processing: Savitsky-Golay 9-point smooth
Estimated Level of Reliability
The confidence limit in this study was estimated using CompareVOA™ (BioTools, Inc.), an automated tool for quantifying the level of agreement between two sets of spectral data.
The degree of reliability (the confidence limit) is assessed using the absolute values of two parameters: total neighborhood similarity for the VCD correlation (TNS (VCD)) and the enantiomeric similarity index (ESI).
The degrees of reliability based on CompareVOA analysis are as follows:

| Reliability | *TNS (VCD) (range) | *ESI (range) | Confidence Limit (CL) (range) |
|---|---|---|---|
| High | ≥70 | ≥60 | >99% |
| Medium | 60-70 | 50-60 | 95-99% |
| Low | 50-60 | 40-50 | 90-95% |
| Unreliable | <50 | <40 | <90% |

*absolute value

CompareVOA Results: Spectral Range: 1760-950 cm$^{-1}$
Region omitted: none
Range of statistical analysis (minimum 400 cm$^{-1}$): 810 cm$^{-1}$ Width of triangular weighting function: 20 cm$^{-1}$
TNS (VCD): 85.1 (absolute value)
ESI: 82.8 (absolute value)
Optimized scale factor: 0.975
Estimated confidence level: >99%

Intermediate 44: Methyl 2-(1-(cyclopropylmethyl)-1H-pyrrolo[2,3-b]pyridin-2-yl)-7-methoxy-1-methyl-1H-benzo[d]imidazole-5-carboxylate

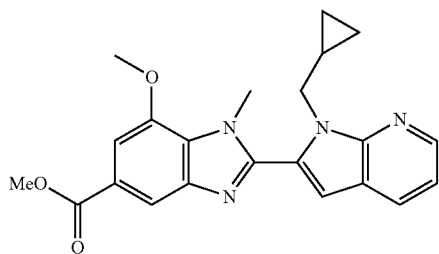 [SMILES: COC(=O)c1cc(OC)c2c(c1)nc(-c1cc3cccnc3n1CC1CC1)n2C]

A solution of sodium hydrosulfite (512 mg, 2.498 mmol) in water (3.25 mL) was added to a solution of methyl 3-methoxy-4-(methylamino)-5-nitrobenzoate (200 mg, 0.833 mmol) and 1-(cyclopropylmethyl)-1H-pyrrolo[2,3-b]pyridine-2-carbaldehyde (167 mg, 0.833 mmol) in ethanol (6.5 mL) in a microwave vial. The reaction mixture was heated in the microwave for 5 h at 100° C. The reaction mixture was diluted with DCM (20 mL), dried (Na$_2$SO$_4$), filtered and concentrated in vacuo to afford the crude product as a colourless oil. The crude product was purified by column chromatography on a silica cartridge (25 g) using a gradient of 60% EtOAc/cyclohexane→100% EtOAc/cyclohexane. (The product eluted near the solvent front). The appropriate fractions were combined and evaporated under vacuum to give the product as a yellow oil—methyl 2-(1-(cyclopropylmethyl)-1H-pyrrolo[2,3-b]pyridin-2-yl)-7-methoxy-1-methyl-1H-benzo[d]imidazole-5-carboxylate (260 mg, 0.666 mmol, 80% yield) LCMS (Method B): Rt=1.17 mins, MH$^+$=391.3.

Intermediate 45: Methyl 2-(1-(cyclopropylmethyl)-1H-pyrrolo[2,3-b]pyridin-2-yl)-1-methyl-1H-benzo[d]imidazole-5-carboxylate

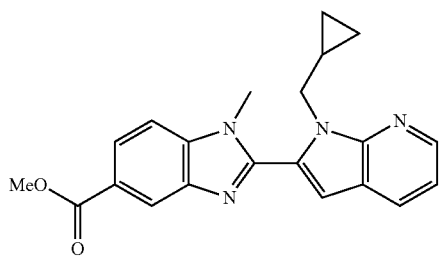 [SMILES: COC(=O)c1ccc2c(c1)nc(-c1cc3cccnc3n1CC1CC1)n2C]

Prepared in a similar manner to Intermediate 44 using methyl 4-(methylamino)-3-nitrobenzoate (89 mg, 0.424 mmol) and 1-(cyclopropylmethyl)-1H-pyrrolo[2,3-b]pyridine-2-carbaldehyde (85 mg, 0.424 mmol).
LCMS (Method B): Rt=1.05 mins, MH$^+$=361.1

Intermediate 46: 2-(1-(Cyclopropylmethyl)-1H-pyrrolo[2,3-b]pyridin-2-yl)-7-methoxy-1-methyl-1H-benzo[d]imidazole-5-carboxylic acid

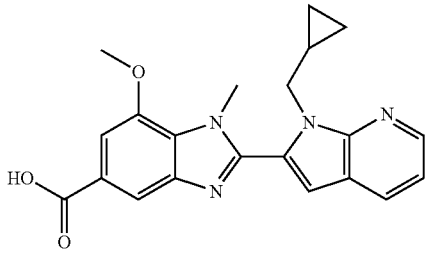 [SMILES: COc1cc(C(=O)O)cc2nc(-c3cc4cccnc4n3CC3CC3)n(C)c12]

Methyl 2-(1-(cyclopropylmethyl)-1H-pyrrolo[2,3-b]pyridin-2-yl)-7-methoxy-1-methyl-1H-benzo[d]imidazole-5-carboxylate (260 mg, 0.666 mmol) was dissolved in a 1:1 ratio of tetrahydrofuran (THF) (3.2 mL) and water (3.2 mL). To this was added lithium hydroxide monohydrate (140 mg, 3.33 mmol) and the reaction stirred at rt for 16 h. The reaction mixture was acidified by the addition of 2M HCl (aq) (20 mL) and the organics extracted into 10% MeOH/DCM (20 mL). The aqueous layer was washed with 10% MeOH/DCM (2×20 mL) and the combined organics dried (Na$_2$SO$_4$) and concentrated in vacuo to afford a yellow oil which solidified on standing (44 mg). Due to the poor recovery it was assumed the remainder of the product remained in the aqueous layer. The aqueous layer was further extracted with EtOAc (20 mL), DCM (2×20 mL) and 10% MeOH/DCM (8×10 mL). The combined organics were dried (Na$_2$SO$_4$) and concentrated in vacuo. Both crude products were combined together to form 2-(1-(cyclopropylmethyl)-1H-pyrrolo[2,3-b]pyridin-2-yl)-7-methoxy-1-methyl-1H-benzo[d]imidazole-5-carboxylic acid (105 mg, 0.279 mmol, 41.9% yield).

LCMS (Method B): Rt=1.00 mins, MH$^+$=377.1.

Intermediate 47: 2-(1-(Cyclopropylmethyl)-1H-pyrrolo[2,3-b]pyridin-2-yl)-1-methyl-1H-benzo[d]imidazole-5-carboxylic acid

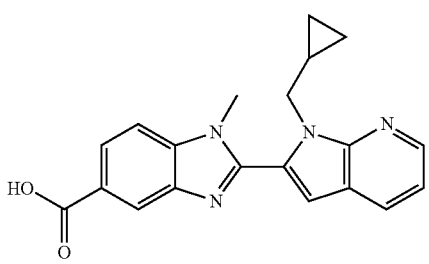 [SMILES: Cn1c(-c2cc3cccnc3n2CC2CC2)nc2cc(C(=O)O)ccc21]

Prepared in a similar manner to Intermediate 46 from methyl 2-(1-(cyclopropylmethyl)-1H-pyrrolo[2,3-b]pyridin-2-yl)-1-methyl-1H-benzo[d]imidazole-5-carboxylate (111 mg, 0.308 mmol).

LCMS (Method B): Rt=0.90 mins, MH$^+$=347.1

Intermediate 48: tert-Butyl ((3S,4R)-1-(2-(1-(cyclopropylmethyl)-1H-pyrrolo[2,3-b]pyridin-2-yl)-7-methoxy-1-methyl-1H-benzo[d]imidazole-5-carbonyl)-4-hydroxypiperidin-3-yl)carbamate

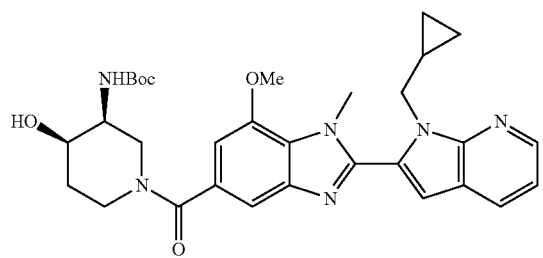 [SMILES: COc1cc(C(=O)N2CC[C@@H](O)[C@@H](NC(=O)OC(C)(C)C)C2)cc2nc(-c3cc4cccnc4n3CC3CC3)n(C)c12]

To a solution of 2-(1-(cyclopropylmethyl)-1H-pyrrolo[2,3-b]pyridin-2-yl)-7-methoxy-1-methyl-1H-benzo[d]imidazole-5-carboxylic acid (105 mg, 0.279 mmol) in DMF (1.5 mL) was added HATU (106 mg, 0.279 mmol) followed by DIPEA (0.097 mL, 0.558 mmol) and the reaction stirred at room temperature for 15 min. tert-Butyl ((3S,4R)-4-hydroxypiperidin-3-yl)carbamate (60.3 mg, 0.279 mmol) was added in DMF (1.5 mL) and the reaction stirred at RT for 16 h. LCMS showed complete reaction. Water (20 mL) and Et$_2$O (20 mL) were added and the layers separated. The aqueous layer was extracted with further Et$_2$O (2×20 mL) and the combined organics washed with water (2×20 mL), dried (Na$_2$SO$_4$) and concentrated in vacuo to afford a yellow oil. The crude product was purified by flash chromatography on silica (10 g) using a gradient of DCM→100% (20% MeOH/DCM)/DCM. The appropriate fractions were combined and evaporated under vacuum to give the product as a yellow oil—tert-butyl ((3S,4R)-1-(2-(1-(cyclopropylmethyl)-1H-pyrrolo[2,3-b]pyridin-2-yl)-7-methoxy-1-methyl-1H-benzo[d]imidazole-5-carbonyl)-4-hydroxypiperidin-3-yl)carbamate (146 mg, 0.254 mmol, 91% yield).
LCMS (Method B): Rt=1.03 min, MH+=575.3

Intermediate 49: tert-butyl ((3S,4R)-1-(2-(1-(cyclopropylmethyl)-1H-pyrrolo[2,3-b]pyridin-2-yl)-1-methyl-1H-benzo[d]imidazole-5-carbonyl)-4-hydroxypiperidin-3-yl)carbamate

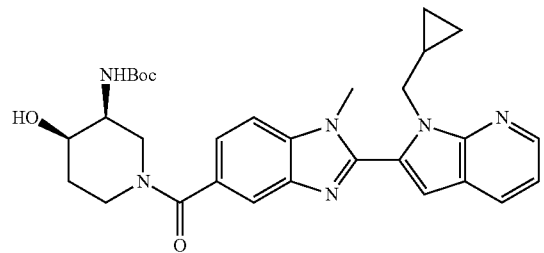 [SMILES: Cn1c(-c2cc3cccnc3n2CC2CC2)nc2cc(C(=O)N3CC[C@@H](O)[C@@H](NC(=O)OC(C)(C)C)C3)ccc21]

Prepared in a similar manner to Intermediate 48 from (2-(1-(cyclopropylmethyl)-1H-pyrrolo[2,3-b]pyridin-2-yl)-1-methyl-1H-benzo[d]imidazole-5-4-carboxylic acid and tert-butyl ((3S,4R)-4-hydroxypiperidin-3-yl)carbamate.
LCMS (Method B): Rt=0.94 mins, MH$^+$=545.2.

| | | |
|---|---|---|
| Intermediate 50 | 1-Neopentyl-1H-pyrrolo[2,3-b]pyridine-2-carbaldehyde | Prepared in a similar manner to Intermediate 13 from 1H-pyrrolo[2,3-b]pyridine-2-carbaldehyde and neopentyl bromide. LCMS (Method B): Rt = 1.14 mins, MH$^+$ = 217.2 |
| Intermediate 51 | 1-(2-Methylbutyl)-1H-pyrrolo[2,3-b]pyridine-2-carbaldehyde | Prepared in a similar manner to Intermediate 13 from 1H-pyrrolo[2,3-b]pyridine-2-carbaldehyde and bromo-2-methylbutane. LCMS (Method B): Rt = 1.15 mins, MH$^+$ = 217.2. |
| Intermediate 52 | 1-Isobutyl-1H-pyrrolo[2,3-b]pyridine-2-carbaldehyde | Prepared in a similar manner to Intermediate 13 from 1H-pyrrolo[2,3-b]pyridine-2-carbaldehyde and 1-bromo-2-methylpropane. LCMS (Method B): Rt = 1.06 mins, MH$^+$ = 203.1. |
| Intermediate 53 | 1-(2-Methoxy-2-methylpropyl)-1H-pyrrolo[2,3-b]pyridine-2-carbaldehyde | Prepared in a similar manner to Intermediate 13 from 1H-pyrrolo[2,3-b]pyridine-2-carbaldehyde and 1-bromo-2-methoxy-2-methylpropane. LCMS (Method B): Rt = 0.92 mins, MH$^+$ = 253.2 |
| Intermediate 54 | 4-Chloro-3-methoxy-5-nitrobenzoic acid | Prepared in a similar manner to Intermediate 19 from methyl 4-chloro-3-methoxy-5-nitrobenzoate. LCMS (Method B): Rt = 0.86 mins, MH$^+$ = 230.0 (ES$^-$) |
| Intermediate 55 | R)-tert-Butyl (1-(4-chloro-3-methoxy-5-nitrobenzoyl)piperidin-3-yl)carbamate | Prepared in a similar manner to Intermediate 20 from 4-chloro-3-methoxy-5-nitrobenzoic acid. LCMS (Method B): Rt = 1.08 mins, MH$^+$ = 414.1 |

Intermediate 56: (R)-tert-Butyl (1-(3-methoxy-4-((2-methoxyethyl)amino)-5-nitrobenzoyl)piperidin-3-yl)carbamate 2-Methoxyethylamine (0.15 mL, 1.741 mmol) was added to a stirred solution of (R)-tert-butyl (1-(4-chloro-3-methoxy-5-nitrobenzoyl)piperidin-3-yl)carbamate (280 mg, 0.406 mmol) in N,N-dimethylformamide (DMF) (1.5 mL) at rt under nitrogen. The reaction mixture was heated to 80° C. and stirred under nitrogen overnight (16 h). LC/MS showed that the desired product had formed with 55% purity. Water (75 mL) and diethyl ether (75 mL) were added to the reaction mixture and the layers separated. The aqueous layer was further extracted with diethyl ether (2×50 mL). The organic layers were collected, dried (Na$_2$SO$_4$), passed through a hydrophobic frit and concentrated under vacuum to afford 330 mg of crude product as an orange oil. The crude product was dissolved in a minimum volume of DCM and purified by column chromatography (25 g silica). The column was eluted with a gradient of 60-100% ethyl acetate/cyclohexane. TLC was used to determine product fractions and the appropriate fractions were collected and concentrated under vacuum to afford—(R)-tert-butyl (1-(3-methoxy-4-((2-methoxyethyl)amino)-5-nitrobenzoyl)piperidin-3-yl)carbamate (165.7 mg, 0.366 mmol, 90% yield) LCMS (Method B): Rt=1.04 mins, MH$^+$=453.3

Intermediate 60: 5-Bromo-2-(1-ethyl-1H-pyrrolo[2,3-b]pyridin-2-yl)-1-methyl-7-(trifluoromethoxy)-1H-benzo[d]imidazole To a solution of 4-bromo-N-methyl-2-nitro-6-(trifluoromethoxy)aniline (1.368 g, 4.34 mmol) and 1-ethyl-1H-pyrrolo[2,3-b]pyridine-2-carbaldehyde (0.756 g, 4.34 mmol) in ethanol (20 mL) was added sodium dithionite (2.67 g, 13.03 mmol) in water (10 mL). The mixture was flushed with nitrogen and then heated to 80° C. with stirring for 17 h. LCMS showed ~52% conversion to the desired product with no starting material remaining. The reaction mixture was partitioned between aqueous hydrochloric acid (0.25 M, 100 mL) and extracted with dichloromethane (3×100 mL). The organics were combined, dried using a hydrophobic frit and evaporated under vacuum to give the crude product as a yellow solid. The sample was loaded in dichloromethane and purified by column chromatography on silica (100 g) using a gradient of 0-30% cyclohexane-

| Intermediate 57 | (R)-tert-Butyl (1-(4-(isobutylamino)-3-methoxy-5-nitrobenzoyl)piperidin-3-yl)carbamate | Prepared similarly to Intermediate 56 from tert-butylamine and (R)-tert-butyl (1-(4-chloro-3-methoxy-5-nitrobenzoyl)piperidin-3-yl)carbamate. LCMS (Method B): Rt = 1.23 mins, MH$^+$ = 451.3 |
| --- | --- | --- |
| Intermediate 58 | (S)-tert-Butyl (1-(3-methoxy-4-(methylamino)-5-nitrobenzoyl)piperidin-3-yl)carbamate | Prepared in a similar manner to Intermediate 20 from 3-methoxy-4-(methylamino)-5-nitrobenzoic acid. LCMS (Method B): Rt = 1.02 mins, MH$^+$ = 409.2 |

Intermediate 59: 4-Bromo-N-methyl-2-nitro-6-(trifluoromethoxy)aniline

A solution of 4-bromo-2-nitro-6-(trifluoromethoxy)aniline (1.962 g, 6.52 mmol, commercially available from, for example, Apollo Scientific) in N,N-dimethylformamide (DMF) (80 mL) was cooled with an ice/water bath to ~0° C. for 10 min. Cesium carbonate (4.25 g, 13.04 mmol) was then added and stirred, and the colour changed from yellow to red. After 10 min, methyl iodide (0.408 mL, 6.52 mmol) was added and the mixture was allowed to return to rt with stirring under nitrogen for 3 h. LCMS showed ~90% conversion to the desired product with no starting material remaining, and ~10% formation of an impurity. The reaction mixture was partitioned using water (400 mL) and EtOAc (400 mL), and the aqueous layer re-extracted with EtOAc (2×400 mL). The combined organics were backwashed with water (400 mL) and then passed through a hydrophobic frit and concentrated in vacuo to give the crude product as a yellow oil. The sample was loaded in dichloromethane and purified on silica (Si) (100 g) using 100% cyclohexane. The appropriate fractions were combined and evaporated in vacuo to give the required product (1.368 g, 67%) as an orange solid.

LCMS (Method A): Rt=1.33 min, MH$^+$=314.9 ethyl acetate. The appropriate fractions were combined and evaporated in vacuo to give the required product (628 mg, 33%) as a yellow gum which solidified.

LCMS (Method A): Rt=1.46 min, MH+=439.1

Intermediate 61: Methyl 2-(1-ethyl-1H-pyrrolo[2,3-b]pyridin-2-yl)-1-methyl-7-(trifluoromethoxy)-1H-benzo[d]imidazole-5-carboxylate 5-Bromo-2-(1-ethyl-1H-pyrrolo[2,3-b]pyridin-2-yl)-1-methyl-7-(trifluoromethoxy)-1H-benzo[d]imidazole (314 mg, 0.715 mmol), molybdenum hexacarbonyl (94 mg, 0.357 mmol), methanol (0.434 mL, 10.72 mmol), DIPEA (0.250 mL, 1.430 mmol), DMAP (175 mg, 1.430 mmol) and trans-bis(acetato)bis[o-(di-o-tolylphosphino)benzyl]dipalladium(II) (34 mg, 0.036 mmol) were dissolved in 1,4-dioxane (12 mL) in a microwave vial. The reaction vessel was sealed and heated in Biotage Initiator microwave to 190° C. for 2 h. After allowing the reaction mixture to cool, LCMS showed ~37% conversion to the desired product, as well as ~12% conversion to the hydrolysed product. The reaction mixture was concentrated in vacuo to give the crude product, methyl 2-(1-ethyl-1H-pyrrolo[2,3-b]pyridin-2-yl)-1-methyl-7-(trifluoromethoxy)-1H-benzo[d]imidazole-5-carboxylate (512 mg, 1.224 mmol, 171% yield) as a brown gum which was used without further purification.

LCMS (Method A): Rt=1.32 mins, MH$^+$=419.2.

| | | |
|---|---|---|
| Intermediate 62 | 2-(1-Ethyl-1H-pyrrolo[2,3-b]pyridin-2-yl)-1-methyl-7-(trifluoromethoxy)-1H-benzo[d]imidazole-5-carboxylic acid | Prepared from methyl 2-(1-ethyl-1H-pyrrolo[2,3-b]pyridin-2-yl)-1-methyl-7-(trifluoromethoxy)-1H-benzo[d]imidazole-5-carboxylate in a similar manner to Intermediate 46. LCMS (Method B): Rt = 1.05 mins, MH$^+$ = 405.1 |
| Intermediate 63 | (R)-tert-Butyl (1-(2-(1-ethyl-1H-pyrrolo[2,3-b]pyridin-2-yl)-1-methyl-7-(trifluoromethoxy)-1H-benzo[d]imidazole-5-carbonyl)piperidin-3-yl)carbamate | Prepared from 2-(1-ethyl-1H-pyrrolo[2,3-b]pyridin-2-yl)-1-methyl-7-(trifluoromethoxy)-1H-benzo[d]imidazole-5-carboxylic acid (236 mg, 0.584 mmol) and (R)-tert-butyl piperidin-3-ylcarbamate in a similar manner to Intermediate 48. LCMS (Method A): Rt = 1.28 mins, MH$^+$ = 587.4 |
| Intermediate 64 | (R)-tert-Butyl (1-(7-methoxy-1-methyl-2-(1-neopentyl-1H-pyrrolo[2,3-b]pyridin-2-yl)-1H-benzo[d]imidazole-5-carbonyl)piperidin-3-yl)carbamate | Prepared in a similar manner to Intermediate 29 from (R)-tert-butyl (1-(3-methoxy-4-(methylamino)-5-nitrobenzoyl)piperidin-3-yl)carbamate and 1-neopentyl-1H-pyrrolo[2,3-b]pyridine-2-carbaldehyde in a Biotage Initiator microwave at 100° C. for 5 hours. LCMS (Method B): Rt = 1.23 mins, MH$^+$ = 575.3. |
| Intermediate 65 | tert-Butyl ((3R)-1-(7-methoxy-1-methyl-2-(1-(2-methylbutyl)-1H-pyrrolo[2,3-b]pyridin-2-yl)-1H-benzo[d]imidazole-5-carbonyl)piperidin-3-yl)carbamate | Prepared in a similar manner to Intermediate 64 from (R)-tert-butyl (1-(3-methoxy-4-(methylamino)-5-nitrobenzoyl)piperidin-3-yl)carbamate and 1-(2-methylbutyl)-1H-pyrrolo[2,3-b]pyridine-2-carbaldehyde. LCMS (Method B): Rt = 1.23 mins, MH$^+$ = 575.4 |
| Intermediate 66 | (R)-tert-Butyl (1-(2-(1-ethyl-1H-pyrrolo[2,3-b]pyridin-2-yl)-7-methoxy-1-(2-methoxyethyl)-1H-benzo[d]imidazole-5-carbonyl)piperidin-3-yl)carbamate | Prepared in a similar manner to Intermediate 64 from (R)-tert-butyl (1-(3-methoxy-4-((2-methoxyethyl)amino)-5-nitrobenzoyl)piperidin-3-yl)carbamate and 1-ethyl-1H-pyrrolo[2,3-b]pyridine-2-carbaldehyde. LCMS (Method A): Rt = 1.14 mins, MH$^+$ = 577.4 |
| Intermediate 67 | (R)-tert-Butyl (1-(2-(1-ethyl-1H-pyrrolo[2,3-b]pyridin-2-yl)-1-isobutyl-7-methoxy-1H-benzo[d]imidazole-5-carbonyl)piperidin-3-yl)carbamate | Prepared in a similar manner to intermediate 65 from (R)-tert-butyl (1-(4-isobutylamino)-3-methoxy-5-nitrobenzoyl)piperidin-3-yl)carbamate and 1-ethyl-1H-pyrrolo[2,3-b]pyridine-2-carbaldehyde in 67% yield. LCMS (Method B): Rt = 1.22 mins, MH$^+$ = 575.4 |
| Intermediate 68 | (S)-tert-Butyl (1-(2-(1-ethyl-1H-pyrrolo[2,3-b]pyridin-2-yl)-7-methoxy-1-methyl-1H-benzo[d]imidazole-5-carbonyl)piperidin-3-yl)carbamate | Prepared in a similar manner to Intermediate 29 from (S)-tert-butyl (1-(3-methoxy-4-(methylamino)-5-nitrobenzoyl)piperidin-3-yl)carbamate and 1-ethyl-1H-pyrrolo[2,3-b]pyridine-2-carbaldehyde. LCMS (Method B): Rt = 1.07 mins, MH$^+$ = 533.4 |
| Intermediate 69 | (R)-tert-Butyl (1-(7-methoxy-2-(1-(2-methoxy-2-methylpropyl)-1H-pyrrolo[2,3-b]pyridin-2-yl)-1-methyl-1H-benzo[d]imidazole-5-carbonyl)piperidin-3-yl)carbamate | Prepared in a similar manner to Intermediate 29 from (R)-tert-butyl (1-(3-methoxy-4-(methylamino)-5-nitrobenzoyl)piperidin-3-yl)carbamate and 1-(2-methoxy-2-methylpropyl)-1H-pyrrolo[2,3-b]pyridine-2-carbaldehyde. LCMS |

| | | |
|---|---|---|
| | | (Method B): Rt = 1.08 mins, MH+ = 591.3 |
| Intermediate 70 | (R)-tert-Butyl (1-(2-(1-isobutyl-1H-pyrrolo[2,3-b]pyridin-2-yl)-7-methoxy-1-methyl-1H-benzo[d]imidazole-5-carbonyl)piperidin-3-yl)carbamate | Prepared in a similar manner to Intermediate 29 from (R)-tert-butyl (1-(3-methoxy-4-(methylamino)-5-nitrobenzoyl)piperidin-3-yl)carbamate and 1-isobutyl-1H-pyrrolo[2,3-b]pyridine-2-carbaldehyde. LCMS (Method B): Rt = 1.17 mins, MH+ = 561.3. |

Intermediate 71: tert-Butyl ((cis)-1-(2-(1-(cyclopropylmethyl)-1H-pyrrolo[2,3-b]pyridin-2-yl)-7-methoxy-1-methyl-1H-benzo[d]imidazole-5-carbonyl)-6-methylpiperidin-3-yl)carbamate (This is an Unknown Single Enantiomer with Cis-Relative Stereochemistry, Enantiomer of Intermediate 72)

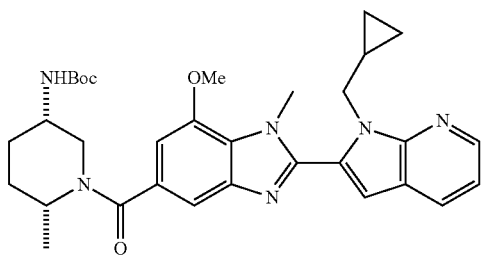 [SMILES: COc1cc(C(=O)N2C[C@@H](NC(=O)OC(C)(C)C)CC[C@H]2C)cc2nc(-c3cc4cccnc4n3CC3CC3)n(C)c12]

Intermediate 72: tert-Butyl ((cis)-1-(2-(1-(cyclopropylmethyl)-1H-pyrrolo[2,3-b]pyridin-2-yl)-7-methoxy-1-methyl-1H-benzo[d]imidazole-5-carbonyl)-6-methylpiperidin-3-yl)carbamate (Enantiomer of Intermediate 71 with Cis-Relative Stereochemistry)

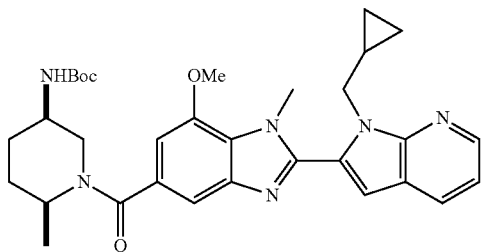 [SMILES: COc1cc(C(=O)N2C[C@H](NC(=O)OC(C)(C)C)CC[C@@H]2C)cc2nc(-c3cc4cccnc4n3CC3CC3)n(C)c12]

To a solution of 2-(1-(cyclopropylmethyl)-1H-pyrrolo[2,3-b]pyridin-2-yl)-7-methoxy-1-methyl-1H-benzo[d]imidazole-5-carboxylic acid (250 mg, 0.498 mmol) in DMF (2.3 mL) was added HATU (189 mg, 0.498 mmol) followed by DIPEA (0.174 mL, 0.996 mmol) and the reaction stirred at room temperature for 15 min. tert-Butyl (6-methylpiperidin-3-yl)carbamate (107 mg, 0.498 mmol) was added in DMF (2.3 mL) and the reaction stirred at rt for 16 h. Water (20 mL) and Et₂O (20 mL) were added and the layers separated. The aqueous layer was extracted with further Et₂O (2×20 mL) and the combined organics washed with water (2×20 mL), dried (Na₂SO₄) and concentrated in vacuo to afford a yellow oil. The crude product was purified by flash chromatography on silica (25 g) using a gradient of DCM→100% (20% MeOH/DCM)/DCM. The appropriate fractions were combined and evaporated under vacuum to give the product as a yellow oil. This material was purified further by high pH MDAP (Method E). Accordingly, the sample (160 mg) was dissolved in DMSO/MeOH (1:1, 1.8 mL) and injected in two batches. The appropriate fractions were collected and concentrated in vacuo to afford a white solid—tert-butyl (1-(2-(1-(cyclopropylmethyl)-1H-pyrrolo[2,3-b]pyridin-2-yl)-7-methoxy-1-methyl-1H-benzo[d]imidazole-5-carbonyl)-6-methylpiperidin-3-yl)carbamate (93 mg, 0.162 mmol, 32.6% yield). This material was sent for chiral resolution. 4 components were successfully resolved. However analysis showed only 1-2% of the presumed minor diastereomers. The mixture was submitted for chiral preparative chromatography (Chiral Method D) and only the two major components were collected:

Intermediate 71: Isomer 1: tert-butyl ((cis)-1-(2-(1-(cyclopropylmethyl)-1H-pyrrolo[2,3-b]pyridin-2-yl)-7-methoxy-1-methyl-1H-benzo[d]imidazole-5-carbonyl)-6-methylpiperidin-3-yl)carbamate (50 mg, 0.087 mmol, 17.53% yield) LCMS (Method B): Rt=1.19 min, MH+=573.4

Intermediate 72: Isomer 2: tert-butyl ((cis)-1-(2-(1-(cyclopropylmethyl)-1H-pyrrolo[2,3-b]pyridin-2-yl)-7-methoxy-1-methyl-1H-benzo[d]imidazole-5-carbonyl)-6-methylpiperidin-3-yl)carbamate (47 mg, 0.082 mmol, 16.48% yield) LCMS (Method B): Rt=1.19 min, MH+=573.4.

EXAMPLES

Example 1: 1-{[2-(1-Ethyl-1H-pyrrolo[3,2-c]pyridin-2-yl)-1-methyl-1H-benzimidazol-5-yl]carbonyl}-3-piperidinamine

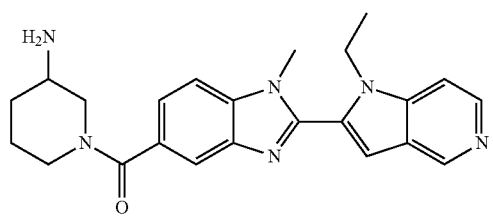 [SMILES: CCn1c(-c2nc3cc(C(=O)N4CCCC(N)C4)ccc3n2C)cc2cnccc21]

TFA (0.25 mL, 3.24 mmol) was added to a stirred solution of tert-butyl (1-(2-(1-ethyl-1H-pyrrolo[3,2-c]pyridin-2-yl)-1-methyl-1H-benzo[d]imidazole-5-carbonyl)piperidin-3-yl) carbamate (72.8 mg, 0.145 mmol) in dichloromethane (DCM) (3 mL) at room temperature and left stirring for 1 hour 30 minutes. The reaction mixture was concentrated under vacuum. The concentrated mixture was dissolved in methanol loaded onto a 5 g SCX column. The column was eluted with methanol (3 CV) and then the product was eluted as a free base with 2M ammonia in methanol (3 CV). Product fractions were collected and concentrated under vacuum and then dried in a vacuum oven at 40° C. to give a yellow solid (56 mg).
LCMS (Method A): Rt=0.71 min, MH+=403.3

Example 2A: (R)-(3-Aminopiperidin-1-yl)(2-(1-ethyl-1H-pyrrolo[2,3-b]pyridin-2-yl)-1-methyl-1H-benzo[d]imidazol-5-yl)methanone

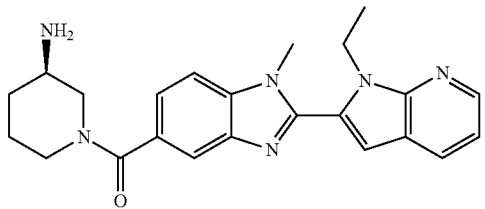 [SMILES: CCn1c(-c2nc3cc(C(=O)N4CCC[C@@H](N)C4)ccc3n2C)cc2cccnc21]

A solution of sodium hydrosulfite (353 mg, 1.722 mmol) in water (1.5 ml) was added to a solution of (R)-tert-butyl (1-(4-(methylamino)-3-nitrobenzoyl)piperidin-3-yl)carbamate (261 mg, 0.689 mmol) and 1-ethyl-1H-pyrrolo[2,3-b]pyridine-2-carbaldehyde (100 mg, 0.574 mmol) in ethanol (3.5 ml) in a 5 ml microwave vial. The reaction mixture was heated in the microwave for 5 hours at 100° C. Methanol was added to the reaction mixture. The reaction mixture was dried using Na$_2$SO$_4$. This mixture was then filtered under vacuum. The crude product was loaded in DCM, onto a 50 g SNAP Si-cartridge, purified by SP4, eluting with 0-5% methanol in DCM (15 CV). The appropriate fractions were combined and the solvent was evaporated under vacuo to give an impure product. This was further purified by SP4: loaded in DCM, on a 50 g SNAP Si-cartridge, eluting with 0-5% methanol in DCM (15 CV). The appropriate fractions were combined and the solvent was evaporated in vacuo to give the BOC-protected product. The BOC-protected product was taken up in dichloromethane (DCM) (5 ml) and treated with TFA (0.663 ml, 8.61 mmol). The reaction mixture was stirred at rt for 30 min and left without stirring for 15 h. The reaction mixture was then concentrated under reduced pressure and the residue was loaded in methanol onto a 10 g SCX column (preconditioned with MeOH). The column was washed with MeOH (3 CV) and eluted with methanolic ammonia (2N) (4 CV). The methanolic ammonia fractions were combined and the solvent was evaporated in vacuo to give the title compound (178 mg) as a yellow oil.
LCMS (Method B): Rt=0.63 min, MH+=403.2

Example 2B: (R)-(3-Aminopiperidin-1-yl)(2-(1-ethyl-1H-pyrrolo[2,3-b]pyridin-2-yl)-1-methyl-1H-benzo[d]imidazol-5-yl)methanone hydrochloride

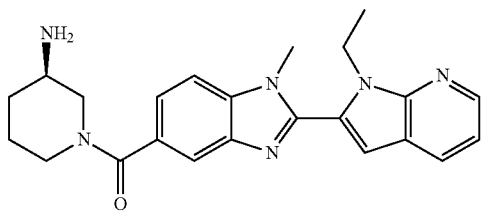 [SMILES: CCn1c(-c2nc3cc(C(=O)N4CCC[C@@H](N)C4)ccc3n2C)cc2cccnc21]

(R)-(3-aminopiperidin-1-yl)(2-(1-ethyl-1H-pyrrolo[2,3-b]pyridin-2-yl)-1-methyl-1H-benzo[d]imidazol-5-yl)methanone (170 mg) was taken up in MeOH (5 mL) and treated with HCl (1M in ether) (165 µL) and blown down under nitrogen to give (R)-(3-aminopiperidin-1-yl)(2-(1-ethyl-1H-pyrrolo[2,3-b]pyridin-2-yl)-1-methyl-1H-benzo[d]imidazol-5-yl)methanone, hydrochloride (187 mg, 0.43 mmol, 74.2% yield) as a cream solid.
LCMS (Method B): Rt=0.63 min, MH+=403.1

Example 3: (R)-(3-Aminopiperidin-1-yl)(2-(1-ethyl-1H-pyrrolo[2,3-c]pyridin-2-yl)-1-methyl-1H-benzo[d]imidazol-5-yl)methanone

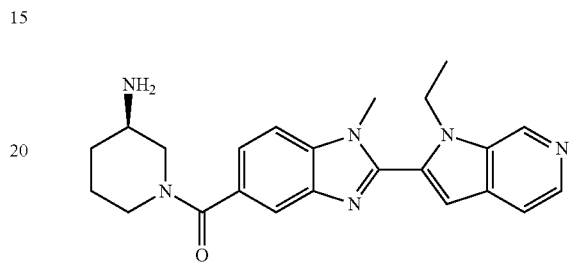

To a solution of (R)-tert-butyl (1-(2-(1-ethyl-1H-pyrrolo[2,3-c]pyridin-2-yl)-1-methyl-1H-benzo[d]imidazole-5-carbonyl)piperidin-3-yl)carbamate (42 mg, 0.084 mmol) in dichloromethane (DCM) (1 mL) was added TFA (0.258 mL, 3.34 mmol) and the reaction stirred at room temperature for 2 h. The reaction mixture was concentrated in vacuo to afford a yellow oil. This was dissolved in methanol and loaded onto an SCX cartridge (5 g). It was eluted with methanol (3 column volumes) and product eluted as free base with 2M ammonia in methanol. The filtrate from the ammonia fractions was concentrated in vacuo to yield the title compound as a yellow solid (34 mg).
LCMS (Method A): Rt=0.73 min, MH+=403.2

Example 4A: (R)-(3-Aminopiperidin-1-yl)(1-methyl-2-(1-(2,2,2-trifluoroethyl)-1H-pyrrolo[2,3-b]pyridin-2-yl)-1H-benzo[d]imidazol-5-yl)methanone

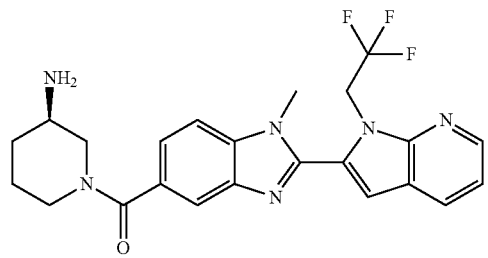 [SMILES: Cn1c(-c2cc3cccnc3n2CC(F)(F)F)nc2cc(C(=O)N3CCC[C@@H](N)C3)ccc21]

To a stirred solution of (R)-tert-butyl (1-(1-methyl-2-(1-(2,2,2-trifluoroethyl)-1H-pyrrolo[2,3-b]pyridin-2-yl)-1H-benzo[d]imidazole-5-carbonyl)piperidin-3-yl)carbamate (1.9336 g, 3.47 mmol) in dichloromethane (DCM) (5.5 ml) was added TFA (5.05 ml, 66.0 mmol) dropwise. The reaction mixture was stirred for 45 min. The mixture was concentrated in vacuo, dissolved in methanol and purified by SPE on a pre-conditioned sulfonic acid (SCX) 70 g cartridge. The column was washed with methanol (5 CV) and the product was eluted with a 2M Ammonia in methanol solution (4 CV). The appropriate fractions were combined and the solvent was evaporated in vacuo to give a crude product that was purified by preparative HPLC (MDAP Method E). Appropriate fractions were combined and concentrated in vacuo to yield the title compound (1.35 g)
LCMS (Method B): Rt=0.71 min, MH+=457.2

Example 4B: (R)-(3-Aminopiperidin-1-yl)(1-methyl-2-(1-(2,2,2-trifluoroethyl)-1H-pyrrolo[2,3-b]pyridin-2-yl)-1H-benzo[d]imidazol-5-yl)methanone hydrochloride

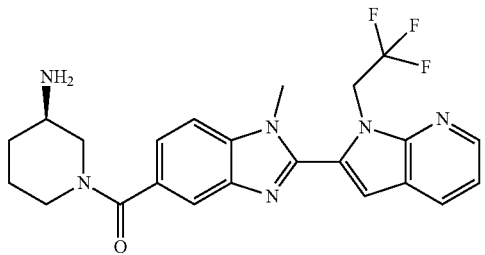 [SMILES: Cn1c(-c2cc3cccnc3n2CC(F)(F)F)nc2cc(C(=O)N3CCC[C@@H](N)C3)ccc21]

HCl in Et$_2$O (1 M) (0.15 mL, 0.15 mmol) was added dropwise to a solution of (R)-(3-aminopiperidin-1-yl)(1-methyl-2-(1-(2,2,2-trifluoroethyl)-1H-pyrrolo[2,3-b]pyridin-2-yl)-1H-benzo[d]imidazol-5-yl)methanone (60 mg, 0.13 mmol) in methanol (1 mL) and diethyl ether (1 mL). After stirring for 2.5 h at rt, the reaction mixture was dried under a stream of nitrogen to give the required product (R)-(3-aminopiperidin-1-yl)(1-methyl-2-(1-(2,2,2-trifluoroethyl)-1H-pyrrolo[2,3-b]pyridin-2-yl)-1H-benzo[d]imidazol-5-yl)methanone hydrochloride (64 mg, 0.13 mmol, 99% yield).
LCMS (Method B): Rt=0.85 min, MH+=457.2

Example 5A: (R)-(3-Aminopiperidin-1-yl)(2-(1-(cyclopropylmethyl)-1H-pyrrolo[2,3-b]pyridin-2-yl)-1-methyl-1H-benzo[d]imidazol-5-yl)methanone

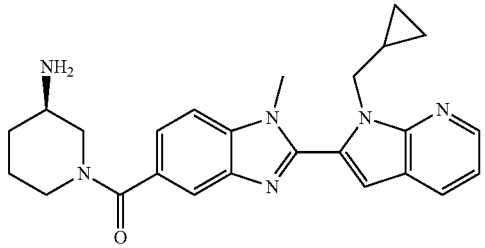 [SMILES: Cn1c(-c2cc3cccnc3n2CC2CC2)nc2cc(C(=O)N3CCC[C@@H](N)C3)ccc21]

To a solution of (R)-tert-butyl (1-(2-(1-(cyclopropylmethyl)-1H-pyrrolo[2,3-b]pyridin-2-yl)-1-methyl-1H-benzo[d]imidazole-5-carbonyl)piperidin-3-yl)carbamate (3.402 g, 6.44 mmol) in dichloromethane (DCM) (40 ml) was added TFA (9 ml, 118 mmol) dropwise. The reaction mixture was stirred for 3 hours. The reaction mixture was concentrated under vacuum to afford a yellow oil. The oil was dissolved in methanol and loaded onto a 70 g SCX cartridge. The column was washed with MeOH (2 CV) and the product collected as the free base with 2M ammonia in methanol (3 CV). The product was concentrated in vacuo and dried under vacuum to afford a yellow solid. This was dissolved in hot ethanol and concentrated in vacuo. It was again dissolved in hot ethanol, concentrated in vacuo and dried under vacuum to yield the title compound as a yellow solid (2.61 g).

LCMS (Method A): Rt=0.89 min, MH+=429.3
$^1$H NMR (400 MHz, DMSO-d$_6$) δ ppm: 8.24 (1H, d), 7.96 (1H, d), 7.51-7.62 (2H, m), 7.21 (1H, d), 7.05 (1H, dd), 6.96 (1H, s), 4.41 (2H, d), 3.82 (3H, s), 3.28-4.26 (2H, m), 2.40-2.66 (1H, m), 2.37-2.64 (2H, m), 1.62-1.77 (1H, m), 1.15-1.60 (4H, m), 0.92-1.15 (2H, m), 0.07-0.16 (2H, m), 0.03-0.04 (2H, m)

Example 5B: (R)-(3-Aminopiperidin-1-yl)(2-(1-(cyclopropylmethyl)-1H-pyrrolo[2,3-b]pyridin-2-yl)-1-methyl-1H-benzo[d]imidazol-5-yl)methanone, hydrochloride To a solution of (R)-(3-aminopiperidin-1-yl)(2-(1-(cyclopropylmethyl)-1H-pyrrolo[2,3-b]pyridin-2-yl)-1-methyl-1H-benzo[d]imidazol-5-yl)methanone (2.61 g, 6.09 mmol) in dichloromethane (DCM) (1.5 mL) was added HCl (2M in diethyl ether) (3 ml, 6.00 mmol). The mixture was sonicated for 2 minutes and then concentrated under vacuum to afford a yellow solid. This was dissolved in a minimum volume of hot ethanol. The solvent was removed under nitrogen and the product dried in a vacuum pistol at 50° C. overnight and then at 60° C. over the weekend to give the title compound as a yellow solid (2.7 g).
LCMS (Method A): Rt=0.88 min, MH+=429.3

Example 6: (R)-(3-Aminopiperidin-1-yl)(2-(1-ethyl-5-methoxy-1H-pyrrolo[2,3-b]pyridin-2-yl)-1-methyl-1H-benzo[d]imidazol-5-yl)methanone

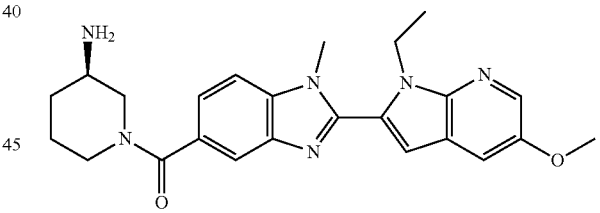

To a stirred solution of (R)-tert-butyl (1-(2-(1-ethyl-5-methoxy-1H-pyrrolo[2,3-b]pyridin-2-yl)-1-methyl-1H-benzo[d]imidazole-5-carbonyl)piperidin-3-yl)carbamate (24 mg, 0.045 mmol) in DCM (2 mL) was added TFA (2 mL, 26.0 mmol) dropwise with continuous stirring. The reaction was stirred at room temperature under nitrogen for 1 h. The reaction mixture was concentrated in vacuo before being dissolved in MeOH and purified by SPE on sulfonic acid (SCX) 1 g, first washing with MeOH and then eluting using a 10% NH$_3$/MeOH solution to give the free base of the product. The appropriate fractions were combined and evaporated in vacuo before being azeotroped with cyclohexane to give the title compound as a pale yellow solid (13 mg).

LCMS (Method A): Rt=0.84 min, MH+=433.3

Example 7: (R)-(3-Aminopiperidin-1-yl)(2-(1-ethyl-5-methoxy-1H-pyrrolo[2,3-c]pyridin-2-yl)-1-methyl-1H-benzo[d]imidazol-5-yl)methanone

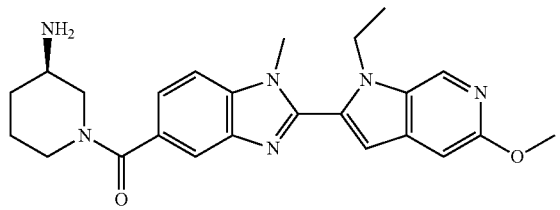 [SMILES: CCn1c(-c2nc3cc(C(=O)N4CCC[C@@H](N)C4)ccc3n2C)cc2cc(OC)ncc21]

To a stirred solution of (R)-tert-butyl (1-(2-(1-ethyl-5-methoxy-1H-pyrrolo[2,3-c]pyridin-2-yl)-1-methyl-1H-benzo[d]imidazole-5-carbonyl)piperidin-3-yl)carbamate (106 mg, 0.199 mmol) in dichloromethane (DCM) (3 mL) was added TFA (3 mL, 38.9 mmol) dropwise with continuous stirring. The reaction was stirred at room temperature under nitrogen for 1 hr. LCMS showed the reaction was complete with no starting material remaining. The reaction mixture was concentrated in vacuo before being dissolved in MeOH and purified by SPE on sulfonic acid (SCX) 5 g, first washing with MeOH and then eluting using a 10% $NH_3$/MeOH solution to give the free base of the product. The appropriate fractions were combined and evaporated in vacuo before being azeotroped with cHex and dried on the high vacuum line to give the required product (69 mg) as a white solid.

LCMS (Method A): Rt=0.80 min, MH+=433.2

Example 8: 2-(5-{[(3R)-3-Amino-1-piperidinyl]carbonyl}-1-methyl-1H-benzimidazol-2-yl)-1-ethyl-1H-pyrrolo[2,3-b]pyridin-5-ol

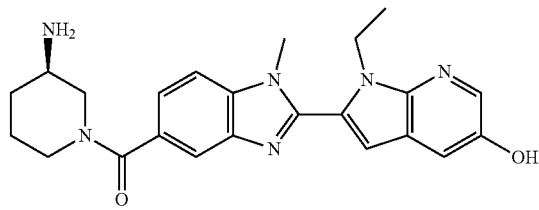 [SMILES: CCn1c(-c2nc3cc(C(=O)N4CCC[C@@H](N)C4)ccc3n2C)cc2cc(O)cnc21]

A solution of (R)-(3-aminopiperidin-1-yl)(2-(1-ethyl-5-methoxy-1H-pyrrolo[2,3-b]pyridin-2-yl)-1-methyl-1H-benzo[d]imidazol-5-yl)methanone (11 mg, 0.025 mmol) in dichloromethane (DCM) (3 mL) was cooled to ~0° C. using an ice-water bath under nitrogen. Boron tribromide (8 µL, 0.085 mmol) was added to the reaction dropwise with vigorous stirring. The reaction mixture was allowed to return to room temperature with stirring, over 4 hours. The reaction mixture was partitioned with water (5 mL), the organic layer was isolated using a hydrophobic frit, and the aqueous layer was re-extracted with DCM (2×10 mL). The combined organic layers were evaporated in vacuo but LCMS showed there was no product. The aqueous layer was neutralised by the dropwise addition of $NaHCO_3$, partitioned with DCM and separated. The aqueous was re-extracted with DCM (2×15 mL) and the combined organic layers were concentrated in vacuo to give the crude product. The residue was dissolved in DMSO 1 mL and purified by MDAP with an ammonium bicarbonate modifier (Method E). The appropriate fraction was evaporated in vacuo to give the title compound as a yellow gum (12 mg).

LCMS (Method A): Rt=0.67 min, MH+=419.25

Example 9A: (R)-(3-Aminopiperidin-1-yl)(2-(1-ethyl-1H-pyrrolo[2,3-b]pyridin-2-yl)-7-methoxy-1-methyl-1H-benzo[d]imidazol-5-yl)methanone

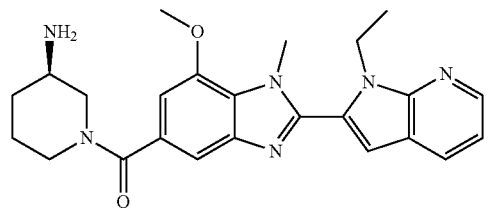 [SMILES: CCn1c(-c2nc3cc(C(=O)N4CCC[C@@H](N)C4)cc(OC)c3n2C)cc2cccnc21]

To a solution of (R)-tert-butyl (1-(2-(1-ethyl-1H-pyrrolo[2,3-b]pyridin-2-yl)-7-methoxy-1-methyl-1H-benzo[d]imidazole-5-carbonyl)piperidin-3-yl)carbamate (4.4 g, 8.26 mmol) in dichloromethane (DCM) (20 ml) was added TFA (9 ml, 118 mmol) dropwise. The reaction mixture was stirred for 1 hour 30 minutes. LC/MS showed that that desired product had formed with no starting material remaining. The reaction mixture was concentrated under vacuum to afford an oil. The oil was dissolved in methanol and split into two equal batches and passed through two separate 70 g SCX cartridges. The columns were washed with MeOH (2 CV) and the product collected from both columns as the free base with 2M ammonia in methanol (3 CV). The product was concentrated under vacuo and dried under vacuum to afford the title compound as a white solid (3.46 g).

LCMS (Method A): Rt=0.89 min, MH+=433.4

$^1$H NMR (400 MHz, DMSO-de) 6 ppm: 8.42 (dd, 1H), 8.12 (dd, 1H), 7.32 (s, 1H), 7.22 (dd, 1H), 7.06 (s, 1H), 6.87 (s, 1H), 4.62 (q, 2H), 4.14 (s, 3H), 3.99 (s, 3H), 3.50-4.43 (m, 2H), 2.63-2.71 (m, 1H), 2.58-3.11 (m, 2H), 1.82-1.91 (m, 1H), 1.61-1.76 (m, 1H), 1.52-1.59 (m, 2H), 1.39-1.50 (m, 1H), 1.25 (t, 3H), 1.20-1.26 (m, 1H)

Example 9B: (R)-(3-Aminopiperidin-1-yl)(2-(1-ethyl-1H-pyrrolo[2,3-b]pyridin-2-yl)-7-methoxy-1-methyl-1H-benzo[d]imidazol-5-yl)methanone, hydrochloride (R)-(3-aminopiperidin-1-yl)(2-(1-ethyl-1H-pyrrolo[2,3-b]pyridin-2-yl)-7-methoxy-1-methyl-1H-benzo[d]imidazol-5-yl)methanone (2.365 g) was dissolved in DCM (6 ml) and HCl (2M in diethyl ether) (2.735 ml, 5.47 mmol) was added to the solution. The solvent was then removed under nitrogen and concentrated under vacuum to afford the title compound as a white solid (2.43 g).

LCMS (Method A): Rt=0.89 min, MH+=433.3

Example 10A: (R)-(3-Aminopiperidin-1-yl)(2-(1-(cyclopropylmethyl)-1H-pyrrolo[2,3-b]pyridin-2-yl)-7-methoxy-1-methyl-1H-benzo[d]imidazol-5-yl)methanone

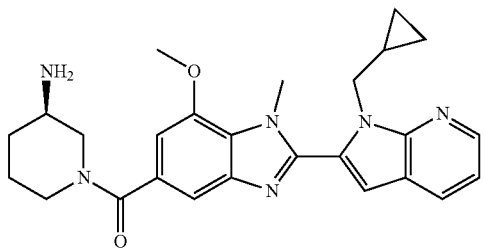 [SMILES: COc1cc(C(=O)N2CCC[C@@H](N)C2)cc2nc(-c3cc4cccnc4n3CC3CC3)n(C)c12]

To a solution of (R)-tert-butyl (1-(2-(1-(cyclopropylmethyl)-1H-pyrrolo[2,3-b]pyridin-2-yl)-7-methoxy-1-methyl-1H-benzo[d]imidazole-5-carbonyl)piperidin-3-yl)carbamate (1.5587 g, 2.79 mmol) in DCM (10 ml) was added TFA (5 mL, 65.3 mmol) dropwise. The reaction mixture was stirred for 30 minutes and then concentrated under vacuum to afford an oil. The oil was dissolved in methanol and loaded onto a 70 g SCX cartridge. The column was washed with MeOH (2 CV) and the product collected as the free base with 2M ammonia in methanol (3 CV). The product was concentrated in vacuo yield a crude product. This was purified by high pH MDAP (Method E). Appropriate fractions were combined and concentrated in vacuo to yield the title compound as a white solid, 1.127 g.

LCMS (Method A): Rt=0.96 min, MH+=459.3

$^1$H NMR (400 MHz, DMSO-d$_6$) δ ppm: 8.27 (1H, dd), 7.99 (1H, dd), 7.22 (1H, s), 7.08 (1H, dd), 6.94 (1H, s), 6.76 (1H, s), 4.36 (2H, d), 4.00 (3H, s), 3.86 (3H, s), 3.45-4.27 (4H, m), 2.80-2.97 (1H, m), 2.64-2.80 (2H, m), 1.71-1.87 (1H, m), 1.50-1.66 (1H, m), 1.28-1.44 (1H, m), 1.14-1.29 (1H, m), 0.84-1.07 (1H, m), 0.08-0.22 (2H, m), −0.08-0.05 (2H, m)

Example 10B: (R)-(3-Aminopiperidin-1-yl)(2-(1-(cyclopropylmethyl)-1H-pyrrolo[2,3-b]pyridin-2-yl)-7-methoxy-1-methyl-1H-benzo[d]imidazol-5-yl)methanone, hydrochloride (R)-(3-Aminopiperidin-1-yl)(2-(1-(cyclopropylmethyl)-1H-pyrrolo[2,3-b]pyridin-2-yl)-7-methoxy-1-methyl-1H-benzo[d]imidazol-5-yl)methanone (2.2 g) was dissolved in a minimum volume of DCM and HCl (2M in diethyl ether) (2.4 ml, 4.80 mmol) added to the solution. The resulting suspension was sonicated for 2 minutes and the solution concentrated under vacuum to afford the title compound as a white solid (2.57 g)

LCMS (Method A): Rt=0.95 min, MH+=459.3

Example 11A: (R)-(3-Aminopiperidin-1-yl)(7-methoxy-1-methyl-2-(1-(2,2,2-trifluoroethyl)-1H-pyrrolo[2,3-b]pyridin-2-yl)-1H-benzo[d]imidazol-5-yl)methanone

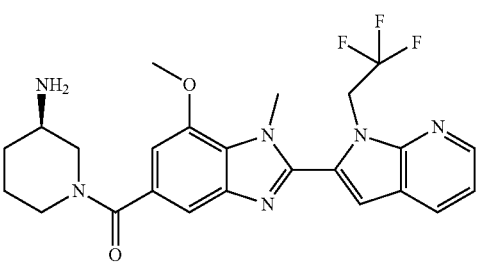 [SMILES: COc1cc(C(=O)N2CCC[C@@H](N)C2)cc2nc(-c3cc4cccnc4n3CC(F)(F)F)n(C)c12]

To a solution of (R)-tert-butyl (1-(7-methoxy-1-methyl-2-(1-(2,2,2-trifluoroethyl)-1H-pyrrolo[2,3-b]pyridin-2-yl)-1H-benzo[d]imidazole-5-carbonyl)piperidin-3-yl)carbamate (4.31 g, 7.35 mmol) in dichloromethane (DCM) (20 ml) at 0° C. was added TFA (9 ml, 118 mmol) dropwise. The reaction mixture was stirred for 5 minutes and allowed to warm to room temperature and stirred for 3 hours. The reaction mixture was concentrated under vacuum to afford an oil. The oil was dissolved in methanol and split into two equal batches. These were passed through two separate 70 g SCX cartridges. The columns were washed with MeOH (2 CV) and the product collected from both columns as the free base with 2M ammonia in methanol (3 CV). The product was concentrated and dried under vacuum to afford the title compound as a white solid (2.53 g).

LCMS (Method A): Rt=0.97 min, MH+=487.1

$^1$H NMR (400 MHz, DMSO-d$_6$) δ ppm: 8.48 (dd, 1H), 8.21 (dd, 1H), 7.33 (s, 1H), 7.32-7.33 (m, 1H), 7.31 (s, 1H), 6.88 (s, 1H), 5.74 (q, 2H), 4.19 (s, 3H), 4.00 (s, 3H), 3.51-4.39 (m, 2H), 2.64-2.73 (m, 1H), 2.62-3.01 (m, 2H), 1.83-1.90 (m, 1H), 1.62-1.77 (m, 1H), 1.49-1.59 (m, 2H), 1.39-1.50 (m, 1H), 1.17-1.30 (m, 1H)

Example 11B: (R)-(3-Aminopiperidin-1-yl)(7-methoxy-1-methyl-2-(1-(2,2,2-trifluoroethyl)-1H-pyrrolo[2,3-b]pyridin-2-yl)-1H-benzo[d]imidazol-5-yl)methanone, hydrochloride (R)-(3-Aminopiperidin-1-yl)(7-methoxy-1-methyl-2-(1-(2,2,2-trifluoroethyl)-1H-pyrrolo[2,3-b]pyridin-2-yl)-1H-benzo[d]imidazol-5-yl)methanone (1.5073 g) was dissolved in DCM (5 ml) and HCl (2M in diethyl ether) (1.5 ml, 3.00 mmol) was added to the solution. The solvent was then removed under nitrogen and concentrated under vacuum to afford the title compound as a white solid (1.61 g)

LCMS (Method A): Rt=0.96 min, MH+=487.2

Example 12: (3-Aminopiperidin-1-yl)(2-(1-ethyl-1H-pyrrolo[2,3-b]pyridin-2-yl)-1-methyl-1H-benzo[d]imidazol-5-yl)methanone

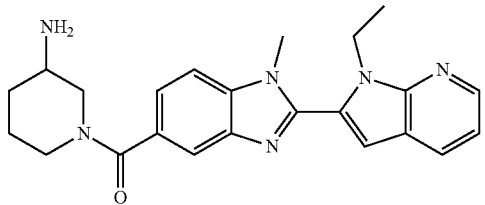 [SMILES: CCn1c(-c2nc3cc(C(=O)N4CCCC(N)C4)ccc3n2C)cc2cccnc21]

To a solution of tert-butyl (1-(2-(1-ethyl-1H-pyrrolo[2,3-b]pyridin-2-yl)-1-methyl-1H-benzo[d]imidazole-5-carbonyl)piperidin-3-yl)carbamate (104 mg, 0.207 mmol) in dichloromethane (DCM) (1 mL) was added TFA (0.367 mL, 4.76 mmol) and the reaction stirred at room temperature for 2 h. LCMS (A1) showed no desired product but reaction had progressed to 1 major product. The reaction mixture was concentrated in vacuo to afford a colourless oil. This was dissolved in methanol and loaded onto an SCX cartridge (5 g). It was eluted with methanol (3 column volumes) and product eluted as free base with 2M ammonia in methanol. The filtrate from the ammonia fractions was concentrated in vacuo to yield a yellow solid—(3-aminopiperidin-1-yl)(2-(1-ethyl-1H-pyrrolo[2,3-b]pyridin-2-yl)-1-methyl-1H-benzo[d]imidazol-5-yl)methanone (81 mg, 0.201 mmol, 97% yield).
LCMS (Method B): Rt=0.64 min, MH+=403.2

Example 13: ((3S,4R)-3-Amino-4-hydroxypiperidin-1-yl)(2-(1-(cyclopropylmethyl)-1H-pyrrolo[2,3-b]pyridin-2-yl)-1-methyl-1H-benzo[d]imidazol-5-yl)methanone, hydrochloride

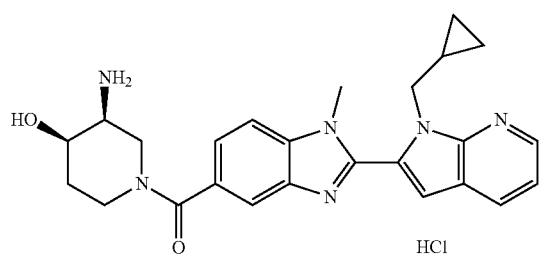 [SMILES: Cn1c(-c2cc3cccnc3n2CC2CC2)nc2cc(C(=O)N3CC[C@@H](O)[C@@H](N)C3)ccc21 ; Cl]

To a flask containing tert-butyl ((3S,4R)-1-(2-(1-(cyclopropylmethyl)-1H-pyrrolo[2,3-b]pyridin-2-yl)-1-methyl-1H-benzo[d]imidazole-5-carbonyl)-4-hydroxypiperidin-3-yl)carbamate (37 mg, 0.068 mmol) in dichloromethane (DCM) (1 mL) was added TFA (0.199 mL, 2.58 mmol) and the reaction was stirred for 1 h. The reaction mixture was concentrated in vacuo to afford a brown oil. This was dissolved in methanol and loaded onto an SCX cartridge (5 g). It was eluted with methanol (3 column volumes) and product eluted as free base with 2M ammonia in methanol. The filtrate from the ammonia fractions was concentrated in vacuo to yield a yellow oil—((3S,4R)-3-amino-4-hydroxypiperidin-1-yl)(2-(1-(cyclopropylmethyl)-1H-pyrrolo[2,3-b]pyridin-2-yl)-1-methyl-1H-benzo[d]imidazol-5-yl)methanone (32 mg, 0.068 mmol, 100% yield). This was dissolved in dichloromethane (DCM) (1 mL) in a vial and HCl (2 M in Et$_2$O) (0.034 mL, 0.068 mmol) was added. The resultant suspension was sonicated for 5 min and allowed to stand for 15 min. The solvent was then removed under a positive pressure of nitrogen and the product dried in vacuo to afford ((3S,4R)-3-amino-4-hydroxypiperidin-1-yl)(2-(1-(cyclopropylmethyl)-1H-pyrrolo[2,3-b]pyridin-2-yl)-1-methyl-1H-benzo[d]imidazol-5-yl)methanone, hydrochloride (32 mg, 0.067 mmol, 98% yield) as a white solid.
LCMS (Method A): Rt=0.83 mins, MH+=445.3

Example 14: ((3S,4R)-3-Amino-4-hydroxypiperidin-1-yl)(2-(1-(cyclopropylmethyl)-1H-pyrrolo[2,3-b]pyridin-2-yl)-7-methoxy-1-methyl-1H-benzo[d]imidazol-5-yl)methanone, hydrochloride

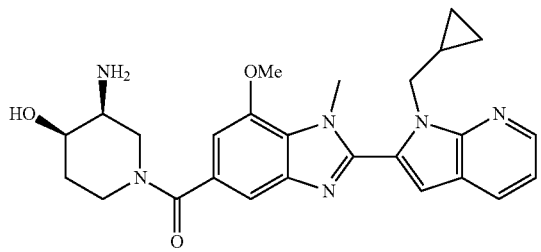 [SMILES: COc1cc(C(=O)N2CC[C@@H](O)[C@@H](N)C2)cc2nc(-c3cc4cccnc4n3CC3CC3)n(C)c12]

To a flask containing tert-butyl ((3S,4R)-1-(2-(1-(cyclopropylmethyl)-1H-pyrrolo[2,3-b]pyridin-2-yl)-7-methoxy-1-methyl-1H-benzo[d]imidazole-5-carbonyl)-4-hydroxypiperidin-3-yl)carbamate (143 mg, 0.249 mmol) in dichloromethane (DCM) (1.5 mL) was added TFA (0.307 mL, 3.98 mmol) and the reaction was stirred for 1 h. LCMS showed complete reaction. The reaction mixture was concentrated in vacuo to afford a brown oil. This was dissolved in methanol and loaded onto an SCX cartridge (5 g). It was eluted with methanol (3 column volumes) and product eluted as free base with 2M ammonia in methanol. The filtrate from the ammonia fractions was concentrated in vacuo to yield a yellow oil—97% purity by LCMS. The crude product (104 mg) was taken up in DMSO/MeOH (1:1, 1.8 mL) and further purified by MDAP (Method E, 2 injections). The appropriate fractions were combined and concentrated in vacuo to afford the desired product as a colourless oil—((3S,4R)-3-amino-4-hydroxypiperidin-1-yl)(2-(1-(cyclopropylmethyl)-1H-pyrrolo[2,3-b]pyridin-2-yl)-7-methoxy-1-methyl-1H-benzo[d]imidazol-5-yl)methanone (71 mg, 0.150 mmol, 60.1% yield). The free base (71 mg) was dissolved in dichloromethane (DCM) (1 mL) in a vial and HCl (2M in Et$_2$O) (0.075 mL, 0.15 mmol) was added. The resultant suspension was sonicated for 5 min and allowed to stand for 15 min. The solvent was then removed under a positive pressure of nitrogen and the product dried in vacuo to afford ((3S,4R)-3-amino-4-hydroxypiperidin-1-yl)(2-(1-(cyclopropylmethyl)-1H-pyrrolo[2,3-b]pyridin-2-yl)-7-methoxy-1-methyl-1H-benzo[d]imidazol-5-yl)methanone, hydrochloride (78 mg, 0.153 mmol, 61.3% yield) as an off white solid.
LCMS (Method A): Rt=0.74 min, MH+=475.3
1H NMR (600 MHz, DMSO-d6) δ ppm 8.41 (dd, J=4.6, 1.7 Hz, 1H), 8.13 (dd, J=7.9, 1.7 Hz, 1H), 7.94-8.11 (m, 3H), 7.44 (s, 1H), 7.22 (dd, J=7.9, 4.6 Hz, 1H), 7.08 (s, 1H) 6.96 (s, 1H), 5.71 (br. s., 1H), 4.50 (d, J=6.9 Hz, 2H), 4.14 (s, 3H), 4.05-4.10 (m, 1H), 4.00 (s, 3H), 3.79-3.99 (m, 1H), 3.40-3.62 (m, 3H), 3.28-3.35 (m, 1H), 1.68-1.86 (m, 2H) 1.07-1.18 (m, 1H), 0.24-0.35 (m, 2H), 0.08-0.18 (m, 2H).

Example 15: (R)-(3-Aminopiperidin-1-yl)(2-(1-ethyl-1H-pyrrolo[2,3-b]pyridin-2-yl)-1-methyl-7-(trifluoromethoxy)-1H-benzo[d]imidazol-5-yl)methanone

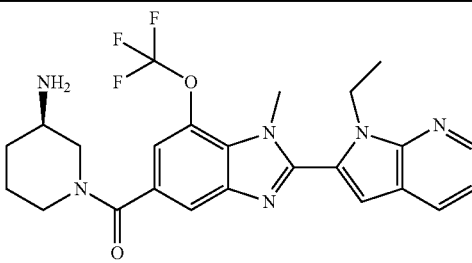

Prepared in a similar manner to Example 1 from (R)-tert-butyl (1-(2-(1-ethyl-1H-pyrrolo[2,3-b]pyridin-2-yl)-1-methyl-7-(trifluoromethoxy)-1H-benzo[d]imidazole-5-carbonyl)piperidin-3-yl)carbamate. LCMS (Method A): Rt = 1.01 mins, MH⁺ = 487.2

Example 16: (R)-(3-Aminopiperidin-1-yl)(7-methoxy-1-methyl-2-(1-neopentyl-1H-pyrrolo[2,3-b]pyridin-2-yl)-1H-benzo[d]imidazol-5-yl)methanone

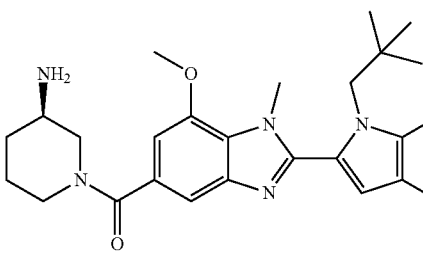

Prepared in a similar manner to Example 1 from (R)-tert-butyl (1-(7-methoxy-1-methyl-2-(1-neopentyl-1H-pyrrolo[2,3-b]pyridin-2-yl)-1H-benzo[d]imidazole-5-carbonyl)piperidin-3-yl)carbamate. LCMS (Method A): Rt = 1.06 mins, MH⁺ = 475.3

Example 17: ((R)-3-Aminopiperidin-1-yl)(7-methoxy-1-methyl-2-(1-(2-methylbutyl)-1H-pyrrolo[2,3-b]pyridin-2-yl)-1H-benzo[d]imidazol-5-yl)methanone

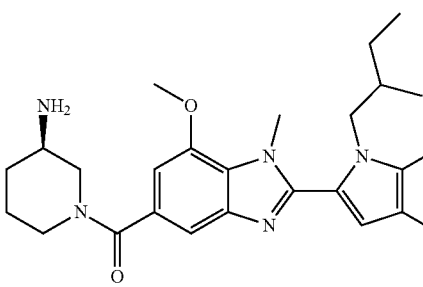

Prepared in a similar manner to Example 1 from tert-butyl ((3R)-1-(7-methoxy-1-methyl-2-(1-(2-methylbutyl)-1H-pyrrolo[2,3-b]pyridin-2-yl)-1H-benzo[d]imidazole-5-carbonyl)piperidin-3-yl)carbamate. LCMS (Method A): Rt = 1.04 mins, MH⁺ = 475.3

Example 18 (R)-(3-Aminopiperidin-1-yl)(2-(1-ethyl-1H-pyrrolo[2,3-b]pyridin-2-yl)-7-methoxy-1-(2-methoxyethyl)-1H-benzo[d]imidazol-5-yl)methanone, hydrochloride

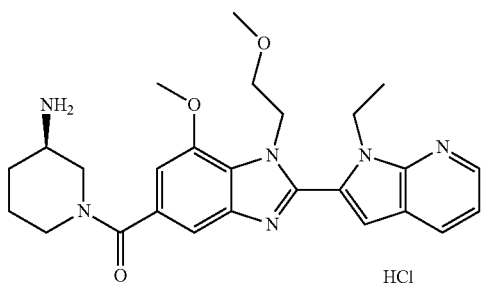 [SMILES: CCn1c(-c2nc3cc(C(=O)N4CCC[C@@H](N)C4)cc(OC)c3n2CCOC)cc2cccnc21 ; Cl]

To a solution of (R)-tert-butyl (1-(2-(1-ethyl-1H-pyrrolo[2,3-b]pyridin-2-yl)-7-methoxy-1-(2-methoxyethyl)-1H-benzo[d]imidazole-5-carbonyl)piperidin-3-yl)carbamate (110 mg, 0.191 mmol) in dichloromethane (DCM) (2 mL) was added TFA (0.35 mL, 4.57 mmol). The reaction mixture was stirred for 40 minutes. LCMS showed that the desired product had formed with 98% purity. The reaction mixture was concentrated under vacuum to afford a yellow oil. The oil was dissolved in methanol and loaded onto a SCX cartridge (10 g). The column was washed with MeOH (3 CV) and the product collected as the free base with 2M ammonia in methanol (8 CV). The product was concentrated in vacuo to afford a colourless oil. The product was dissolved in of 1:1 DMSO/MeOH (1.8 mL) and two 0.9 mL samples were purified by MDAP (Method E). Product fractions were collected and concentrated under vacuum to afford (R)-(3-aminopiperidin-1-yl)(2-(1-ethyl-1H-pyrrolo[2,3-b]pyridin-2-yl)-7-methoxy-1-(2-methoxyethyl)-1H-benzo[d]imidazol-5-yl)methanone as a colourless oil. The colourless oil was dissolved in dichloromethane (DCM) (2 mL) and transferred to a vial and HCl (2M in diethyl ether) (0.06 mL, 0.120 mmol) was added to the solution. The solvent was removed under nitrogen and then the sample dried in a vacuum pistol overnight to afford (R)-(3-aminopiperidin-1-yl)(2-(1-ethyl-1H-pyrrolo[2,3-b]pyridin-2-yl)-7-methoxy-1-(2-methoxyethyl)-1H-benzo[d]imidazol-5-yl)methanone, hydrochloride (75.8 mg, 0.148 mmol, 77% yield)—as a white solid.

LCMS (Method A): Rt=0.88 mins, MH⁺=477.4

| Example | Structure | Notes |
|---|---|---|
| Example 19: (S)-(3-Aminopiperidin-1-yl)(2-(1-ethyl-1H-pyrrolo[2,3-b]pyridin-2-yl)-7-methoxy-1-methyl-1H-benzo[d]imidazol-5-yl)methanone, hydrochloride | 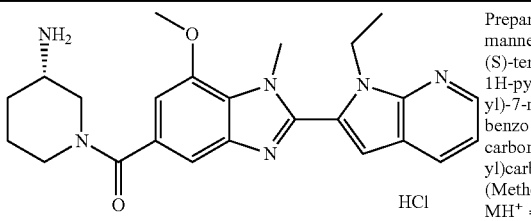 | Prepared in a similar manner to Example 13 from (S)-tert-butyl (1-(2-(1-ethyl-1H-pyrrolo[2,3-b]pyridin-2-yl)-7-methoxy-1-methyl-1H-benzo[d]imidazole-5-carbonyl)piperidin-3-yl)carbamate. LCMS (Method A): Rt = 0.90 mins, MH+ = 433.3 |
| Example 20: (R)-(3-Aminopiperidin-1-yl)(2-(1-ethyl-1H-pyrrolo[2,3-b]pyridin-2-yl)-1-isobutyl-7-methoxy-1H-benzo[d]imidazol-5-yl)methanone, hydrochloride | 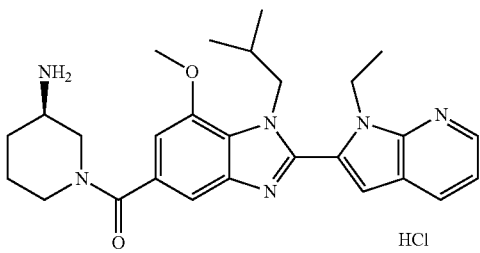 | Prepared in a similar manner to Example 13 from (R)-tert-butyl (1-(2-(1-ethyl-1H-pyrrolo[2,3-b]pyridin-2-yl)-1-isobutyl-7-methoxy-1H-benzo[d]imidazole-5-carbonyl)piperidin-3-yl)carbamate. LCMS (Method A): Rt = 0.90 mins, MH+ = 433.3 |
| Example 21: (R)-(3-Aminopiperidin-1-yl)(7-methoxy-2-(1-(2-methoxy-2-methylpropyl)-1H-pyrrolo[2,3-b]pyridin-2-yl)-1-methyl-1H-benzo[d]imidazol-5-yl)methanone | 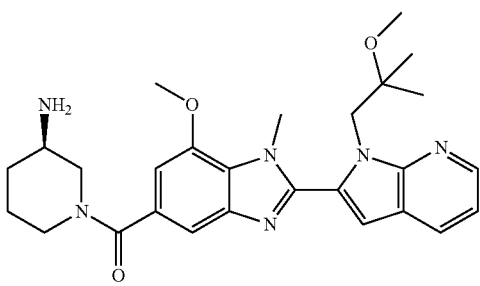 [SMILES: COc1cc(C(=O)N2CCC[C@@H](N)C2)cc2nc(-c3cc4cccnc4n3CC(C)(C)OC)n(C)c12] | Prepared in a similar manner to Example 1 from (R)-tert-Butyl (1-(7-methoxy-2-(1-(2-methoxy-2-methylpropyl)-1H-pyrrolo[2,3-b]pyridin-2-yl)-1-methyl-1H-benzo[d]imidazole-5-carbonyl)piperidin-3-yl)carbamate. LCMS (Method B): Rt = 0.74 mins, MH+ = 491.3 |
| Example 22: (R)-(3-Aminopiperidin-1-yl)(2-(1-isobutyl-1H-pyrrolo[2,3-b]pyridin-2-yl)-7-methoxy-1-methyl-1H-benzo[d]imidazol-5-yl)methanone, hydrochloride | 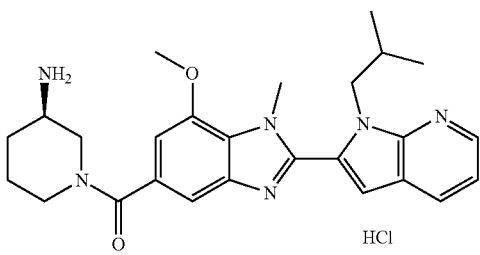 [SMILES: COc1cc(C(=O)N2CCC[C@@H](N)C2)cc2nc(-c3cc4cccnc4n3CC(C)C)n(C)c12 ; Cl] | Prepared in a similar manner to Example 18 from (R)-tert-Butyl (1-(2-(1-isobutyl-1H-pyrrolo[2,3-b]pyridin-2-yl)-7-methoxy-1-methyl-1H-benzo[d]imidazole-5-carbonyl)piperidin-3-yl)carbamate. LCMS (Method B): Rt = 0.76 mins, MH+ = 461.2 |

Example 23: ((cis)-5-Amino-2-methylpiperidin-1-yl)(2-(1-(cyclopropylmethyl)-1H-pyrrolo[2,3-b]pyridin-2-yl)-7-methoxy-1-methyl-1H-benzo[d]imidazol-5-yl)methanone, hydrochloride (Enantiomer of Example 24 with Cis-Relative Stereochemistry)

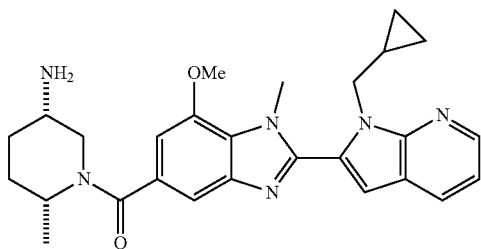 [SMILES: COc1cc(C(=O)N2C[C@@H](N)CC[C@H]2C)cc2nc(-c3cc4cccnc4n3CC3CC3)n(C)c12]

To a flask containing tert-butyl ((3S,6R)-1-(2-(1-(cyclopropylmethyl)-1H-pyrrolo[2,3-b]pyridin-2-yl)-7-methoxy-1-methyl-1H-benzo[d]imidazole-5-carbonyl)-6-methylpiperidin-3-yl)carbamate (47 mg, 0.082 mmol) in dichloromethane (DCM) (1 mL) was added TFA (0.253 mL, 3.28 mmol) and the reaction was stirred for 2.5 h. The reaction mixture was concentrated in vacuo to afford a brown oil. This was dissolved in methanol and loaded onto an SCX cartridge (5 g). It was eluted with methanol (3 column volumes) and product eluted as free base with 2M ammonia in methanol. The filtrate from the ammonia fractions was concentrated in vacuo to yield a yellow oil—((2R,5S)-5-amino-2-methylpiperidin-1-yl)(2-(1-(cyclopropylmethyl)-1H-pyrrolo[2,3-b]pyridin-2-yl)-7-methoxy-1-methyl-1H-benzo[d]imidazol-5-yl)methanone (35 mg, 0.074 mmol, 90% yield). The free base (35 mg) was dissolved in dichloromethane (DCM) (1 mL) in a vial and HCl (2M in Et$_2$O) (0.037 mL, 0.074 mmol) was added. The resultant suspension was sonicated for 5 min and allowed to stand for 15 min. The solvent was then removed under a positive pressure of nitrogen and the product dried in vacuo to afford ((2R,5S)-5-amino-2-methylpiperidin-1-yl)(2-(1-(cyclopropylmethyl)-1H-pyrrolo[2,3-b]pyridin-2-yl)-7-methoxy-1-methyl-1H-benzo[d]imidazol-5-yl)methanone, hydrochloride (37 mg, 0.073 mmol, 89% yield) as a beige solid.

LCMS (Method A): Rt=0.98 min, MH+=473.3

Example 24: ((cis)-5-Amino-2-methylpiperidin-1-yl)(2-(1-(cyclopropylmethyl)-1H-pyrrolo[2,3-b]pyridin-2-yl)-7-methoxy-1-methyl-1H-benzo[d]imidazol-5-yl)methanone, hydrochloride (Enantiomer of Example 23 with Cis-Relative Stereochemistry)

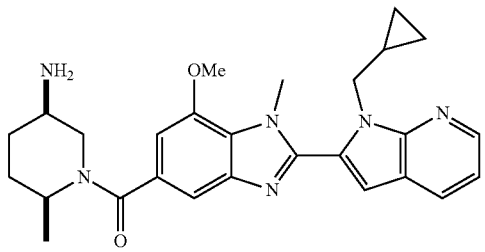 [SMILES: COc1cc(C(=O)N2C[C@H](N)CC[C@@H]2C)cc2nc(-c3cc4cccnc4n3CC3CC3)n(C)c12]

Prepared in a similar manner to Example 23 from tert-butyl ((3S,6R)-1-(2-(1-(cyclopropylmethyl)-1H-pyrrolo[2,3-b]pyridin-2-yl)-7-methoxy-1-methyl-1H-benzo[d]imidazole-5-carbonyl)-6-methylpiperidin-3-yl)carbamate.
LCMS (Method A): Rt=0.98 min, MH+=473.3
Biological Data
PAD4 Enzyme Expression
Recombinant human PAD4 (residues 1-663) was expressed in E. coli as an N-terminal GST-tagged fusion protein. During purification of the protein, the GST tag was removed by cleavage with PreScission Protease (GE Healthcare). Activity of the final product was determined using a FLINT $NH_3$ release assay.
PAD4 Enzyme Assay: Conditions A
8 μl of PAD4 enzyme diluted to an assay concentration of 75 nm in assay buffer (a).: (100 mM HEPES, 50 mM NaCl, 2 mM DTT and 0.6 mg/ml BSA pH 8), or in assay buffer (b).: (100 mM HEPES, 50 mM NaCl, 2 mM DTT, 7.5% glycerol and 1.5 mM CHAPS pH 8), and added to wells containing 0.1 μl of various concentrations of compound or DMSO vehicle (0.8% final) in a Greiner high volume 384 well black plate. Following 30 mins pre-incubation at room temperature, the reaction was initiated by the addition of 4 μl of substrate buffer containing 3 mM N-a-benzoyl-L-arginine ethyl ester (BAEE), 100 mM HEPES, 50 mM NaCl, 600 uM $CaCl_2$ ($2H_2O$) and 2 mM DTT, pH 8.0. The reaction was stopped after 100 mins with the addition of 38 μl stop/detection buffer containing 50 mM EDTA, 2.6 mM phthalaldehyde and 2.6 mM DTT. Assay incubated at room temperature for 90 mins before measuring fluorescent signal ($\lambda_{ex}$ 413/$\lambda_{em}$ 476) on an Envision plate reader (Perkin Elmer Life Sciences, Waltham, Mass., USA)
PAD4 Enzyme Assay: Conditions B
8 μl of PAD4 enzyme diluted to an assay concentration of 30 nM in assay buffer (100 mM HEPES, 50 mM NaCl, 2 mM DTT and 0.6 mg/ml BSA pH 8), and added to wells containing 0.1 μl of various concentrations of compound or DMSO vehicle (0.8% final) in a Greiner high volume 384 well black plate. Following 30 mins pre-incubation at room temperature, the reaction was initiated by the addition of 4 μl of substrate buffer containing 3 mM N-a-benzoyl-L-arginine ethyl ester (BAEE), 100 mM HEPES, 50 mM NaCl, 600 uM $CaCl_2$ ($2H_2O$) and 2 mM DTT, pH 8.0. The reaction was stopped after 60 mins with the addition of 38 μl stop/detection buffer containing 50 mM EDTA, 2.6 mM phthalaldehyde and 2.6 mM DTT. Assay incubated at room temperature for 90 mins before measuring fluorescent signal ($\lambda_{ex}$ 405/$\lambda_{em}$ 460) on an Envision plate reader (Perkin Elmer Life Sciences, Waltham, Mass., USA)
PAD2 Enzyme Expression
Recombinant human PAD2 (residues 1-665) was expressed in baculovirus-infected Sf9 insect cells as an N-terminal 6His-FLAG-tagged fusion protein. Activity of the final product was determined using a FLINT $NH_3$ release assay.
PAD2 Enzyme Assay
8 μl of PAD2 enzyme diluted to an assay concentration of 30 nM in assay buffer (100 mM HEPES, 50 mM NaCl, 2 mM DTT, 7.5% glycerol and 1.5 mM CHAPS pH 8), and added to wells containing 0.1 μl of various concentrations of compound or DMSO vehicle (0.8% final) in a Greiner high volume 384 well black plate. Following 30 mins pre-incubation at room temperature, the reaction was initiated by the addition of 4 μl of substrate buffer containing 180 uM N-a-benzoyl-L-arginine ethyl ester (BAEE), 100 mM HEPES, 50 mM NaCl, 240 uM $CaCl_2$ ($2H_2O$) and 2 mM DTT, pH 8.0. The reaction was stopped after 90 mins with the addition of 38 μl stop/detection buffer containing 50 mM EDTA, 2.6 mM phthalaldehyde and 2.6 mM DTT. Assay incubated at room temperature for 90 mins before measuring fluorescent signal ($\lambda_{ex}$ 405/$\lambda_{em}$ 460) on an Envision plate reader (Perkin Elmer Life Sciences, Waltham, Mass., USA)
Results
Examples 1, 2A, 2B, 3, 4A, 4B, 5B, 6, 7, 8, 9A, 9B, 10B, 11A, 11B, 12, 13, 14, 15, 16, 17, 18, 19, 20, 21, 22, 23 and 24 were tested in the PAD4 enzyme assay above or similar assays and had a mean pIC50 in the range of 5 to 7.5. The mean $pIC_{50}$ for Example 5B was 6.7; Example 9B, mean $pIC_{50}$ was 6.7; Example 10B, mean $pIC_{50}$ was 7.3; Example 11B, mean $pIC_{50}$ was 6.9; for Example 14, mean $pIC_{50}$ was 7.1.
To assess selectivity for PAD4 over PAD2, the following examples 2B, 5B, 9B, 10B, 11B, 13, 16, 19 and 22 were tested in the PAD2 enzyme assay above or similar assays and had a mean $pIC_{50}$ in the range of <4.1 to 4.2. The mean $pIC_{50}$ values for Examples 5B, 9B, 10B, 11B, and 14 were all <4.1.

The invention claimed is:
1. A method of treating deep vein thrombosis, periodontitis, sepsis, appendicitis, spinal cord injuries, or stroke, comprising administering to a patient in need thereof a PAD4 inhibitory affective amount of a compound of formula I:

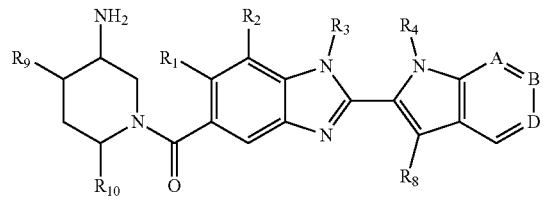

or a pharmaceutically acceptable salt thereof, wherein:
$R_1$ is hydrogen or $C_{1-6}$alkyl;
$R_2$ is hydrogen, $C_{1-6}$alkyl, perhalomethyl$C_{0-5}$alkyl-O—, or $C_{1-6}$alkoxy;
$R_3$ is hydrogen, $C_{1-6}$alkyl, or $C_{1-6}$alkoxy$C_{1-6}$alkyl;
$R_4$ is hydrogen, $C_{1-6}$alkyl, halomethyl$C_{1-6}$alkyl; or unsubstituted $C_{3-6}$cycloalkyl$C_{1-6}$alkyl;

A is C—$R_5$ or N;
B is C—$R_6$ or N;
D is C—$R_7$ or N;
   with the proviso that at least one of A, B, and D, is N;
$R_5$ is hydrogen or $C_{1-6}$alkyl;
$R_6$ is hydrogen or $C_{1-6}$alkyl;
$R_7$ is hydrogen, $C_{1-6}$alkyl, $C_{1-6}$alkoxy, or hydroxy;
$R_8$ is hydrogen or $C_{1-6}$alkyl, with the proviso that one of $R_4$ and $R_8$ is hydrogen;
$R_9$ is hydrogen or hydroxy; and
$R_{10}$ is hydrogen or $C_{1-6}$alkyl;
or a pharmaceutically acceptable composition comprising said compound of formula I.

2. The method according to claim 1, wherein:
$R_1$ is hydrogen;
$R_2$ is hydrogen, $C_{1-6}$alkyl or $C_{1-6}$alkoxy;
$R_3$ is $C_{1-6}$alkyl; and
$R_4$ is $C_{1-6}$alkyl, unsubstituted $C_{3-6}$cycloalkyl$C_{1-6}$alkyl, or perhalomethyl$C_{1-6}$alkyl.

3. The method according to claim 2, wherein $R_2$ is $C_{1-6}$alkoxy.

4. The method according to claim 3, wherein $R_9$ is hydrogen.

5. The method according to claim 3, wherein $R_9$ is hydroxy.

6. The method according to claim 3, wherein $R_{10}$ is hydrogen.

7. The method according to claim 3, wherein $R_{10}$ is $C_{1-6}$alkyl.

8. The method according to claim 1, wherein said compound, or pharmaceutically acceptable salt thereof, is selected from the group consisting of:
   1-{[2-(1-ethyl-1H-pyrrolo[3,2-c]pyridin-2-yl)-1-methyl-1H-benzimidazol-5-yl]carbonyl}-3-piperidinamine;
   (R)-(3-aminopiperidin-1-yl)(2-(1-ethyl-1H-pyrrolo[2,3-b]pyridin-2-yl)-1-methyl-1H-benzo[d]imidazol-5-yl)methanone;
   (R)-(3-aminopiperidin-1-yl)(2-(1-ethyl-1H-pyrrolo[2,3-c]pyridin-2-yl)-1-methyl-1H-benzo[d]imidazol-5-yl)methanone;
   (R)-(3-aminopiperidin-1-yl)(1-methyl-2-(1-(2,2,2-trifluoroethyl)-1H-pyrrolo[2,3-b]pyridin-2-yl)-1H-benzo[d]imidazol-5-yl)methanone;
   (R)-(3-aminopiperidin-1-yl)(2-(1-(cyclopropylmethyl)-1H-pyrrolo[2,3-b]pyridin-2-yl)-1-methyl-1H-benzo[d]imidazol-5-yl)methanone;
   (R)-(3-aminopiperidin-1-yl)(2-(1-ethyl-5-methoxy-1H-pyrrolo[2,3-b]pyridin-2-yl)-1-methyl-1H-benzo[d]imidazol-5-yl)methanone;
   (R)-(3-aminopiperidin-1-yl)(2-(1-ethyl-5-methoxy-1H-pyrrolo[2,3-c]pyridin-2-yl)-1-methyl-1H-benzo[d]imidazol-5-yl)methanone;
   2-(5-{[(3R)-3-amino-1-piperidinyl]carbonyl}-1-methyl-1H-benzimidazol-2-yl)-1-ethyl-1H-pyrrolo[2,3-b]pyridin-5-ol;
   (R)-(3-aminopiperidin-1-yl)(2-(1-ethyl-1H-pyrrolo[2,3-b]pyridin-2-yl)-7-methoxy-1-methyl-1H-benzo[d]imidazol-5-yl)methanone;
   (R)-(3-aminopiperidin-1-yl)(2-(1-(cyclopropylmethyl)-1H-pyrrolo[2,3-b]pyridin-2-yl)-7-methoxy-1-methyl-1H-benzo[d]imidazol-5-yl)methanone;
   (R)-(3-aminopiperidin-1-yl)(7-methoxy-1-methyl-2-(1-(2,2,2-trifluoroethyl)-1H-pyrrolo[2,3-b]pyridin-2-yl)-1H-benzo[d]imidazol-5-yl)methanone;
   (3-aminopiperidin-1-yl)(2-(1-ethyl-1H-pyrrolo[2,3-b]pyridin-2-yl)-1-methyl-1H-benzo[d]imidazol-5-yl)methanone;
   ((3S,4R)-3-amino-4-hydroxypiperidin-1-yl)(2-(1-(cyclopropylmethyl)-1H-pyrrolo[2,3-b]pyridin-2-yl)-1-methyl-1H-benzo[d]imidazol-5-yl)methanone;
   ((3S,4R)-3-amino-4-hydroxypiperidin-1-yl)(2-(1-(cyclopropylmethyl)-1H-pyrrolo[2,3-b]pyridin-2-yl)-7-methoxy-1-methyl-1H-benzo[d]imidazol-5-yl)methanone;
   (R)-(3-aminopiperidin-1-yl)(2-(1-ethyl-1H-pyrrolo[2,3-b]pyridin-2-yl)-1-methyl-7-(trifluoromethoxy)-1H-benzo[d]imidazol-5-yl)methanone;
   (R)-(3-aminopiperidin-1-yl)(7-methoxy-1-methyl-2-(1-neopentyl-1H-pyrrolo[2,3-b]pyridin-2-yl)-1H-benzo[d]imidazol-5-yl)methanone;
   ((R)-3-aminopiperidin-1-yl)(7-methoxy-1-methyl-2-(1-(2-methylbutyl)-1H-pyrrolo[2,3-b]pyridin-2-yl)-1H-benzo[d]imidazol-5-yl)methanone;
   (R)-(3-aminopiperidin-1-yl)(2-(1-ethyl-1H-pyrrolo[2,3-b]pyridin-2-yl)-7-methoxy-1-(2-methoxyethyl)-1H-benzo[d]imidazol-5-yl)methanone;
   (S)-(3-aminopiperidin-1-yl)(2-(1-ethyl-1H-pyrrolo[2,3-b]pyridin-2-yl)-7-methoxy-1-methyl-1H-benzo[d]imidazol-5-yl)methanone;
   (R)-(3-aminopiperidin-1-yl)(2-(1-ethyl-1H-pyrrolo[2,3-b]pyridin-2-yl)-1-isobutyl-7-methoxy-1H-benzo[d]imidazol-5-yl)methanone;
   (R)-(3-aminopiperidin-1-yl)(7-methoxy-2-(1-(2-methoxy-2-methylpropyl)-1H-pyrrolo[2,3-b]pyridin-2-yl)-1-methyl-1H-benzo[d]imidazol-5-yl)methanone;
   (R)-(3-aminopiperidin-1-yl)(2-(1-isobutyl-1H-pyrrolo[2,3-b]pyridin-2-yl)-7-methoxy-1-methyl-1H-benzo[d]imidazol-5-yl)methanone; and
   ((cis)-5-amino-2-methylpiperidin-1-yl)(2-(1-(cyclopropylmethyl)-1H-pyrrolo[2,3-b]pyridin-2-yl)-7-methoxy-1-methyl-1H-benzo[d]imidazol-5-yl)methanone.

9. The method according to claim 1, wherein said method comprises administering to said patient a pharmaceutically acceptable composition comprising said compound of formula I.

* * * * *